(12) United States Patent
Connor

(10) Patent No.: US 9,042,596 B2
(45) Date of Patent: May 26, 2015

(54) WILLPOWER WATCH (TM)—A WEARABLE FOOD CONSUMPTION MONITOR

(75) Inventor: Robert A. Connor, Forest Lake, MN (US)

(73) Assignee: Medibotics LLC, Forest Lake, MN (US)

( * ) Notice: Subject to any disclaimer, the term of this patent is extended or adjusted under 35 U.S.C. 154(b) by 518 days.

(21) Appl. No.: 13/523,739

(22) Filed: Jun. 14, 2012

(65) Prior Publication Data

US 2013/0336519 A1  Dec. 19, 2013

(51) Int. Cl.
*G06K 9/00* (2006.01)
*G06K 9/22* (2006.01)

(52) U.S. Cl.
CPC ............ *G06K 9/00771* (2013.01); *G06K 9/228* (2013.01); *G06K 2209/17* (2013.01)

(58) Field of Classification Search
None
See application file for complete search history.

(56) References Cited

U.S. PATENT DOCUMENTS

| | | | |
|---|---|---|---|
| 3,885,576 A | 5/1975 | Symmes |
| 4,100,401 A | 7/1978 | Tutt et al. |
| 4,192,000 A | 3/1980 | Lipsey |
| 4,207,673 A | 6/1980 | DiGirolamo et al. |
| 4,212,079 A | 7/1980 | Segar et al. |
| 4,218,611 A | 8/1980 | Cannon |
| 4,221,959 A | 9/1980 | Sessler |
| 4,310,316 A | 1/1982 | Thomann |
| 4,321,674 A | 3/1982 | Krames et al. |
| 4,355,645 A | 10/1982 | Mitani et al. |
| 4,387,777 A | 6/1983 | Ash |
| 4,509,531 A | 4/1985 | Ward |
| 4,650,218 A | 3/1987 | Hawke |
| 4,686,624 A | 8/1987 | Blum et al. |
| 4,757,453 A | 7/1988 | Nasiff |
| 4,796,182 A | 1/1989 | Duboff |
| 4,819,860 A | 4/1989 | Hargrove et al. |
| 4,823,808 A | 4/1989 | Clegg et al. |
| 4,875,533 A | 10/1989 | Mihara et al. |
| 4,891,756 A | 1/1990 | Williams |

(Continued)

FOREIGN PATENT DOCUMENTS

| | | |
|---|---|---|
| WO | WO 9728738 | 8/1997 |
| WO | WO 03032629 | 4/2003 |

(Continued)

OTHER PUBLICATIONS

Lee, Nicole, "AIRO wristband tracks not just sleep, exercise and stress, but also what you eat," Engadget, Oct. 28, 2013, http://www.engadget.com/2013/10/28/airo-wristband/.

(Continued)

*Primary Examiner* — Bhavesh Mehta
*Assistant Examiner* — Andrew Moyer

(57) ABSTRACT

This invention is a wearable, automatic, and tamper-resistant device and method for monitoring and measuring food consumption and caloric intake. It can help people to manage their energy balance and weight. It can be embodied as: (a) one or more automatic-imaging members that are worn on a person from which these members collectively and automatically take pictures of the person's mouth and pictures of a reachable food source when the person eats; (b) a tamper-resisting mechanism which detects and responds if the operation of the one or more automatic-imaging members is impaired; and (c) an image-analyzing member which automatically analyzes pictures of the person's mouth and pictures of the reachable food source in order to estimate the types and quantities of food that are consumed by the person.

19 Claims, 10 Drawing Sheets

(56) References Cited

U.S. PATENT DOCUMENTS

| | | |
|---|---|---|
| 4,911,256 A | 3/1990 | Attikiouzel |
| 4,914,819 A | 4/1990 | Ash |
| 4,917,108 A | 4/1990 | Mault |
| 4,951,197 A | 8/1990 | Mellinger |
| 4,965,553 A | 10/1990 | DelBiondo et al. |
| 4,975,682 A | 12/1990 | Kerr et al. |
| 5,033,561 A | 7/1991 | Hettinger |
| 5,038,792 A | 8/1991 | Mault |
| 5,050,612 A | 9/1991 | Matsumura |
| 5,067,488 A | 11/1991 | Fukada et al. |
| 5,148,002 A | 9/1992 | Kuo et al. |
| 5,173,588 A | 12/1992 | Harrah |
| 5,233,520 A | 8/1993 | Kretsch et al. |
| 5,263,491 A | 11/1993 | Thornton |
| 5,285,398 A | 2/1994 | Janik |
| 5,299,356 A | 4/1994 | Maxwell |
| 5,301,679 A | 4/1994 | Taylor |
| 5,388,043 A | 2/1995 | Hettinger |
| 5,398,688 A | 3/1995 | Laniado |
| 5,412,564 A | 5/1995 | Ecer |
| 5,421,089 A | 6/1995 | Dubus et al. |
| 5,424,719 A | 6/1995 | Ravid |
| 5,478,989 A | 12/1995 | Shepley |
| 5,491,651 A | 2/1996 | Janik |
| 5,497,772 A | 3/1996 | Schulman et al. |
| 5,515,858 A | 5/1996 | Myllymaki |
| 5,542,420 A | 8/1996 | Goldman et al. |
| 5,555,490 A | 9/1996 | Carroll |
| 5,563,850 A | 10/1996 | Hanapole |
| 5,581,492 A | 12/1996 | Janik |
| 5,636,146 A | 6/1997 | Flentov et al. |
| 5,673,691 A | 10/1997 | Abrams et al. |
| 5,691,927 A | 11/1997 | Gump |
| 5,704,350 A | 1/1998 | Williams |
| 5,729,479 A | 3/1998 | Golan |
| 5,817,006 A | 10/1998 | Bergh et al. |
| 5,819,735 A | 10/1998 | Mansfield et al. |
| 5,836,312 A | 11/1998 | Moore |
| 5,839,901 A | 11/1998 | Karkanen |
| 5,841,115 A | 11/1998 | Shepley |
| 5,890,128 A | 3/1999 | Diaz et al. |
| 5,908,301 A | 6/1999 | Lutz |
| 5,989,188 A | 11/1999 | Birkhoelzer et al. |
| 6,024,281 A | 2/2000 | Shepley |
| 6,032,676 A | 3/2000 | Moore |
| 6,040,531 A | 3/2000 | Miller-Kovach |
| 6,083,006 A | 7/2000 | Coffman |
| 6,095,949 A | 8/2000 | Arai |
| 6,095,985 A | 8/2000 | Raymond et al. |
| 6,135,950 A | 10/2000 | Adams |
| 6,135,951 A | 10/2000 | Richardson et al. |
| 6,218,358 B1 | 4/2001 | Firestein et al. |
| 6,249,697 B1 | 6/2001 | Asano |
| 6,266,623 B1 | 7/2001 | Vock et al. |
| 6,283,914 B1 | 9/2001 | Mansfield et al. |
| 6,290,646 B1 | 9/2001 | Cosentino et al. |
| 6,336,136 B1 | 1/2002 | Harris |
| 6,341,295 B1 | 1/2002 | Stotler |
| 6,387,329 B1 | 5/2002 | Lewis et al. |
| 6,425,862 B1 | 7/2002 | Brown |
| 6,454,705 B1 | 9/2002 | Cosentino et al. |
| 6,473,368 B1 | 10/2002 | Stanfield |
| 6,478,736 B1 | 11/2002 | Mault |
| 6,498,994 B2 | 12/2002 | Vock et al. |
| 6,506,152 B1 | 1/2003 | Lackey et al. |
| 6,508,762 B2 | 1/2003 | Karnieli |
| 6,513,532 B2 | 2/2003 | Mault et al. |
| 6,527,711 B1 | 3/2003 | Stivoric et al. |
| 6,553,386 B1 | 4/2003 | Alabaster |
| 6,571,200 B1 | 5/2003 | Mault |
| 6,572,542 B1 | 6/2003 | Houben et al. |
| 6,595,929 B2 | 7/2003 | Stivoric et al. |
| 6,605,038 B1 | 8/2003 | Teller et al. |
| 6,610,367 B2 | 8/2003 | Lewis et al. |
| 6,635,015 B2 | 10/2003 | Sagel |
| 6,675,041 B2 | 1/2004 | Dickinson |
| 6,694,182 B1 | 2/2004 | Yamazaki et al. |
| 6,723,045 B2 | 4/2004 | Cosentino et al. |
| 6,745,214 B2 | 6/2004 | Inoue et al. |
| 6,755,783 B2 | 6/2004 | Cosentino et al. |
| 6,765,488 B2 | 7/2004 | Stanfield |
| 6,790,178 B1 | 9/2004 | Mault et al. |
| 6,850,861 B1 | 2/2005 | Faiola et al. |
| 6,856,934 B2 | 2/2005 | Vock et al. |
| 6,856,938 B2 | 2/2005 | Kurtz |
| 6,878,885 B2 | 4/2005 | Miller-Kovach |
| 6,893,406 B2 | 5/2005 | Takeuchi et al. |
| 6,917,897 B2 | 7/2005 | Mork |
| 6,978,221 B1 | 12/2005 | Rudy |
| 7,020,508 B2 | 3/2006 | Stivoric et al. |
| 7,044,739 B2 | 5/2006 | Matson |
| 7,054,784 B2 | 5/2006 | Flentov et al. |
| 7,057,551 B1 | 6/2006 | Vogt |
| 7,096,221 B2 | 8/2006 | Nakano |
| 7,122,152 B2 | 10/2006 | Lewis et al. |
| 7,153,262 B2 | 12/2006 | Stivoric et al. |
| 7,192,136 B2 | 3/2007 | Howell et al. |
| 7,241,880 B2 | 7/2007 | Adler et al. |
| 7,247,023 B2 | 7/2007 | Peplinski et al. |
| 7,255,437 B2 | 8/2007 | Howell et al. |
| 7,261,690 B2 | 8/2007 | Teller et al. |
| 7,285,090 B2 | 10/2007 | Stivoric et al. |
| 7,361,141 B2 | 4/2008 | Nissila et al. |
| 7,373,820 B1 | 5/2008 | James |
| 7,398,151 B1 | 7/2008 | Burrell et al. |
| 7,401,918 B2 | 7/2008 | Howell et al. |
| 7,438,410 B1 | 10/2008 | Howell et al. |
| 7,451,056 B2 | 11/2008 | Flentov et al. |
| 7,454,002 B1 | 11/2008 | Gardner et al. |
| 7,481,531 B2 | 1/2009 | Howell et al. |
| 7,500,937 B2 | 3/2009 | Hercules |
| 7,502,643 B2 | 3/2009 | Farringdon et al. |
| 7,512,515 B2 | 3/2009 | Vock et al. |
| 7,550,683 B2 | 6/2009 | Daughtry |
| 7,577,475 B2 | 8/2009 | Cosentino et al. |
| 7,595,023 B2 | 9/2009 | Lewis et al. |
| 7,640,804 B2 | 1/2010 | Daumer et al. |
| 7,651,868 B2 | 1/2010 | Mcdevitt et al. |
| 7,689,437 B1 | 3/2010 | Teller et al. |
| 7,717,866 B2 | 5/2010 | Damen |
| 7,736,318 B2 | 6/2010 | Cosentino et al. |
| 7,769,635 B2 | 8/2010 | Simons-Nikolova |
| 7,805,196 B2 | 9/2010 | Miesel et al. |
| 7,841,966 B2 | 11/2010 | Aaron et al. |
| 7,855,936 B2 | 12/2010 | Czarnek et al. |
| 7,857,730 B2 | 12/2010 | Dugan |
| 7,878,975 B2 | 2/2011 | Liljeryd et al. |
| 7,882,150 B2 | 2/2011 | Badyal |
| 7,899,709 B2 | 3/2011 | Allard et al. |
| 7,905,815 B2 | 3/2011 | Ellis et al. |
| 7,905,832 B1 | 3/2011 | Lau et al. |
| 7,914,468 B2 | 3/2011 | Shalon et al. |
| 7,931,562 B2 | 4/2011 | Ellis et al. |
| 7,949,506 B1 | 5/2011 | Hill et al. |
| 7,956,997 B2 | 6/2011 | Wang et al. |
| 7,959,567 B2 | 6/2011 | Stivoric et al. |
| 7,980,997 B2 | 7/2011 | Thukral et al. |
| 7,999,674 B2 | 8/2011 | Kamen |
| 8,021,297 B2 | 9/2011 | Aerts |
| 8,033,959 B2 | 10/2011 | Oleson et al. |
| 8,067,185 B2 | 11/2011 | Zoller et al. |
| 8,068,858 B2 | 11/2011 | Werner et al. |
| 8,073,707 B2 | 12/2011 | Teller et al. |
| 8,075,451 B2 | 12/2011 | Dugan |
| 8,087,937 B2 | 1/2012 | Peplinski et al. |
| 8,112,281 B2 | 2/2012 | Yeung et al. |
| 8,116,841 B2 | 2/2012 | Bly et al. |
| 8,121,673 B2 | 2/2012 | Tran |
| 8,157,731 B2 | 4/2012 | Teller et al. |
| 8,158,082 B2 | 4/2012 | Imran |
| 8,162,804 B2 | 4/2012 | Tagliabue |
| 8,170,656 B2 | 5/2012 | Tan et al. |
| 8,180,591 B2 | 5/2012 | Yuen et al. |
| 8,180,592 B2 | 5/2012 | Yuen et al. |

(56) References Cited

U.S. PATENT DOCUMENTS

| | | |
|---|---|---|
| 8,184,070 B1 | 5/2012 | Taubman |
| 8,229,676 B2 | 7/2012 | Hyde et al. |
| 8,236,242 B2 | 8/2012 | Drucker et al. |
| 8,244,278 B2 | 8/2012 | Werner et al. |
| 8,265,907 B2 | 9/2012 | Nanikashvili et al. |
| 8,275,438 B2 | 9/2012 | Simpson et al. |
| 8,275,635 B2 | 9/2012 | Stivoric et al. |
| 8,280,476 B2 | 10/2012 | Jina |
| 8,285,356 B2 | 10/2012 | Bly et al. |
| 8,285,488 B2 | 10/2012 | Hyde et al. |
| 8,287,453 B2 | 10/2012 | Li et al. |
| 8,290,712 B2 | 10/2012 | Hyde et al. |
| 8,294,581 B2 | 10/2012 | Kamen |
| 8,298,142 B2 | 10/2012 | Simpson et al. |
| 8,299,930 B2 | 10/2012 | Schmid-Schonbein et al. |
| 8,310,368 B2 | 11/2012 | Hoover et al. |
| 8,311,769 B2 | 11/2012 | Yuen et al. |
| 8,311,770 B2 | 11/2012 | Yuen et al. |
| 8,314,224 B2 | 11/2012 | Adler et al. |
| 8,321,141 B2 | 11/2012 | Hyde et al. |
| 8,323,188 B2 | 12/2012 | Tran |
| 8,323,189 B2 | 12/2012 | Tran et al. |
| 8,323,218 B2 | 12/2012 | Davis et al. |
| 8,328,718 B2 | 12/2012 | Tran |
| 8,330,057 B2 | 12/2012 | Sharawi et al. |
| 8,334,367 B2 | 12/2012 | Adler |
| 8,337,367 B2 | 12/2012 | Dugan |
| 8,340,754 B2 | 12/2012 | Chamney et al. |
| 8,344,325 B2 | 1/2013 | Merrell et al. |
| 8,344,998 B2 | 1/2013 | Fitzgerald et al. |
| 8,345,414 B2 | 1/2013 | Mooring et al. |
| 8,345,930 B2 | 1/2013 | Tamrakar et al. |
| 8,352,211 B2 | 1/2013 | Vock et al. |
| 8,355,875 B2 | 1/2013 | Hyde et al. |
| 8,363,913 B2 | 1/2013 | Boushey et al. |
| 8,364,250 B2 | 1/2013 | Moon et al. |
| 8,369,919 B2 | 2/2013 | Kamath et al. |
| 8,369,936 B2 | 2/2013 | Farringdon et al. |
| 8,370,176 B2 | 2/2013 | Vespasiani |
| 8,370,549 B2 | 2/2013 | Burton et al. |
| 8,378,811 B2 | 2/2013 | Crump et al. |
| 8,379,488 B1 | 2/2013 | Gossweiler et al. |
| 8,382,482 B2 | 2/2013 | Miller-Kovach et al. |
| 8,382,681 B2 | 2/2013 | Escutia et al. |
| 8,386,008 B2 | 2/2013 | Yuen et al. |
| 8,386,185 B2 | 2/2013 | Hyde et al. |
| 8,392,123 B2 | 3/2013 | Hyde et al. |
| 8,392,124 B2 | 3/2013 | Hyde et al. |
| 8,392,125 B2 | 3/2013 | Hyde et al. |
| 8,396,672 B2 | 3/2013 | Hyde et al. |
| 8,398,546 B2 | 3/2013 | Pacione et al. |
| 8,403,845 B2 | 3/2013 | Stivoric et al. |
| 8,408,436 B2 | 4/2013 | Berry et al. |
| 8,409,118 B2 | 4/2013 | Agrawal et al. |
| 8,416,102 B2 | 4/2013 | Yin |
| 8,417,298 B2 | 4/2013 | Mittleman et al. |
| 8,417,312 B2 | 4/2013 | Kamath et al. |
| 8,419,268 B2 | 4/2013 | Yu |
| 8,421,620 B2 | 4/2013 | Boyd et al. |
| 8,421,634 B2 | 4/2013 | Tan et al. |
| 8,423,113 B2 | 4/2013 | Shariati et al. |
| 8,423,378 B1 | 4/2013 | Goldberg |
| 8,423,380 B1 | 4/2013 | Gelly |
| 8,425,415 B2 | 4/2013 | Tran |
| 8,437,823 B2 | 5/2013 | Ozawa et al. |
| 8,437,980 B2 | 5/2013 | Yuen et al. |
| 8,438,038 B2 | 5/2013 | Cosentino et al. |
| 8,438,163 B1 | 5/2013 | Li et al. |
| 8,439,683 B2 | 5/2013 | Puri et al. |
| 8,446,275 B2 | 5/2013 | Utter |
| 8,447,403 B2 | 5/2013 | Sharma et al. |
| 8,447,404 B2 | 5/2013 | Sharma et al. |
| 8,449,560 B2 | 5/2013 | Roth et al. |
| 8,463,573 B2 | 6/2013 | Flentov et al. |
| 8,463,576 B2 | 6/2013 | Yuen et al. |
| 8,463,577 B2 | 6/2013 | Yuen et al. |
| 8,465,447 B2 | 6/2013 | Krueger et al. |
| 8,467,869 B2 | 6/2013 | Schuler |
| 8,475,367 B1 | 7/2013 | Yuen et al. |
| 8,475,368 B2 | 7/2013 | Tran et al. |
| 8,475,370 B2 | 7/2013 | McCombie et al. |
| 8,478,398 B2 | 7/2013 | Schuler |
| 8,478,606 B2 | 7/2013 | Bodlaender et al. |
| 8,483,830 B2 | 7/2013 | Tweden et al. |
| 8,486,153 B2 | 7/2013 | Levine et al. |
| 8,571,880 B2 | 10/2013 | Goldberg |
| 8,583,402 B2 | 11/2013 | Yuen et al. |
| 8,585,771 B2 | 11/2013 | Binmoeller et al. |
| 8,587,670 B2 | 11/2013 | Wood et al. |
| 8,595,023 B2 | 11/2013 | Kirchhoff et al. |
| 8,600,928 B2 | 12/2013 | Landers |
| 8,603,186 B2 | 12/2013 | Binmoeller |
| 8,605,952 B2 | 12/2013 | Boushey et al. |
| 2001/0049470 A1* | 12/2001 | Mault et al. .................. 600/300 |
| 2002/0022774 A1 | 2/2002 | Karnieli |
| 2002/0027164 A1 | 3/2002 | Mault et al. |
| 2002/0047867 A1 | 4/2002 | Mault et al. |
| 2002/0049482 A1 | 4/2002 | Fabian et al. |
| 2002/0062069 A1 | 5/2002 | Mault |
| 2002/0109600 A1 | 8/2002 | Mault et al. |
| 2002/0124017 A1 | 9/2002 | Mault |
| 2002/0133378 A1 | 9/2002 | Mault et al. |
| 2002/0156351 A1 | 10/2002 | Sagel |
| 2002/0167863 A1 | 11/2002 | Davis et al. |
| 2003/0065257 A1 | 4/2003 | Mault et al. |
| 2003/0076983 A1 | 4/2003 | Cox |
| 2003/0152607 A1 | 8/2003 | Mault |
| 2003/0163354 A1 | 8/2003 | Shamoun |
| 2003/0165799 A1 | 9/2003 | Bisogno |
| 2003/0208110 A1 | 11/2003 | Mault et al. |
| 2003/0219513 A1 | 11/2003 | Gordon |
| 2004/0034289 A1 | 2/2004 | Teller et al. |
| 2004/0073142 A1 | 4/2004 | Takeuchi et al. |
| 2004/0100376 A1 | 5/2004 | Lye et al. |
| 2004/0133081 A1 | 7/2004 | Teller et al. |
| 2004/0152957 A1 | 8/2004 | Stivoric et al. |
| 2005/0004436 A1 | 1/2005 | Nissila et al. |
| 2005/0008994 A1 | 1/2005 | Bisogno |
| 2005/0011367 A1 | 1/2005 | Crow |
| 2005/0014111 A1 | 1/2005 | Matson |
| 2005/0113649 A1 | 5/2005 | Bergantino |
| 2005/0113650 A1 | 5/2005 | Pacione et al. |
| 2005/0146419 A1 | 7/2005 | Porter |
| 2005/0153052 A1 | 7/2005 | Williams et al. |
| 2005/0184148 A1 | 8/2005 | Perlman |
| 2005/0247213 A1 | 11/2005 | Slilaty |
| 2005/0263160 A1 | 12/2005 | Utley et al. |
| 2005/0266385 A1 | 12/2005 | Bisogno |
| 2005/0283096 A1 | 12/2005 | Chau et al. |
| 2006/0015016 A1 | 1/2006 | Thornton |
| 2006/0031102 A1 | 2/2006 | Teller et al. |
| 2006/0036395 A1 | 2/2006 | Shaya et al. |
| 2006/0064037 A1 | 3/2006 | Shalon et al. |
| 2006/0074716 A1 | 4/2006 | Tilles et al. |
| 2006/0122468 A1 | 6/2006 | Tavor |
| 2006/0122474 A1 | 6/2006 | Teller et al. |
| 2006/0189853 A1 | 8/2006 | Brown |
| 2006/0197670 A1 | 9/2006 | Breibart |
| 2006/0229504 A1 | 10/2006 | Johnson |
| 2006/0263750 A1 | 11/2006 | Gordon |
| 2006/0264730 A1 | 11/2006 | Stivoric et al. |
| 2007/0021979 A1 | 1/2007 | Cosentino et al. |
| 2007/0027366 A1 | 2/2007 | Osburn |
| 2007/0028453 A1 | 2/2007 | Crow |
| 2007/0030339 A1 | 2/2007 | Findlay et al. |
| 2007/0050058 A1 | 3/2007 | Zuziak et al. |
| 2007/0059672 A1 | 3/2007 | Shaw |
| 2007/0089335 A1 | 4/2007 | Smith et al. |
| 2007/0098856 A1 | 5/2007 | LePine |
| 2007/0100666 A1 | 5/2007 | Stivoric et al. |
| 2007/0106129 A1 | 5/2007 | Srivathsa et al. |
| 2007/0173703 A1 | 7/2007 | Lee et al. |
| 2007/0179355 A1 | 8/2007 | Rosen |
| 2007/0208593 A1 | 9/2007 | Hercules |

(56) References Cited

U.S. PATENT DOCUMENTS

| | | |
|---|---|---|
| 2008/0019122 A1 | 1/2008 | Kramer |
| 2008/0036737 A1 | 2/2008 | Hernandez-Rebollar |
| 2008/0060853 A1 | 3/2008 | Davidson et al. |
| 2008/0137486 A1 | 6/2008 | Czarenk et al. |
| 2008/0140444 A1 | 6/2008 | Karkanias et al. |
| 2008/0161654 A1 | 7/2008 | Teller et al. |
| 2008/0161655 A1 | 7/2008 | Teller et al. |
| 2008/0167535 A1 | 7/2008 | Andre et al. |
| 2008/0167536 A1 | 7/2008 | Teller et al. |
| 2008/0167537 A1 | 7/2008 | Teller et al. |
| 2008/0167538 A1 | 7/2008 | Teller et al. |
| 2008/0167539 A1 | 7/2008 | Teller et al. |
| 2008/0171920 A1 | 7/2008 | Teller et al. |
| 2008/0171921 A1 | 7/2008 | Teller et al. |
| 2008/0171922 A1 | 7/2008 | Teller et al. |
| 2008/0255955 A1 | 10/2008 | Simons-Nikolova |
| 2008/0262557 A1 | 10/2008 | Brown |
| 2008/0267444 A1* | 10/2008 | Simons-Nikolova et al. ... 382/100 |
| 2008/0270324 A1 | 10/2008 | Allard et al. |
| 2008/0275309 A1 | 11/2008 | Stivoric et al. |
| 2008/0276461 A1 | 11/2008 | Gold |
| 2009/0012433 A1* | 1/2009 | Fernstrom et al. ........... 600/593 |
| 2009/0112800 A1 | 4/2009 | Athsani |
| 2009/0176526 A1 | 7/2009 | Altman |
| 2009/0177068 A1 | 7/2009 | Stivoric et al. |
| 2009/0191514 A1 | 7/2009 | Barnow |
| 2009/0219159 A1 | 9/2009 | Morgenstern |
| 2009/0253105 A1 | 10/2009 | Lepine |
| 2009/0261987 A1 | 10/2009 | Sun |
| 2010/0000292 A1 | 1/2010 | Karabacak et al. |
| 2010/0003647 A1 | 1/2010 | Brown et al. |
| 2010/0049004 A1 | 2/2010 | Edman et al. |
| 2010/0049010 A1 | 2/2010 | Goldreich |
| 2010/0055271 A1 | 3/2010 | Miller-Kovach et al. |
| 2010/0055652 A1 | 3/2010 | Miller-Kovach et al. |
| 2010/0055653 A1 | 3/2010 | Miller-Kovach et al. |
| 2010/0057564 A1 | 3/2010 | Godsey et al. |
| 2010/0062119 A1 | 3/2010 | Miller-Kovach |
| 2010/0062402 A1 | 3/2010 | Miller-Kovach |
| 2010/0079291 A1 | 4/2010 | Kroll et al. |
| 2010/0080875 A1 | 4/2010 | Miller-Kovach |
| 2010/0109876 A1 | 5/2010 | Schmid-Schonbein et al. |
| 2010/0111383 A1 | 5/2010 | Boushey et al. |
| 2010/0125176 A1 | 5/2010 | Hyde et al. |
| 2010/0125177 A1 | 5/2010 | Hyde et al. |
| 2010/0125178 A1 | 5/2010 | Hyde et al. |
| 2010/0125179 A1 | 5/2010 | Hyde et al. |
| 2010/0125180 A1 | 5/2010 | Hyde et al. |
| 2010/0125181 A1 | 5/2010 | Hyde et al. |
| 2010/0125417 A1 | 5/2010 | Hyde et al. |
| 2010/0125418 A1 | 5/2010 | Hyde et al. |
| 2010/0125419 A1 | 5/2010 | Hyde et al. |
| 2010/0125420 A1 | 5/2010 | Hyde et al. |
| 2010/0173269 A1 | 7/2010 | Puri et al. |
| 2010/0191155 A1 | 7/2010 | Kim et al. |
| 2010/0194573 A1 | 8/2010 | Hoover et al. |
| 2010/0205209 A1 | 8/2010 | Jokinen |
| 2010/0209897 A1 | 8/2010 | Utley et al. |
| 2010/0228160 A1 | 9/2010 | Schweizer |
| 2010/0240962 A1 | 9/2010 | Contant |
| 2010/0291515 A1 | 11/2010 | Pinnisi et al. |
| 2010/0332571 A1 | 12/2010 | Healey et al. |
| 2011/0053128 A1 | 3/2011 | Alman |
| 2011/0077471 A1 | 3/2011 | King |
| 2011/0087137 A1 | 4/2011 | Hanoun |
| 2011/0124978 A1 | 5/2011 | Williams |
| 2011/0125063 A1 | 5/2011 | Shalon et al. |
| 2011/0182477 A1 | 7/2011 | Tamrakar et al. |
| 2011/0184247 A1 | 7/2011 | Contant et al. |
| 2011/0205851 A1* | 8/2011 | Harris ........................... 368/14 |
| 2011/0218407 A1 | 9/2011 | Haberman et al. |
| 2011/0276312 A1 | 11/2011 | Shalon et al. |
| 2011/0281245 A1 | 11/2011 | Mansour |
| 2011/0288379 A1 | 11/2011 | Wu |
| 2011/0318717 A1 | 12/2011 | Adamowicz |
| 2012/0004883 A1 | 1/2012 | Vock et al. |
| 2012/0015432 A1 | 1/2012 | Adler |
| 2012/0021388 A1 | 1/2012 | Arbuckle et al. |
| 2012/0031805 A1 | 2/2012 | Stolarczyk |
| 2012/0053426 A1 | 3/2012 | Webster et al. |
| 2012/0055718 A1 | 3/2012 | Chen |
| 2012/0071731 A1 | 3/2012 | Gottesman |
| 2012/0072233 A1 | 3/2012 | Hanlon et al. |
| 2012/0077154 A1 | 3/2012 | Highet et al. |
| 2012/0078071 A1 | 3/2012 | Bohm et al. |
| 2012/0083669 A1 | 4/2012 | Abujbara |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0096405 A1 | 4/2012 | Seo |
| 2012/0115111 A1 | 5/2012 | Lepine |
| 2012/0126983 A1 | 5/2012 | Breibart |
| 2012/0144912 A1 | 6/2012 | Kates et al. |
| 2012/0149996 A1 | 6/2012 | Stivoric et al. |
| 2012/0150074 A1 | 6/2012 | Yanev et al. |
| 2012/0150327 A1 | 6/2012 | Altman et al. |
| 2012/0170801 A1 | 7/2012 | De Oliveira et al. |
| 2012/0178065 A1 | 7/2012 | Naghavi et al. |
| 2012/0179020 A1 | 7/2012 | Wekell |
| 2012/0179665 A1 | 7/2012 | Baarman et al. |
| 2012/0188158 A1 | 7/2012 | Tan et al. |
| 2012/0191052 A1 | 7/2012 | Rao |
| 2012/0194418 A1 | 8/2012 | Osterhout et al. |
| 2012/0194419 A1 | 8/2012 | Osterhout et al. |
| 2012/0194420 A1 | 8/2012 | Osterhout et al. |
| 2012/0194549 A1 | 8/2012 | Osterhout et al. |
| 2012/0194550 A1 | 8/2012 | Osterhout et al. |
| 2012/0194551 A1 | 8/2012 | Osterhout et al. |
| 2012/0194552 A1 | 8/2012 | Osterhout et al. |
| 2012/0194553 A1 | 8/2012 | Osterhout et al. |
| 2012/0200488 A1 | 8/2012 | Osterhout et al. |
| 2012/0200499 A1 | 8/2012 | Osterhout et al. |
| 2012/0200601 A1 | 8/2012 | Osterhout et al. |
| 2012/0201725 A1 | 8/2012 | Imran |
| 2012/0203081 A1 | 8/2012 | Leboeuf et al. |
| 2012/0206322 A1 | 8/2012 | Osterhout et al. |
| 2012/0206323 A1 | 8/2012 | Osterhout et al. |
| 2012/0206334 A1 | 8/2012 | Osterhout et al. |
| 2012/0206335 A1 | 8/2012 | Osterhout et al. |
| 2012/0206485 A1 | 8/2012 | Osterhout et al. |
| 2012/0212398 A1 | 8/2012 | Border et al. |
| 2012/0212399 A1 | 8/2012 | Border et al. |
| 2012/0212400 A1 | 8/2012 | Border et al. |
| 2012/0212406 A1 | 8/2012 | Osterhout et al. |
| 2012/0212414 A1 | 8/2012 | Osterhout et al. |
| 2012/0214594 A1 | 8/2012 | Kirovski et al. |
| 2012/0218172 A1 | 8/2012 | Border et al. |
| 2012/0218301 A1 | 8/2012 | Miller |
| 2012/0221495 A1 | 8/2012 | Landers |
| 2012/0226471 A1 | 9/2012 | Yuen et al. |
| 2012/0226472 A1 | 9/2012 | Yuen et al. |
| 2012/0231960 A1 | 9/2012 | Osterfeld et al. |
| 2012/0235647 A1 | 9/2012 | Chung et al. |
| 2012/0235883 A1 | 9/2012 | Border et al. |
| 2012/0235885 A1 | 9/2012 | Miller et al. |
| 2012/0235886 A1 | 9/2012 | Border et al. |
| 2012/0235887 A1 | 9/2012 | Border et al. |
| 2012/0235900 A1 | 9/2012 | Border et al. |
| 2012/0236030 A1 | 9/2012 | Border et al. |
| 2012/0236031 A1 | 9/2012 | Haddick et al. |
| 2012/0239304 A1 | 9/2012 | Hayter et al. |
| 2012/0242626 A1 | 9/2012 | Hu |
| 2012/0242678 A1 | 9/2012 | Border et al. |
| 2012/0242697 A1 | 9/2012 | Border et al. |
| 2012/0242698 A1 | 9/2012 | Haddick et al. |
| 2012/0245472 A1 | 9/2012 | Rulkov et al. |
| 2012/0245714 A1 | 9/2012 | Mueller et al. |
| 2012/0245716 A1 | 9/2012 | Srinivasan et al. |
| 2012/0249797 A1 | 10/2012 | Haddick et al. |
| 2012/0251079 A1 | 10/2012 | Meschter et al. |
| 2012/0253485 A1 | 10/2012 | Weast et al. |

(56) References Cited

U.S. PATENT DOCUMENTS

| | | |
|---|---|---|
| 2012/0254749 A1 | 10/2012 | Downs et al. |
| 2012/0258433 A1 | 10/2012 | Hope et al. |
| 2012/0258804 A1 | 10/2012 | Ahmed |
| 2012/0268592 A1 | 10/2012 | Aragones et al. |
| 2012/0274508 A1 | 11/2012 | Brown et al. |
| 2012/0274554 A1 | 11/2012 | Kinoshita et al. |
| 2012/0277638 A1 | 11/2012 | Skelton et al. |
| 2012/0283855 A1 | 11/2012 | Hoffman et al. |
| 2012/0289867 A1 | 11/2012 | Kasama |
| 2012/0290109 A1 | 11/2012 | Engelberg et al. |
| 2012/0295233 A1 | 11/2012 | Cooperman |
| 2012/0302855 A1 | 11/2012 | Kamath et al. |
| 2012/0303638 A1 | 11/2012 | Bousamra et al. |
| 2012/0310971 A1 | 12/2012 | Tran |
| 2012/0313776 A1 | 12/2012 | Utter |
| 2012/0315609 A1 | 12/2012 | Miller-Kovach et al. |
| 2012/0315986 A1 | 12/2012 | Walling |
| 2012/0316406 A1 | 12/2012 | Rahman et al. |
| 2012/0316455 A1 | 12/2012 | Rahman et al. |
| 2012/0316456 A1 | 12/2012 | Rahman et al. |
| 2012/0316458 A1 | 12/2012 | Rahman et al. |
| 2012/0316471 A1 | 12/2012 | Rahman et al. |
| 2012/0316661 A1 | 12/2012 | Rahman et al. |
| 2012/0316793 A1 | 12/2012 | Jung et al. |
| 2012/0316896 A1 | 12/2012 | Rahman et al. |
| 2012/0316932 A1 | 12/2012 | Rahman et al. |
| 2012/0317167 A1 | 12/2012 | Rahman et al. |
| 2012/0317430 A1 | 12/2012 | Rahman et al. |
| 2012/0321759 A1 | 12/2012 | Marinkovich et al. |
| 2012/0323346 A1 | 12/2012 | Ashby et al. |
| 2012/0323496 A1 | 12/2012 | Burroughs et al. |
| 2012/0326863 A1 | 12/2012 | Johnson et al. |
| 2012/0326873 A1 | 12/2012 | Utter |
| 2012/0330109 A1 | 12/2012 | Tran |
| 2012/0330112 A1 | 12/2012 | Lamego et al. |
| 2012/0331201 A1 | 12/2012 | Rondel |
| 2013/0002435 A1 | 1/2013 | Utter |
| 2013/0002538 A1 | 1/2013 | Mooring et al. |
| 2013/0002545 A1 | 1/2013 | Heinrich et al. |
| 2013/0002724 A1 | 1/2013 | Heinrich et al. |
| 2013/0004923 A1 | 1/2013 | Utter |
| 2013/0005534 A1 | 1/2013 | Rosenbaum |
| 2013/0006063 A1 | 1/2013 | Wang |
| 2013/0006125 A1 | 1/2013 | Kroll et al. |
| 2013/0006583 A1 | 1/2013 | Weast et al. |
| 2013/0006802 A1 | 1/2013 | Dillahunt et al. |
| 2013/0006807 A1 | 1/2013 | Bai et al. |
| 2013/0009783 A1 | 1/2013 | Tran |
| 2013/0012788 A1 | 1/2013 | Horseman |
| 2013/0012789 A1 | 1/2013 | Horseman |
| 2013/0012790 A1 | 1/2013 | Horseman |
| 2013/0012802 A1 | 1/2013 | Horseman |
| 2013/0013331 A1 | 1/2013 | Horseman |
| 2013/0017789 A1 | 1/2013 | Chi et al. |
| 2013/0021226 A1 | 1/2013 | Bell |
| 2013/0021658 A1 | 1/2013 | Miao et al. |
| 2013/0027060 A1 | 1/2013 | Tralshawala et al. |
| 2013/0029807 A1 | 1/2013 | Amsel |
| 2013/0035563 A1 | 2/2013 | Angelides |
| 2013/0035575 A1 | 2/2013 | Mayou et al. |
| 2013/0035865 A1 | 2/2013 | Mayou et al. |
| 2013/0038056 A1 | 2/2013 | Donelan et al. |
| 2013/0041272 A1 | 2/2013 | Guillen Arredondo et al. |
| 2013/0041617 A1 | 2/2013 | Pease et al. |
| 2013/0043997 A1 | 2/2013 | Cosentino et al. |
| 2013/0044042 A1 | 2/2013 | Olsson et al. |
| 2013/0045037 A1 | 2/2013 | Schaffer |
| 2013/0045467 A1 | 2/2013 | Kamen |
| 2013/0048737 A1 | 2/2013 | Baym et al. |
| 2013/0048738 A1 | 2/2013 | Baym et al. |
| 2013/0049931 A1 | 2/2013 | Baym et al. |
| 2013/0049932 A1 | 2/2013 | Baym et al. |
| 2013/0049933 A1 | 2/2013 | Baym et al. |
| 2013/0049934 A1 | 2/2013 | Baym et al. |
| 2013/0052623 A1 | 2/2013 | Thukral et al. |
| 2013/0053655 A1 | 2/2013 | Castellanos |
| 2013/0053661 A1 | 2/2013 | Alberth et al. |
| 2013/0053990 A1 | 2/2013 | Ackland |
| 2013/0063342 A1 | 3/2013 | Chen et al. |
| 2013/0065680 A1 | 3/2013 | Zavadsky et al. |
| 2013/0069780 A1 | 3/2013 | Tran et al. |
| 2013/0069931 A1 | 3/2013 | Wilson et al. |
| 2013/0069985 A1 | 3/2013 | Wong et al. |
| 2013/0070338 A1 | 3/2013 | Gupta et al. |
| 2013/0072765 A1 | 3/2013 | Kahn et al. |
| 2013/0072807 A1 | 3/2013 | Tran |
| 2013/0073254 A1 | 3/2013 | Yuen et al. |
| 2013/0073255 A1 | 3/2013 | Yuen et al. |
| 2013/0073368 A1 | 3/2013 | Squires |
| 2013/0080113 A1 | 3/2013 | Yuen et al. |
| 2013/0083003 A1 | 4/2013 | Perez et al. |
| 2013/0083009 A1 | 4/2013 | Geisner et al. |
| 2013/0083064 A1 | 4/2013 | Geisner et al. |
| 2013/0083496 A1 | 4/2013 | Franklin et al. |
| 2013/0090565 A1 | 4/2013 | Quy |
| 2013/0091454 A1 | 4/2013 | Papa et al. |
| 2013/0095459 A1 | 4/2013 | Tran |
| 2013/0096843 A1 | 4/2013 | Yuen et al. |
| 2013/0100027 A1 | 4/2013 | Wang et al. |
| 2013/0102387 A1 | 4/2013 | Barsoum et al. |
| 2013/0103416 A1 | 4/2013 | Amigo et al. |
| 2013/0105565 A1 | 5/2013 | Kamprath |
| 2013/0106603 A1 | 5/2013 | Weast et al. |
| 2013/0106684 A1 | 5/2013 | Weast et al. |
| 2013/0107674 A1 | 5/2013 | Gossweiler et al. |
| 2013/0108993 A1 | 5/2013 | Katz |
| 2013/0109947 A1 | 5/2013 | Wood |
| 2013/0110011 A1 | 5/2013 | McGregor et al. |
| 2013/0110264 A1 | 5/2013 | Weast et al. |
| 2013/0110549 A1 | 5/2013 | Laan et al. |
| 2013/0111611 A1 | 5/2013 | Barros Almedo et al. |
| 2013/0113933 A1 | 5/2013 | Boushey et al. |
| 2013/0115583 A1 | 5/2013 | Gordon et al. |
| 2013/0115584 A1 | 5/2013 | Gordon et al. |
| 2013/0115717 A1 | 5/2013 | Guo et al. |
| 2013/0116525 A1 | 5/2013 | Heller et al. |
| 2013/0117040 A1 | 5/2013 | James et al. |
| 2013/0117041 A1 | 5/2013 | Boyce et al. |
| 2013/0117135 A1 | 5/2013 | Riddiford et al. |
| 2013/0119255 A1 | 5/2013 | Dickinson et al. |
| 2013/0127980 A1 | 5/2013 | Haddick et al. |
| 2013/0130213 A1 | 5/2013 | Burbank et al. |
| 2013/0131519 A1 | 5/2013 | LeBoeuf et al. |
| 2013/0132319 A1 | 5/2013 | Landers |
| 2013/0138230 A1 | 5/2013 | Landers |
| 2013/0141235 A1 | 6/2013 | Utter |
| 2013/0141313 A1 | 6/2013 | Zhou et al. |
| 2013/0149965 A1 | 6/2013 | Gilad-Bachrach et al. |
| 2013/0151196 A1 | 6/2013 | Yuen et al. |
| 2013/0157232 A1 | 6/2013 | Ehrenkranz |
| 2013/0158367 A1 | 6/2013 | Pacione et al. |
| 2013/0158368 A1 | 6/2013 | Pacione et al. |
| 2013/0165842 A1 | 6/2013 | Binmoeller |
| 2013/0178912 A1 | 7/2013 | Sharma |
| 2013/0183400 A1 | 7/2013 | Ioncescu |
| 2013/0184635 A1 | 7/2013 | Levy et al. |
| 2013/0187780 A1 | 7/2013 | Angelides |
| 2013/0253410 A1 | 9/2013 | Levine et al. |
| 2013/0260345 A1 | 10/2013 | Puri et al. |
| 2013/0267794 A1 | 10/2013 | Fernstrom et al. |
| 2013/0268111 A1 | 10/2013 | Dekar |
| 2013/0273506 A1 | 10/2013 | Melowsky |
| 2013/0273508 A1 | 10/2013 | Hyde et al. |
| 2013/0280681 A1 | 10/2013 | Narayan et al. |
| 2013/0282398 A1 | 10/2013 | Goldberg |
| 2013/0289466 A1 | 10/2013 | Babkes et al. |
| 2013/0289886 A1 | 10/2013 | Ricks |
| 2013/0289889 A1 | 10/2013 | Yuen et al. |
| 2013/0295531 A1 | 11/2013 | Addanki et al. |
| 2013/0296899 A1 | 11/2013 | Deem et al. |

(56) References Cited

U.S. PATENT DOCUMENTS

| | | |
|---|---|---|
| 2013/0303335 A1 | 11/2013 | Guidi et al. |
| 2013/0303869 A1 | 11/2013 | Rebec et al. |
| 2013/0306648 A1 | 11/2013 | Kemper |
| 2013/0306853 A1 | 11/2013 | Eastwood |
| 2013/0310658 A1 | 11/2013 | Ricks et al. |
| 2013/0310727 A1 | 11/2013 | Stack et al. |
| 2013/0325394 A1 | 12/2013 | Yuen et al. |
| 2013/0325396 A1 | 12/2013 | Yuen et al. |
| 2013/0325399 A1 | 12/2013 | Yuen et al. |
| 2013/0325404 A1 | 12/2013 | Yuen et al. |
| 2013/0330694 A1 | 12/2013 | Watterson |

FOREIGN PATENT DOCUMENTS

| | | |
|---|---|---|
| WO | WO 2005029242 | 6/2005 |
| WO | WO 2010070645 | 6/2010 |
| WO | WO 2012170584 | 12/2012 |

OTHER PUBLICATIONS

"TellSpec Launches Campaign for the World's First Handheld Consumer Device that Analyzes Chemicals and Allergens in Food," Toronto, Canada (PRWEB), Oct. 2, 2013.

U.S. Appl. No. 13/523,739, filed Jun. 14, 2012, Connor.

U.S. Appl. No. 13/616,238, filed Sep. 14, 2012, Connor.

* cited by examiner

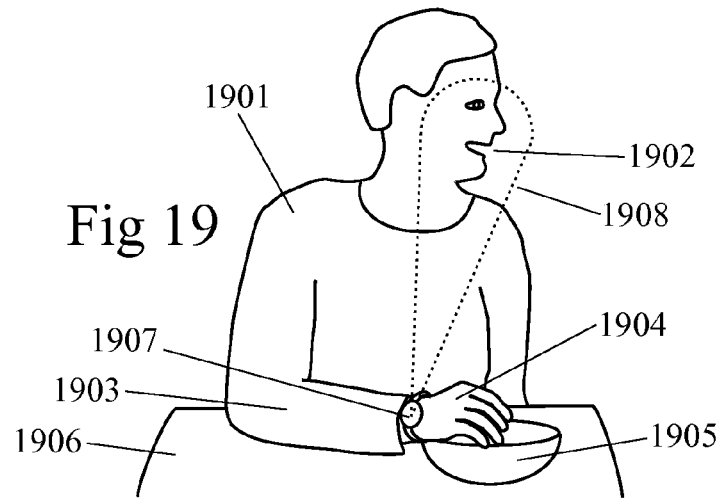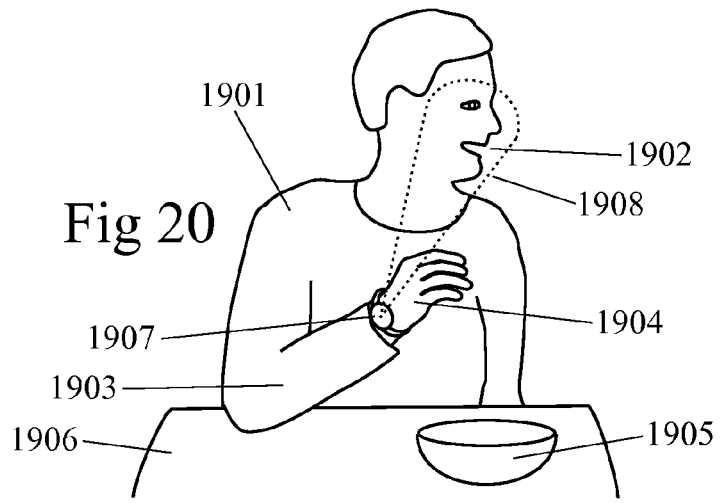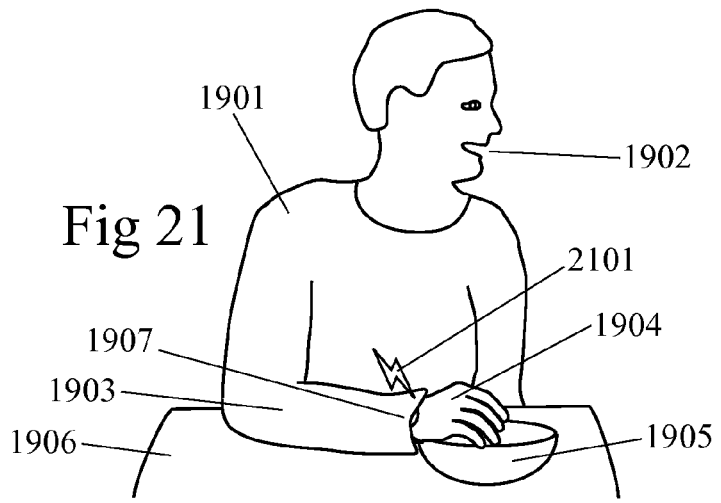

2301

2301

2301

2701

2701

WILLPOWER WATCH (TM)—A WEARABLE FOOD CONSUMPTION MONITOR

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND

Field of Invention

This invention relates to dieting, energy balance, and weight management.

Introduction to Human Energy Balance and Weight Management

The United States population has some of the highest prevalence rates of obese and overweight people in the world. Further, these rates have increased dramatically during recent decades. In the late 1990's, around one in five Americans was obese. Today, that figure has increased to around one in three. It is estimated that around one in five American children is now obese. The prevalence of Americans who are generally overweight is estimated to be as high as two out of three This increase in the prevalence of Americans who are overweight or obese has become one of the most common causes of health problems in the United States. Potential adverse health effects from obesity include: cancer (especially endometrial, breast, prostate, and colon cancers); cardiovascular disease (including heart attack and arterial sclerosis); diabetes (type 2); digestive diseases; gallbladder disease; hypertension; kidney failure; obstructive sleep apnea; orthopedic complications; osteoarthritis; respiratory problems; stroke; metabolic syndrome (including hypertension, abnormal lipid levels, and high blood sugar); impairment of quality of life in general including stigma and discrimination; and even death. There are estimated to be over a quarter-million obesity-related deaths each year in the United States. The tangible costs to American society of obesity have been estimated at over $100 billion dollars per year. This does not include the intangible costs of human pain and suffering.

Obesity is a complex disorder with multiple interacting causal factors including genetic factors, environmental factors, and behavioral factors. A person's behavioral factors include the person's caloric intake (the types and quantities of food which the person consumes) and caloric expenditure (the calories that the person burns in regular activities and exercise). Energy balance is the net difference between caloric intake and caloric expenditure. Other factors being equal, energy balance surplus (caloric intake greater than caloric expenditure) causes weight gain and energy balance deficit (caloric intake less than caloric expenditure) causes weight loss. There are many factors that contribute to obesity. Good approaches to weight management are comprehensive in nature and engage the motivation of the person managing their own weight. Management of energy balance is a key part of an overall system for weight management. The invention that will be disclosed herein comprises a novel and useful technology that engages people in energy balance management as part of an overall system for weight management.

There are two key components to managing energy balance: (1) managing caloric intake—the types and quantities of food consumed; and (2) managing caloric expenditure—the calories burned in daily activities and exercise. Both components are essential, but there have been some large-scale studies indicating that the increase in obesity in the United States has been predominantly caused by increased food consumption. People in the U.S. are now consuming large portion sizes and too many calories. Of these calories consumed, there is too much saturated fat and not enough vitamins and minerals. Many people consistently underestimate the amount of food that they eat.

These adverse eating trends are fueling the increase in obesity despite the fact that many people are really trying to eat less, eat better, and lose weight. The American Obesity Association (AOA) estimates that around 30% of Americans are actively trying to lose weight. The average American female has tried six diets. It appears that many people want to manage their food consumption, but the vast majority of these people are unsuccessful in doing so over the long term. Long-term compliance with diets is notoriously low. With all of the exposure to food and food advertisements that tempt people in today's society, it appears that many people do not have enough willpower for long-term compliance with diet planning. The novel invention that is disclosed herein can provide these people with a new and powerful tool for monitoring their food consumption and boosting their willpower to manage their energy balance and weight over the long term.

As we will discuss in depth in the following section, there have been many efforts in the prior art to create technology to successfully monitor and/or control food consumption and caloric intake. Some of these approaches involve surgical procedures or implants that reduce food consumption or limit absorption by the body of food that is consumed. Some of these approaches have been successful in reducing the calories that are ultimately absorbed by the body. However, surgical procedures tend to be invasive, expensive, have potentially-serious complications, and are not suitable for everyone who wants to lose weight. Potential adverse health effects from surgical procedures to address obesity include: blood clots, bowel or stomach obstruction, diarrhea, dumping syndrome (including bloating, cramps, and diarrhea after eating), flatulence, gallstones, hernia, hypoglycemia, infection, malnutrition (including low calcium, vitamins such as B-12, iron, protein, and thiamine), nausea, blockage of GI tract diagnostic tests, respiratory problems, stomach perforation, ulcers, and vomiting.

Due to these problems, non-surgical and non-implantable approaches are needed for monitoring and controlling food consumption and caloric intake. Accordingly, the invention that will be disclosed herein, and the accompanying review of the prior art, are focused on non-surgical non-implantable approaches to monitoring and managing food consumption and caloric intake. We do not review surgical procedures or implantable devices for addressing obesity.

We will discuss non-surgical non-implantable approaches to monitoring and managing caloric intake in the prior art in greater depth in the following section. However, as part of this introduction to this field, we now briefly introduce some of the key limitations of current non-surgical non-implantable approaches. This introduces the unmet need for better devices and methods to help people monitor and manage their food consumption and caloric intake.

The vast majority of non-surgical non-implantable approaches to monitoring and managing food consumption in the prior art rely on purely-manual (or computer-assisted manual) logging of food consumption and/or calories. For decades, this was done on paper. Now this can be done with the help of an application on a smart phone, electronic pad, or other mobile electronic device. However, even these computer-assisted devices and methods still rely on human action by the person to record what the person eats each time that they eat.

Since these food and calorie logging devices and methods depend on voluntary human action each time that a person eats anything, even a snack, they are time-consuming and often cumbersome. They are notoriously associated with delays in food recording, "caloric amnesia," errors of omission, chronic under-estimation of portion sizes, and low long-term compliance. Also, it is tough to make them tamper-resistant because their operation depends on voluntary action. People can easily "cheat" by simply not recording some food items consumed. To make matters worse, their operation is conspicuous and potentially-embarrassing in social situations such as group dining and dates. This further aggravates delays in food recording and causes low long-term compliance. The invention that will be disclosed herein overcomes these problems because it monitors and measures food consumption in an automatic, tamper-resistant, and relatively-inconspicuous manner.

In an effort to overcome these limitations of manual food and calorie logging, some approaches in the prior art measure food purchases instead. The assumption is that food purchases can be used as a proxy for food consumed. However, food purchased by an individual is a poor estimate of how much food is actually consumed by that individual when the individual buys food for other people (such as their family), when the individual does not eat all of the food purchased, when food is purchased at multiple venues using different methods, and when there is uncertainty concerning the specific time period wherein an individual eats the food. Further, approaches based on bar codes (or other food identification codes) are limited because not all food items at stores have such codes and few food items served in restaurants and homes have such codes.

Other approaches are based on meal planning with pre-packaged food portions and/or pre-specified meals. However, these meal planning approaches do not allow people much choice in food selection. This causes frustration, diet "cheating", and low long-term compliance. It is easy for people to circumvent such methods during periods of low willpower.

More recently, there have been new approaches to measuring food consumption that use cameras (or other mobile imaging devices) to take pictures of food prior to consumption. The intent is to make food logging easier. However, even these new image-based approaches in the prior art still require manual intervention to aim an imaging device toward a food source and to activate picture taking, each time the person eats. Accordingly, even these image-based approaches in the prior art depend on voluntary human action. It is difficult, or even impossible, to make them entirely automatic, tamper-resistant, and inconspicuous. Due to these limitations, such devices and methods can still lead to low long-term compliance.

There remains an unmet need for a non-invasive, automatic, tamper-resistant, and relatively-inconspicuous device and method for monitoring and measuring food consumption and caloric intake. Such a device and method is needed to serve as part of an overall system for human energy balance and weight management to help address the obesity epidemic in the United States. The novel invention that will be disclosed herein can help to meet this need. Before disclosing it, however, we first provide an in-depth review of the prior art, including categorization of the relevant prior art and discussion of the limitations of each category of this prior art.

CATEGORIZATION AND REVIEW OF THE PRIOR ART

It can be challenging to classify prior art in a particular field into discrete categories. That is the case in the field of monitoring and managing caloric intake. There are hundreds of examples of potentially-relevant prior art related to monitoring and managing caloric intake, ranging from manual food logging methods, to mobile device food-imaging applications, to eating timing modification. However, classification of the prior art into categories, even if imperfect, is an invaluable tool for reviewing the prior art, identifying its limitations, and setting the stage for discussion of the advantages of the invention that is disclosed in subsequent sections. Towards this end, I now identify 13 general categories of prior art, discuss the general limitations of prior art in each category, and list examples of prior art which appear to be best classified into each category. This categorization and discussion of the prior art helps to identify key limitations of the prior art which are corrected by the invention disclosed herein in subsequent sections.

The 13 categories of prior art that I will now discuss are as follows: (1) manual or voice-based food consumption logging, (2) manual food weighing, (3) monitoring of food purchases, (4) monitoring of hand-to-mouth proximity, (5) external monitoring of chewing or swallowing, (6) external monitoring of muscle activity, (7) external monitoring of blood flow characteristics, (8) external monitoring of stomach activity, (9) food imaging by mobile device, (10) food imaging by device worn on the body, (11) eating portion modification, (12) eating speed modification, and (13) eating frequency modification. Surgical and implantable devices and methods for addressing obesity are not included.

1. Manual or Voice-Based Food Consumption Logging

Devices and methods for measuring caloric intake in this category depend on manual (or voice-based) intervention by a person to record food consumed each time that the person eats. In this category, basic "calorie counting" and "diet log" methods have been around in paper form for several decades. More recently, various types of computer support (including mobile device applications) have been developed in an effort to make such manual food consumption logging easier. However, even these new computer applications remain dependent on the motivation and compliance of the person to take the manual actions that are required to record food consumed each time that the person eats. Long-term compliance with manual food logging devices and methods is notoriously low. Also, people tend to under-estimate calories consumed, especially for unstructured snacking behavior.

The limitations of devices and methods for measuring caloric intake that depend on manual (or voice-based) logging of food consumption include the following. First, they depend on voluntary human action each time that a person eats anything, even a snack. This makes such devices and methods time-consuming and often cumbersome. This leads to delays in food recording, "caloric amnesia" and errors of omission, chronic under-estimation of portion sizes, and low long-term compliance. Also, devices and methods that depend on voluntary human action are difficult to make tamper-resistant. It is easy for people to "cheat" with such methods by simply not recording all food items consumed. Further, a device or method whose operation is conspicuous can be embarrassing in social situations such as group meals and social dates. This causes delays in food recording, frustration, and low long-term compliance. Finally, with respect to devices and methods which use bar codes (or other codes) to facilitate food logging, not all food items at stores have such codes and few food items served in restaurants and homes have such codes.

The many devices and methods for measuring caloric intake in the prior art that appear to be based on manual or voice-based food consumption logging include: U.S. Pat. No. 4,100,401 (Tutt et al., Jul. 11, 1978, "Calorie Calculator-Chronometer"); U.S. Pat. No. 4,212,079 (Segar et al., Jul. 8, 1980, "Electronic Calorie Counter"); U.S. Pat. No. 4,221,959 (Sessler, Sep. 9, 1980, "Checking Device for Checking the Food Intake"); U.S. Pat. No. 4,310,316 (Thomann, Jan. 12, 1982, "Diet Control Apparatus"); U.S. Pat. No. 4,321,674 (Krames et al., Mar. 23, 1982, "Nutritional Value Accumulating and Display Device"); U.S. Pat. No. 4,650,218 (Hawke, Mar. 17, 1987, "Method and Apparatus for Controlling Caloric Intake"); U.S. Pat. No. 4,686,624 (Blum et al., Aug. 11, 1987, "Portable Apparatus for Acquiring and Processing Data Relative to the Dietetics and/or the Health of a Person"); U.S. Pat. No. 4,796,182 (Duboff, Jan. 3, 1989, "Diet Monitor and Display Device"); U.S. Pat. No. 4,951,197 (Mellinger, Aug. 21, 1990, "Weight Loss Management System"); U.S. Pat. No. 5,173,588 (Harrah, Dec. 22, 1992, "Food Consumption Monitor"); U.S. Pat. No. 5,478,989 (Shepley, Dec. 26, 1995, "Nutritional Information System for Shoppers"); U.S. Pat. No. 5,542,420 (Goldman et al., Aug. 6, 1996, "Personalized Method and System for Storage, Communication, Analysis, and Processing of Health-Related Data"); U.S. Pat. No. 5,673,691 (Abrams et al., Oct. 7, 1997, "Apparatus to Control Diet and Weight Using Human Behavior Modification Techniques"); U.S. Pat. No. 5,691,927 (Gump, Nov. 25, 1997, "Nutritional Aid and Method"); U.S. Pat. No. 5,704,350 (Williams, Jan. 6, 1998, "Nutritional Microcomputer and Method") and U.S. Pat. No. 5,729,479 (Golan, Mar. 17, 1998, "Multifunctional Diet Calculator").

U.S. patents that appear to be classified in this category also include: U.S. Pat. No. 5,836,312 (Moore, Nov. 17, 1998, "Computer-Assisted System and Method for Adjudging the Effect of Consumable Intakes on Physiological Parameters"); U.S. Pat. No. 5,839,901 (Karkanen, Nov. 24, 1998, "Integrated Weight Loss Control Method"); U.S. Pat. No. 5,841,115 (Shepley, Nov. 24, 1998, "Nutritional Information System for Shoppers"); U.S. Pat. No. 5,890,128 (Diaz et al., Mar. 30, 1999, "Personalized Hand Held Calorie Computer (ECC)"); U.S. Pat. No. 5,989,188 (Birkhoelzer et al., Nov. 23, 1999, "Method and Apparatus for Determining the Energy Balance of a Living Subject on the Basis of Energy Used and Nutrition Intake"); U.S. Pat. No. 6,024,281 (Shepley, Feb. 15, 2000, "Nutritional Information System for Shoppers"); U.S. Pat. No. 6,032,676 (Moore, Mar. 7, 2000, "Method for Correlating Consumable Intakes with Physiological Parameters"); U.S. Pat. No. 6,040,531 (Miller-Kovach et al., Mar. 21, 2000, "Process for Controlling Body Weight"); U.S. Pat. No. 6,083,006 (Coffman, Jul. 4, 2000, "Personalized Nutrition Planning"); U.S. Pat. No. 6,095,949 (Arai, Aug. 1, 2000, "Health Management Device"); U.S. Pat. No. 6,336,136 (Harris, Jan. 1, 2002, "Internet Weight Reduction System"); U.S. Pat. No. 6,341,295 (Stotler, Jan. 22, 2002, "Virtual Reality Integrated Caloric Tabulator"); U.S. Pat. No. 6,478,736 (Mault, Nov. 12, 2002, "Integrated Calorie Management System"); U.S. Pat. No. 6,506,152 (Lackey et al., Jan. 14, 2003, "Caloric Energy Balance Monitor"); U.S. Pat. No. 6,553,386 (Alabaster, Apr. 22, 2003, "System and Method for Computerized Visual Diet Behavior Analysis and Training"); U.S. Pat. No. 6,571,200 (Mault, May 27, 2003, "Monitoring Caloric Expenditure Resulting from Body Activity"); U.S. Pat. No. 6,595,929 (Stivoric et al., Jul. 22, 2003, "System for Monitoring Health Wellness and Fitness Having a Method and Apparatus for Improved Measurement of Heat Flow"); and U.S. Pat. No. 6,605,038 (Teller et al., Aug. 12, 2003, "System for Monitoring Health Wellness and Fitness").

U.S. patents that appear to be classified in this category also include: U.S. Pat. No. 6,635,015 (Sagel, Oct. 21, 2003, "Body Weight Management System"); U.S. Pat. No. 6,675,041 (Dickinson, Jan. 6, 2004, "Electronic Apparatus and Method for Monitoring Net Calorie Intake"); U.S. Pat. No. 6,694,182 (Yamazaki et al., Feb. 17, 2004, "Wearable Calorie Calculator"); U.S. Pat. No. 6,745,214 (Inoue et al., Jun. 1, 2004, "Calorie Control Apparatus with Voice Recognition"); U.S. Pat. No. 6,856,938 (Kurtz, Feb. 15, 2005, "Weight Monitoring Computer"); U.S. Pat. No. 6,878,885 (Miller-Kovach et al., Apr. 12, 2005, "Process for Controlling Body Weight"); U.S. Pat. No. 6,917,897 (Mork, Jul. 12, 2005, "Food and Exercise Calculator"); U.S. Pat. No. 7,020,508 (Stivoric et al., Mar. 28, 2006, "Apparatus for Detecting Human Physiological and Contextual Information"); U.S. Pat. No. 7,261,690 (Teller et al., Aug. 28, 2007, "Apparatus for Monitoring Health, Wellness and Fitness"); U.S. Pat. No. 7,285,090 (Stivoric et al., Oct. 23, 2007, "Apparatus for Detecting, Receiving, Deriving and Displaying Human Physiological and Contextual Information"); U.S. Pat. No. 7,361,141 (Nissila et al., Apr. 22, 2008, "Method and Device for Weight Management of Humans"); U.S. Pat. No. 7,500,937 (Hercules, Mar. 10, 2009, "Diet Compliance System"); U.S. Pat. No. 7,857,730 (Dugan, Dec. 28, 2010, "Methods and Apparatus for Monitoring and Encouraging Health and Fitness"); U.S. Pat. No. 7,949,506 (Hill et al., May 24, 2011, "Method for Determining and Compensating for a Weight Loss Energy Gap"); U.S. Pat. No. 7,959,567 (Stivoric et al., Jun. 14, 2011, "Device to Enable Quick Entry of Caloric Content"); U.S. Pat. No. 8,073,707 (Teller et al., Dec. 6, 2011, "System for Detecting Monitoring and Reporting an Individual's Physiological or Contextual Status"); U.S. Pat. No. 8,075,451 (Dugan, Dec. 13, 2011, "Methods and Apparatus for Monitoring and Encouraging Health and Fitness"); U.S. Pat. No. 8,087,937 (Peplinski et al., Jan. 3, 2012, "System and Method for Monitoring Weight and Nutrition"); and U.S. Pat. No. 8,157,731 (Teller et al., Apr. 17, 2012, "Method and Apparatus for Auto Journaling of Continuous or Discrete Body States Utilizing Physiological and/or Contextual Parameters").

U.S. patent applications that appear to be classified in this category include: 20010049470 (Mault et al., Dec. 6, 2001, "Diet and Activity Monitoring Device"); 20020062069 (Mault, May 23, 2002, "System and Method of Integrated Calorie Management Using Interactive Television"); 20020133378 (Mault et al., Sep. 19, 2002, "System and Method of Integrated Calorie Management"); 20020156351 (Sagel, Oct. 24, 2002, "Body Weight Management System"); 20030065257 (Mault et al., Apr. 3, 2003, "Diet and Activity Monitoring Device"); 20030152607 (Mault, Aug. 14, 2003, "Caloric Management System and Method with Voice Recognition"); 20030165799 (Bisogno, Sep. 4, 2003, "Computer Program, Method, and System for Monitoring Nutrition Content of Consumables and for Facilitating Menu Planning"); 20030219513 (Gordon, Nov. 27, 2003, "Personal Nutrition Control Method"); 20040034289 (Teller et al., Feb. 19, 2004, "System for Monitoring Health, Wellness and Fitness"); 20040133081 (Teller et al., Jul. 8, 2004, "Method and Apparatus for Auto Journaling of Continuous or Discrete Body States Utilizing Physiological and/or Contextual Parameters"); 20040152957 (Stivoric et al., Aug. 5, 2004, "Apparatus for Detecting, Receiving, Deriving and Displaying Human Physiological and Contextual Information"); 20050004436 (Nissila et al., Jan. 6, 2005, "Method and Device for Weight Management of Humans"); 20050008994 (Bisogno, Jan. 13, 2005, "Computer Program, Method, and System for Monitoring Nutrition Content of Consumables and for Facilitating Menu Planning"); 20050113650 (Pacione et al., May 26, 2005, "System for Monitoring and Managing Body Weight and Other Physiological Conditions Including Iterative and Personalized Planning Intervention and Reporting Capability"); 20050247213 (Slilaty, Nov. 10, 2005, "Method of Identifying Particular Attributes of Food Products Consistent with Consumer Needs and/or Desires"); 20050266385 (Bisogno, Dec. 1, 2005, "Computer Program, Method, and System for Monitoring Nutrition Content of Consumables and for Facilitating Menu Planning"); 20060031102 (Teller et al., Feb. 9, 2006, "System for Detecting Monitoring and Reporting an Individual's Physiological or Contextual Status"); 20060036395 (Shaya et al., Feb. 16, 2006, "Method and Apparatus for Measuring and Controlling Food Intake of an Individual"); 20060074716 (Tilles et al., Apr. 6, 2006, "System and Method for Providing Customized Interactive and Flexible Nutritional Counseling"); 20060122474 (Teller et al., Jun. 8, 2006, "Apparatus for Monitoring Health Wellness and Fitness"); and 20060264730 (Stivoric et al., Nov. 23, 2006, "Apparatus for Detecting Human Physiological and Contextual Information").

U.S. patent applications that appear to be classified in this category also include: 20070027366 (Osburn Dec. 1, 2007, "Device and System for Entering and Monitoring Dietary Data"); 20070089335 (Smith et al., Apr. 26, 2007, "Nutrient Consumption/Expenditure Planning and Tracking Apparatus System and Method"); 20070106129 (Srivathsa et al., May 10, 2007, "Dietary Monitoring System for Comprehensive Patient Management"); 20070179355 (Rosen, Aug. 2, 2007, "Mobile Self-Management Compliance and Notification Method, System and Computer Program Product"); 20070208593 (Hercules, Sep. 6, 2007, "Diet Compliance System"); 20080167538 (Teller et al., Jul. 10, 2008, "Method and Apparatus for Auto Journaling of Body States and Providing Derived Physiological States Utilizing Physiological and/or Contextual Parameter"); 20080167539 (Teller et al., Jul. 10, 2008, "Method and Apparatus for Auto Journaling of Body States and Providing Derived Physiological States Utilizing Physiological and/or Contextual Parameter"); 20080171920 (Teller et al., Jul. 17, 2008, "Method and Apparatus for Auto Journaling of Body States and Providing Derived Physiological States Utilizing Physiological and/or Contextual Parameter"); 20080171921 (Teller et al., Jul. 17, 2008, "Method and Apparatus for Auto Journaling of Body States and Providing Derived Physiological States Utilizing Physiological and/or Contextual Parameter"); 20080171922 (Teller et al., Jul. 17, 2008, "Method and Apparatus for Auto Journaling of Body States and Providing Derived Physiological States Utilizing Physiological and/or Contextual Parameter"); 20080275309 (Stivoric et al., Nov. 6, 2008, "Input Output Device for Use with Body Monitor"); 20100057564 (Godsey et al., Mar. 4, 2010, "System and Method for Fitness Motivation"); 20100062119 (Miller-Kovach et al., Mar. 11, 2010, "Processes and Systems for Achieving and Assisting in Improved Nutrition"); 20100062402 (Miller-Kovach et al., Mar. 11, 2010, "Processes and Systems Using and Producing Food Healthfulness Data Based on Linear Combinations of Nutrients"); 20100080875 (Miller-Kovach et al., Apr. 1, 2010, "Processes and Systems for Achieving and Assisting in Improved Nutrition Based on Food Energy Data and Relative Healthfulness Data"); 20100228160 (Schweizer, Sep. 9, 2010, "Apparatus for Activity Monitoring"); 20110087137 (Hanoun, Apr. 14, 2011, "Mobile Fitness and Personal Caloric Management System"); 20120031805 (Stolarczyk, Feb. 9, 2012, "Daily Meal Planning System"); 20120072233 (Hanlon et al., Mar. 22, 2012, "Medical Health Information System for Health Assessment, Weight Management and Meal Planning"); 20120083669 (Abujbara, Apr. 5, 2012, "Personal Nutrition and Wellness Advisor"); and 20120096405 (Seo, Apr. 19, 2012, "Apparatus and Method for Diet Management").

2. Manual Food Weighing

Devices and methods for measuring caloric intake in this category require that a person weighs food before it is consumed. Generally, these devices and methods use some type of stand-alone food scale or weight-measuring utensil to estimate the weight of food that is consumed. Although some of these devices and methods seek to make this weighing process as easy as possible (e.g. by incorporating a scale into a utensil), they all require use of specialized equipment and human intervention each time that a person eats. These devices and methods have some of the same compliance problems that plague basic food logging methods. Will a person really weigh each bit of food on which they snack throughout the day? Also, even with perfect compliance, while weight-based devices can be useful for estimating the quantities of food consumed, they are not very useful for identifying the types of food consumed. Accordingly, devices and methods in this category, like basic food logging methods, generally rely on human intervention for food identification.

The limitations of devices and methods for measuring caloric intake that are based on scales and manual food weighing include the following. Such devices and methods depend on voluntary human action, at least for food identification, each time that a person eats. This makes them time-consuming and results in low long-term compliance. People can easily circumvent devices and methods that depend on voluntary human action. They are tough to make tamper-resistant. Also, devices and methods for measuring caloric intake whose operation is conspicuous when a person eats are embarrassing in social situations such as group meals and social dates. With respect to those devices and methods that rely on bar codes for food identification, not all food items at stores have such codes and few food items served in restaurants and homes have such codes. Finally, for those devices and methods in this category that have a fixed eating location with special food-weighing equipment, these devices and methods are constraining, anti-social, easy-to-circumvent, and lead to low long-term compliance.

Devices and methods for measuring caloric intake in the prior art that appear to be based on manual food weighing include: U.S. Pat. No. 4,387,777 (Ash, Jun. 14, 1983, "Calorie Counting Method and Apparatus"); U.S. Pat. No. 4,875,533 (Mihara et al., Oct. 24, 1989, "Automatic Weight Detecting Device"); U.S. Pat. No. 4,911,256 (Attikiouzel, Mar. 27, 1990, "Dietetic Measurement Apparatus"); U.S. Pat. No. 5,033,561 (Hettinger, Jul. 23, 1991, "Diet Control Device"); U.S. Pat. No. 5,233,520 (Kretsch et al., Aug. 3, 1993, "Method and System for Measurement of Intake of Foods, Nutrients and Other Food Components in the Diet"); U.S. Pat. No. 5,388,043 (Hettinger, Feb. 7, 1995, "Diet and Behavioral Control Device"); U.S. Pat. No. 5,817,006 (Bergh et al., Oct. 6, 1998, "Method and Apparatus for Measurement of Eating Speed"); and U.S. Pat. No. 6,425,862 (Brown, Jul. 30, 2002, "Interactive Furniture for Dieters").

U.S. patent applications that appear to be classified in this category include: 20020124017 (Mault, Sep. 5, 2002, "Personal Digital Assistant with Food Scale Accessory"); 20060263750 (Gordon, Nov. 23, 2006, "Personal Nutrition Control Devices"); 20070028453 (Crow, Feb. 8, 2007, "Portion Control Serving Utensils"); 20070050058 (Zuziak et al., Mar. 1, 2007, "Placemat for Calculating and Monitoring Calorie Intake"); 20070173703 (Lee et al., Jul. 26, 2007, "Method, Apparatus, and Medium for Managing Weight by Using Calorie Consumption Information"); 20080276461 (Gold, Nov. 13, 2008, "Eating Utensil Capable of Automatic Bite Counting"); 20110184247 (Contant et al., Jul. 28, 2011, "Comprehensive Management of Human Health"); and 20120055718 (Chen, Mar. 8, 2012, "Electronic Scale for Recording Health Administration Data").

3. Monitoring of Food Purchases

Devices and methods for measuring caloric intake in this category are based on monitoring which food items a person purchases. One advantage of this approach is that it can be more automatic and less dependent on manual intervention than devices and methods in previous categories. Another advantage of such devices and methods is that it is relatively easy to track food purchase transactions, at least at a given store. Itemized purchase transactions are often already recorded (e.g. by bar code scanning) for payment purposes.

However, there are several limitations with using food purchased by an individual as a proxy for food consumed by that individual. First, people purchase food at multiple locations with multiple methods, including cash. It can be very difficult to collect and combine information concerning food purchases from various locations. Also, people do not always eat all the food that they purchase and do not always purchase all the food that they eat. Many people shop for their entire family. Some purchased food may be thrown out. Also, other family members may purchase food or food may be provided by non-family members as hospitality or gifts. Finally, it can be tough trying to estimate food consumption for a specific time period based on food purchased because food purchased may be eaten before or after a specific time period.

Devices and methods for measuring caloric intake in the prior art that appear to be based on monitoring food purchases include: U.S. Pat. No. 5,412,564 (Ecer, May 2, 1995, "System and Method for Diet Control") and U.S. Pat. No. 7,769,635 (Simons-Nikolova et al., Aug. 3, 2010, "Weight Management System with Simple Data Input"); as well as U.S. Patent Applications 20080255955 (Simons-Nikolova et al., Oct. 16, 2008, "Weight Management System with Simple Data Input") and 20100205209 (Jokinen, Aug. 12, 2010, "Method and System for Monitoring a Personal Intake").

4. Monitoring of Hand-to-Mouth Proximity

Devices and methods for measuring caloric intake in this category involve monitoring hand-to-mouth movements and hand-to-mouth proximity. One example of such a device and method is a wrist-mounted accelerometer that detects hand movements that are generally associated with bringing food to a person's mouth. One advantage of such a device is that its recording and analysis of hand movements can be relatively automatic. Another advantage of such a device is that it can be relatively inconspicuous and thus not embarrassing for use in social eating situations.

However, there are significant limitations to devices and methods in this category. First, such devices and methods do not provide good information concerning the types of food consumed. In this respect, they generally rely on the same manual food identification methods that are used in basic food logging approaches. Second, although progress has been made to differentiate hand motions indicating food consumption from other types of hand motions (such as covering one's mouth or brushing one's teeth), there remains imprecision with respect to quantification of food consumed based on analysis of hand-to-mouth movements or hand-to-mouth proximity. Third, it is tough to make such devices and methods tamper-resistant. A person can use non-conventional hand movements to eat, use a non-monitored hand to eat, eat larger bite sizes with each hand movement, use alternative utensils to bring food to their mouth, or find other creative ways to bring food to their mouth that are not recognized as food consumption by such a device.

Devices and methods for measuring caloric intake in the prior art that appear to monitor hand-to-mouth motions and/or proximity include: U.S. Pat. No. 3,885,576 (Symmes, May 27, 1975, "Wrist Band Including a Mercury Switch to Induce an Electric Shock"); U.S. Pat. No. 4,218,611 (Cannon, Aug. 19, 1980, "Method and Apparatus for Controlling Eating Behavior"); U.S. Pat. No. 4,965,553 (DelBiondo et al., Oct. 23, 1990, "Hand-Near-Mouth Warning Device"); U.S. Pat. No. 5,299,356 (Maxwell, Apr. 5, 1994, "Diet Eating Utensil"); and U.S. Pat. No. 8,112,281 (Yeung et al., Feb. 7, 2012, "Accelerometer-Based Control of Wearable Audio Recorders"); as well as U.S. Patent Applications 20060197670 (Breibart, Sep. 7, 2006, "Method and Associated Device for Personal Weight Control"); 20070098856 (LePine, May 3, 2007, "Mealtime Eating Regulation Device"); 20080276461 (Gold, Nov. 13, 2008, "Eating Utensil Capable of Automatic Bite Counting"); 20100194573 (Hoover et al., Aug. 5, 2010, "Weight Control Device"); 20100240962 (Contant, Sep. 23, 2010, "Eating Utensil to Monitor and Regulate Dietary Intake"); and 20120126983 (Breibart, May 24, 2012, "Method and Associated Device for Personal Weight Control or Weight Loss").

5. External Monitoring of Chewing or Swallowing

Devices and methods for measuring caloric intake in this category involve external monitoring of chewing and/or swallowing. In various examples, these devices and methods monitor chewing and/or swallowing by analyzing chewing or swallowing sounds or movements. Like monitoring devices and methods in preceding categories, devices and methods in this category can operate in a relatively automatic manner in order to detect general eating activity and give a rough indication of the quantity of food consumed.

However, devices and methods in this category share many of the limitations of hand-to-mouth monitoring in the previous category. First, such devices and methods do not provide much information concerning what types of foods or beverages are being consumed. In this respect, they again rely on manual food identification methods, with all of their associated compliance problems. Also, it can be tough to quantify the amount of food consumed based on the number of chewing or swallowing motions. Different people chew their food to different extents and ingest different amounts of food per swallow. Finally, such devices and methods can be circumvented. A person can chew or swallow in an unusual manner (to confuse or circumvent the device) or can put a generally-solid food in a blender for consumption as a liquid (to confuse or circumvent the device).

Devices and methods for measuring caloric intake in the prior art based on monitoring chewing and/or swallowing sounds or movements include: U.S. Pat. No. 5,263,491 (Thornton, Nov. 23, 1993, "Ambulatory Metabolic Monitor"); U.S. Pat. No. 6,135,950 (Adams, Oct. 24, 2000, "E-Fit Monitor"); U.S. Pat. No. 6,425,862 (Brown, Jul. 30, 2002, "Interactive Furniture for Dieters"); and U.S. Pat. No. 7,914, 468 (Shalon et al., Mar. 29, 2011, "Systems and Methods for Monitoring and Modifying Behavior"); as well as U.S. Patent applications: 20050283096 (Chau et al., Dec. 22, 2005, "Apparatus and Method for Detecting Swallowing Activity"); 20060064037 (Shalon et al., Mar. 23, 2006, "Systems and Methods for Monitoring and Modifying Behavior"); 20070098856 (LePine, May 3, 2007, "Mealtime Eating Regulation Device"); 20100240962 (Contant, Sep. 23, 2010, "Eating Utensil to Monitor and Regulate Dietary Intake"); 20110125063 (Shalon et al., May 26, 2011, "Systems and Methods for Monitoring and Modifying Behavior"); and 20110276312 (Shalon et al., Nov. 10, 2011, "Device for Monitoring and Modifying Eating Behavior").

6. External Monitoring of Muscle Activity

Devices and methods for measuring caloric intake in this category involve external monitoring of muscle activity (especially electromagnetic signals from muscle activity) which indicates probable food consumption. The pros and cons of such devices and methods are similar to those that monitor chewing and swallowing. Devices and methods in this category are relatively automatic and can detect signals that indicate probable food consumption, but they are limited for measuring the quantities of food consumed and are very limited for identifying the types of food consumed. Devices and methods for measuring caloric intake in the prior art based on monitoring (electromagnetic) muscle activity include: U.S. Pat. No. 4,355,645 (Mitani et al., Oct. 26, 1982, "Device for Displaying Masticatory Muscle Activities") and U.S. Pat. No. 7,914,468 (Shalon et al., Mar. 29, 2011, "Systems and Methods for Monitoring and Modifying Behavior") as well as U.S. Patent Application 20080262557 (Brown, Oct. 23, 2008, "Obesity Management System").

7. External Monitoring of Blood Flow Characteristics

Devices and methods for measuring caloric intake in this category involve external monitoring of blood flow characteristics which indicate probable food consumption. Examples of blood flow characteristics include greater flow through tissue that is associated with food consumption. The pros and cons of these devices and methods are similar to those in previous categories that monitor chewing, swallowing, and muscle activity. Devices and methods in this category can be automatic and detect likely food consumption, but are limited for measuring the quantities of food consumed and very limited for identifying the types of food consumed. Devices and methods for measuring caloric intake in the prior art based on monitoring blood flow characteristics include: U.S. Pat. No. 5,398,688 (Laniado, Mar. 21, 1995, "Method, System and Instrument for Monitoring Food Intake"); U.S. Pat. No. 6,893,406 (Takeuchi et al., May 17, 2005, "Mastication Monitoring Device"); and U.S. Pat. No. 7,914,468 (Shalon et al., Mar. 29, 2011, "Systems and Methods for Monitoring and Modifying Behavior"); as well as U.S. Patent Application 20040073142 (Takeuchi et al., Apr. 15, 2004, "Mastication Monitoring Device").

8. External Monitoring of Stomach Activity

Devices and methods for measuring caloric intake in this category involve external monitoring of stomach activity which indicates probable food consumption. Devices and methods in this category are relatively automatic and detect signals that indicate probable food consumption, but they are not precise for measuring the types and quantities of food consumed as a means to estimate caloric intake. Devices and methods for measuring caloric intake in the prior art based on monitoring stomach activity include: U.S. Pat. No. 4,823,808 (Clegg et al., Apr. 25, 1989, "Method for Control of Obesity, Overweight and Eating Disorders") and U.S. Pat. No. 5,301,679 (Taylor, Apr. 12, 1994, "Method and System for Analysis of Body Sounds").

9. Food Imaging by Mobile Device

Devices and methods in this category estimate caloric intake based on analysis of pictures of food taken by a mobile imaging device, such as a camera, mobile/smart phone, or electronic tablet. For classification purposes, we have differentiated between freestanding mobile food-imaging devices that are not worn on a person's body (included in this category) versus wearable food-imaging devices that are worn on a person's body (included in the next category). This distinction is important with respect to: imaging directionality, imaging field of vision, and which objects are within the imaging field of vision; estimation accuracy for the types and quantities of food actually consumed; and image-taking automation, tamper-resistance, and compliance.

Devices and methods that take pictures of food and automatically analyze these pictures in order to identify foods to estimate caloric intake can be superior to devices and methods in prior categories in some respects. However, there remain several limitations to devices and methods that estimate caloric intake using freestanding mobile imaging devices. First, such mobile devices and methods for measuring caloric intake require a person to manually aim an imaging device each time that a person eats. This is time-consuming (having to aim the field of vision), easy to circumvent (just don't use it for some food consumed), and potentially embarrassing in social dining situations. This can lead to low long-term compliance. Also, mobile devices and methods for measuring caloric intake require a person to manually activate picture taking each time that a person eats anything. This makes such devices and methods easy to circumvent (just don't "click the button"), easy to forget (especially for unstructured snacking), and potentially embarrassing in social dining situations. This also leads to low long-term compliance. Even devices and methods in this category that have automated image analysis still depend on human intervention to aim and activate them. Any approach that depends on voluntary human action each time that a person eats anything is difficult to make tamper-resistant. It is very easy for someone to "cheat" by simply not taking pictures of some consumed food items.

Devices and methods for measuring caloric intake in the prior art that appear to be based on food imaging by a mobile device include: U.S. Pat. No. 5,819,735 (Mansfield et al., Oct. 13, 1998, "Device and Method for Monitoring Dietary Intake of Calories and Nutrients") and U.S. Pat. No. 6,283,914 (Mansfield et al., Sep. 4, 2001, "Device and Method for Monitoring Dietary Intake of Calories and Nutrients"); as well as U.S. Patent Applications 20020027164 (Mault et al., Mar. 7, 2002, "Portable Computing Apparatus Particularly Useful in a Weight Management Program"); 20030076983 (Cox, Apr. 24, 2003, "Personal Food Analyzer"); 20030163354 (Shamoun, Aug. 28, 2003, "Device for Collecting and Analyzing Nutritional Data and Method Therefor"); 20060189853 (Brown, Aug. 24, 2006, "Method and System for Improving Adherence with a Diet Program or Other Medical Regimen"); 20060229504 (Johnson, Oct. 12, 2006, "Methods and Systems for Lifestyle Management"); 20070030339 (Findlay et al., Feb. 8, 2007, "Method, System and Software for Monitoring Compliance"); 20070059672 (Shaw, Mar. 15, 2007, "Nutrition Tracking Systems and Methods"); 20080267444 (Simons-Nikolova et al., Oct. 30, 2008, "Modifying a Person's Eating and Activity Habits"); 20090112800 (Athsani, 4/30/200, "System and Method for Visual Contextual Search"); 20090176526 (Altman, Jul. 9, 2009, "Longitudinal Personal Health Management System Using Mobile Data Capture"); 20090219159 (Morgenstern, Sep. 3, 2009, "Method and System for an Electronic Personal Trainer"); 20100111383 (Boushey et al., May 6, 2010, "Dietary Assessment System and Method"); 20100173269 (Puri et al., Jul. 8, 2010, "Food Recognition Using Visual Analysis and Speech Recognition"); 20100332571 (Healey et al., Dec. 30, 2010, "Device Augmented Food Identification"); 20110182477 (Tamrakar et al., Jul. 28, 2011, "Method for Computing Food Volume in a Method for Analyzing Food"); 20110184247 (Contant et al., Jul. 28, 2011, "Comprehensive Management of Human Health"); 20110318717 (Adamowicz, Dec. 29, 2011, "Personalized Food Identification and Nutrition Guidance System"); and 20120055718 (Chen, Mar. 8, 2012, "Electronic Scale for Recording Health Administration Data").

10. Food Imaging by Device Worn on the Body

Devices and methods in this category estimate caloric intake by analyzing pictures of food taken from a mobile imaging device that is actually worn on a person's body. The food-imaging aspect of devices and methods in this category provides superior food identification to non-image-based devices and methods (all of the prior categories except the preceding one for mobile imaging devices). As an advantage over freestanding mobile imaging devices, the wearable nature of devices and methods in this category enables a higher degree of automation and tamper-resistance than that which is possible with mobile devices. Prior art in this category has not taken advantage of using the wearable nature of such devices and methods to create tamper-resistant features, such as the features in this present invention which we will disclose in later sections.

Although there are potential advantages of devices and methods that use wearable imaging members to estimate caloric intake, the prior art in this category does not take full advantage of them. There are several limitations to devices and methods disclosed in the prior art in this category that are overcome by the invention that will be disclosed herein in later sections. These limitations include the following. Some of the devices and methods in the prior art are very conspicuous. For example, one requires a person to wear a video camera on the top of their head while eating. This would be very embarrassing for use in social dining situations. Further, it appears that wearable imaging devices in the prior art only analyze potential food sources. This is useful for identification of the types of food to which the person may have access, but is limited for estimating how much of these potential food sources the person actually consumes. This is particularly problematic in grocery stores or group dining situations wherein a person eats only a small fraction of all the potential food sources that come into the field of vision of a wearable imaging member. Finally, the operation of imaging members can be compromised by tampering. The person may obstruct the camera or direct its field of vision away from a food source. Prior art does not fully address this problem. The invention which will be disclosed herein overcomes all of these limitations of the prior art in this category.

Devices and methods for measuring caloric intake in the prior art that appear to be based on wearable imaging members include: U.S. Pat. No. 6,508,762 (Karnieli, Jan. 21, 2003, "Method for Monitoring Food Intake") and U.S. Pat. No. 6,513,532 (Mault et al., Feb. 4, 2003, "Diet and Activity-Monitoring Device"); as well as U.S. Patent Applications 20010049470 (Mault et al., Dec. 6, 2001, "Diet and Activity Monitoring Device"); 20020022774 (Karnieli, Feb. 21, 2002, "Method for Monitoring Food Intake"); 20020047867 (Mault et al., Apr. 25, 2002, "Image Based Diet Logging"); 20020109600 (Mault et al., Aug. 15, 2002, "Body Supported Activity and Condition Monitor"); 20030208110 (Mault et al., Nov. 6, 2003, "Physiological Monitoring Using Wrist-Mounted Device"); 20090012433 (Fernstrom et al., Jan. 8, 2009, "Method, Apparatus and System for Food Intake and Physical Activity Assessment"); and 20100049004 (Edman et al., Feb. 25, 2010, "Metabolic Energy Monitoring System").

11. Eating Portion Modification

Devices and methods in this category are generally used for modification of food consumption, but not measurement of food consumption. However, I have included them and this category in this review of the prior art because the technology is nonetheless generally relevant to the invention disclosed herein. Devices and methods in this category use standard-size food containers or standard-capacity serving utensils in an effort to standardize and reduce the portion sizes of food consumed. Regardless of whether such devices and methods are used for modification of food consumption or measurement of food consumption, they all depend on voluntary human action for their operation. Food must be stored or served using the standard-size tools. These devices and methods are not useful for food identification and are not tamper-resistant. A person can easily consume food without using the standard-size tools.

Devices and methods in the prior art that appear to be based on eating portion modification include: U.S. Pat. No. 7,044,739 (Matson, May 16, 2006, "System for Controlled Nutrition Consumption") and U.S. Patent Applications 20050014111 (Matson, Jan. 20, 2005, "System for Controlled Nutrition Consumption") and 20100125181 (Hyde et al., May 20, 2010, "Food Content Detector").

12. Eating Speed Modification

Devices and methods in this category are generally used for modification of food consumption, but not measurement of food consumption. However, I have included them and this category in this review of the prior art because the technology is nonetheless generally relevant to the invention disclosed herein. Various examples of devices and methods in this category use timing mechanisms to slow down the rate of food consumption. The underlying idea is that there is a lag between when food is consumed and when that food registers with the brain to cause a "sense of fullness" (satiety). Slowing down the rate of food consumption triggers satiety earlier, thereby reducing the overall quantity of food consumed. Several of the devices and methods in this category have a timer that periodically signals when a person should take another bite of food. This is intended to modify the speed of food consumption. Regardless of whether devices and methods in this category are used for modification of food consumption or measurement of food consumption, they depend on voluntary human action. They do not work if the person ignores the timer. They are not tamper-resistant because a person can just ignore the timer or eat without the timer. Also, such devices and methods are not useful for food identification.

Devices and methods in the prior art that appear to be based on eating speed modification include: U.S. Pat. No. 4,207,673 (DiGirolamo et al., Jun. 17, 1980, "Cutlery"); U.S. Pat. No. 4,914,819 (Ash, Apr. 10, 1990, "Eating Utensil for Indicating When Food May be Eaten Therewith and a Method for Using the Utensil"); U.S. Pat. No. 4,975,682 (Kerr et al., Dec. 4, 1990, "Meal Minder Device"); U.S. Pat. No. 5,421,089 (Dubus et al., Jun. 6, 1995, "Fork with Timer"); 5424719 (Ravid, Jun. 13, 1995, "Consumption Control"); U.S. Pat. No. 5,563,850 (Hanapole, Oct. 8, 1996, "Food Intake Timer"); U.S. Pat. No. 5,908,301 (Lutz, Jun. 1, 1999, "Method and Device for Modifying Behavior"); U.S. Pat. No. 6,473,368 (Stanfield, Oct. 29, 2002, "Consumption Controller"); U.S. Pat. No. 6,765,488 (Stanfield, Jul. 20, 2004, "Enhanced Consumption Controller"); as well as U.S. Patent Applications 20080137486 (Czarenk et al., Jun. 12, 2008, "Diet Watch"); 20090253105 (Lepine, Oct. 8, 2009, "Device for Regulating Eating by Measuring Potential"); 20120021388 (Arbuckle et al., Jan. 26, 2012, "System and Method for Weight Management").

13. Eating Frequency Modification

Devices and methods in this category are generally used for modification of food consumption, not measurement of food consumption. However, I have included them in this review because the technology is nonetheless generally relevant. In an example, such a device and method can involve storing food in containers or locations with time-limited access. The intent is to reduce between-meal snacking by only allowing access to food at specified times. However, such devices and methods only work in restrictive environments which do not permit a person to purchase (or otherwise access) food by other means. Otherwise, these devices and methods are easy for a person to circumvent.

An example of a device and method in the prior art that appears to be based on eating frequency modification is U.S. patent 20050146419 (Porter, Jul. 7, 2005, "Programmable Restricted Access Food Storage Container and Behavior Modification Assistant").

SUMMARY OF THIS INVENTION

As we discussed in previous sections of this disclosure, there remains an unmet need for a non-invasive, automatic, tamper-resistant, and relatively-inconspicuous device and method for monitoring and measuring food consumption and caloric intake. The prior art does not disclose such a device and method. Such a device and method can help to empower people and boost their willpower to better manage their energy balance and thus manage their weight. More generally, such a device and method can help to address the problem of an increasingly obese and overweight population in the United States. The invention disclosed herein meets this need and addresses the limitations of the prior art. This novel invention is a wearable, automatic, tamper-resistant, and relatively-inconspicuous device and method for monitoring and measuring food consumption and caloric intake.

This invention can be embodied as a device. Specifically, this invention can be a tamper-resistant device that automatically monitors caloric intake comprising: (1) one or more automatic-imaging members that are worn on one or more locations on a person from which these members: collectively and automatically take pictures of the person's mouth when the person eats and pictures of a reachable food source when the person eats; wherein a reachable food source is a food source that the person can reach by moving their arm; and wherein food can include liquid nourishment as well as solid food; (2) a tamper-resisting mechanism which detects and responds if the operation of the one or more automatic-imaging members is impaired; and (3) an image-analyzing member which automatically analyzes pictures of the person's mouth and pictures of the reachable food source in order to estimate the types and quantities of food that are consumed by the person.

This invention can also be embodied as a method. Specifically, this invention can be a tamper-resistant method for automatically monitoring caloric intake comprising: (1) having a person wear one or more automatic-imaging members at one or more locations on the person from which these members collectively and automatically take pictures of the person's mouth when the person eats and pictures of a reachable food source when the person eats; wherein a reachable food source is a food source that the person can reach by moving their arm; and wherein food can include liquid nourishment as well as solid food; (2) detecting and responding if the operation of the one or more automatic-imaging members is impaired; and (3) automatically analyzing pictures of the person's mouth and pictures of the reachable food source in order to estimate the types and quantities of food that are consumed by the person.

The invention herein addresses the limitations of the prior art in this field. This invention can correct the notoriously low compliance of manual food logging devices and methods because it is automatic and tamper-resistant. It does not depend on voluntary human action at the time that a person eats in order to record caloric intake. This invention also corrects the problems with current food-imaging approaches in the prior art because it is automatic, tamper-resistant, relatively-inconspicuous, and images both a food source and the person's mouth. Since this invention encompasses images of both a food source and the person's mouth, it is superior for estimating both the types and quantities of food actually consumed. In sum, this invention offers many advantages over the prior art and can be a central part of an overall system of energy balance and weight management. It can help people to boost their willpower and take charge of their eating behavior.

INTRODUCTION TO THE FIGURES

FIGS. 1-30 show examples of how this invention may be embodied, but they do not limit the full generalizability of the claims.

FIGS. 1 and 2 show two sequential views of an example of this invention comprising two opposite-facing cameras that are worn on band around a person's wrist.

FIGS. 3 and 4 show pictures of the person's mouth and of a food source from the perspectives of these two cameras.

FIGS. 5 and 6 show an example of this invention with only one camera worn on a band around the person's wrist.

FIGS. 7 and 8 show an example of this invention wherein a camera's field of vision automatically shifts as food moves toward the person's mouth.

FIGS. 9-14 show an example of how this invention functions in a six-picture sequence of food consumption.

FIGS. 15 and 16 show a two-picture sequence of how the field of vision from a single wrist-worn camera shifts as the person brings food up to their mouth.

FIGS. 17 and 18 show a two-picture sequence of how the fields of vision from two wrist-worn cameras shift as the person brings food up to their mouth.

FIGS. 19-21 show an example of how this invention can be tamper resistant by monitoring the line of sight to the person's mouth and responding if this line of sight is obstructed.

FIG. 22 shows an example of how this invention can be tamper-resistant using a first imaging member to monitor the person's mouth and a second imaging member to scan for food sources.

FIGS. 23-30 show two four-picture sequences taken by a wrist-worn prototype of this invention wherein these picture sequences encompass the person's mouth and a food source.

DETAILED DESCRIPTION OF THE FIGURES

Before going into a detailed description of the figures, it is important to first define three terms that are used repeatedly in the description. The first term, "food," is broadly defined to include liquid nourishment, such as beverages, in addition to solid food.

The second term, "reachable food source," is defined as a source of food that a person can access and from which they can bring a piece (or portion) of food to their mouth by moving their arm and hand. Arm and hand movement can include movement of the person's shoulder, elbow, wrist, and finger joints. In various examples, a reachable food source can be selected from the group consisting of: food on a plate, food in a bowl, food in a glass, food in a cup, food in a bottle, food in a can, food in a package, food in a container, food in a wrapper, food in a bag, food in a box, food on a table, food on a counter, food on a shelf, and food in a refrigerator.

The third term, "food consumption pathway," is defined as a path in space that is traveled by (a piece of) food from a reachable food source to a person's mouth as the person eats. The distal endpoint of a food consumption pathway is the reachable food source and the proximal endpoint of a food consumption pathway is the person's mouth. In various examples, food may be moved along the food consumption pathway by contact with a member selected from the group consisting of: a utensil; a beverage container; the person's fingers; and the person's hand.

The following figures, FIGS. 1-30, show various examples of how this invention may be embodied in a device and method to reduce or prevent snoring. However, these examples are not exhaustive and do not limit the full generalizability of the claims.

Figure 1:
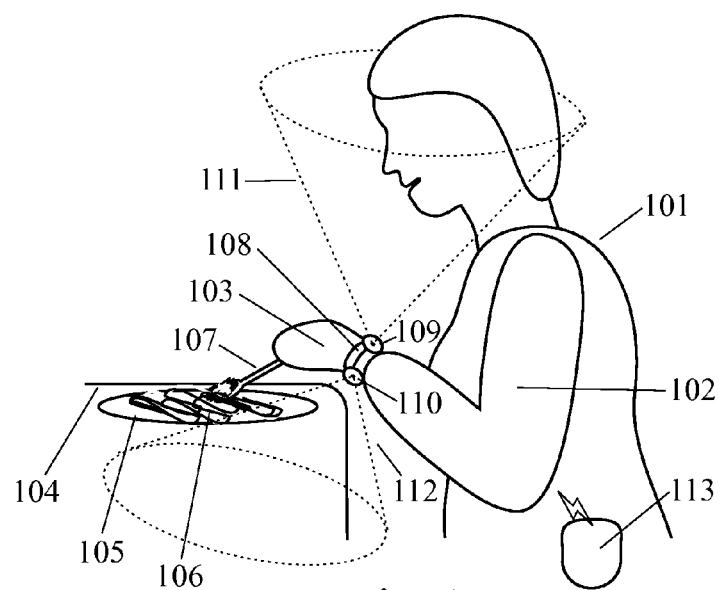
Figure 2:
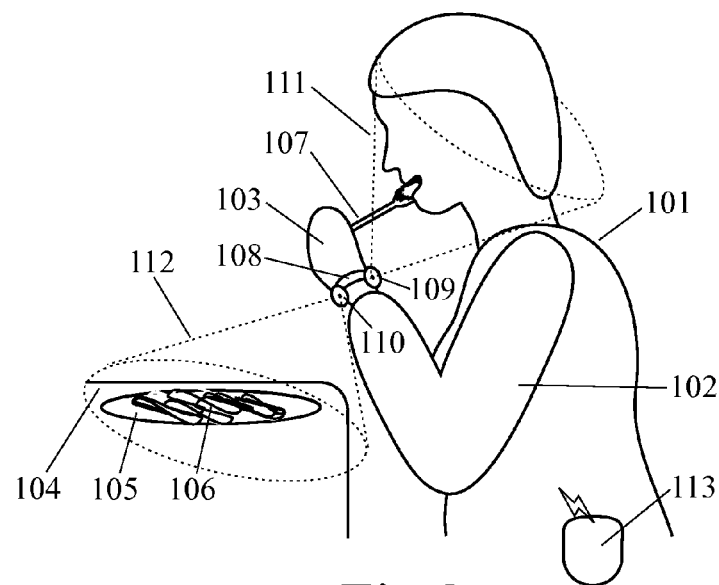

We now begin the description of FIGS. 1 and 2 with an introductory overview. A detailed description will follow. FIGS. 1 and 2 show one example of how this invention may be embodied in a device and method for automatically monitoring and estimating human caloric intake. In this example, the device and method comprise an automatic-imaging member that is worn on a person's wrist. This imaging member has two cameras attached to a wrist band on opposite (narrow) sides of the person's wrist.

These two cameras take pictures of a reachable food source and the person's mouth. These pictures are used to estimate, in an automatic and tamper-resistant manner, the types and quantities of food consumed by the person. Information on food consumed, in turn, is used to estimate the person's caloric intake. As the person eats, these two cameras of the automatic-imaging member take pictures of a reachable food source and the person's mouth. These pictures are analyzed, using pattern recognition or other image-analyzing methods, to estimate the types and quantities of food that the person consumes. In this example, these pictures are motion pictures (e.g. videos). In another example, these pictures may be still-frame pictures.

We now discuss FIGS. 1 and 2, including their components, in detail. FIG. 1 shows person 101 seated at table 104 wherein this person is using their arm 102 and hand 103 to access food 106 on plate 105 located on table 104. In this example in FIGS. 1 and 2, food 106 on plate 105 comprises a reachable food source. In this example, person 101 is shown picking up a piece of food 106 from the reachable food source using utensil 107. In various examples, a food source may be selected from the group consisting of: food on a plate, food in a bowl, food in a glass, food in a cup, food in a bottle, food in a can, food in a package, food in a container, food in a wrapper, food in a bag, food in a box, food on a table, food on a counter, food on a shelf, and food in a refrigerator.

In this example, the person is wearing an automatic-imaging member comprised of a wrist band 108 to which are attached two cameras, 109 and 110, on the opposite (narrow) sides of the person's wrist. Camera 109 takes pictures within field of vision 111. Camera 110 takes pictures within field of vision 112. Each field of vision, 111 and 112, is represented in these figures by a dotted-line conical shape. The narrow tip of the dotted-line cone is at the camera's aperture and the circular base of the cone represents the camera's field of vision at a finite focal distance from the camera's aperture.

In this example, camera 109 is positioned on the person's wrist at a location from which it takes pictures along an imaging vector that is directed generally upward from the automatic-imaging member toward the person's mouth as the person eats. In this example, camera 110 is positioned on the person's wrist at a location from which it takes pictures along an imaging vector that is directed generally downward from the automatic-imaging member toward a reachable food source as the person eats. These imaging vectors are represented in FIG. 1 by the fields of vision, 111 and 112, indicated by cone-shaped dotted-line configurations. The narrow end of the cone represents the aperture of the camera and the circular end of the cone represents a focal distance of the field of vision as seen by the camera. Although theoretically the field of vision could extend outward in an infinite manner from the aperture, we show a finite length cone to represent a finite focal length for a camera's field of vision.

Field of vision 111 from camera 109 is represented in FIG. 1 by a generally upward-facing cone-shaped configuration of dotted lines that generally encompasses the person's mouth and face as the person eats. Field of vision 112 from camera 110 is represented in FIG. 1 by a generally downward-facing cone-shaped configuration of dotted lines that generally encompasses the reachable food source as the person eats.

This device and method of taking pictures of both a reachable food source and the person's mouth, while a person eats, can do a much better job of estimating the types and quantities of food actually consumed than one of the devices or methods in the prior art that only takes pictures of either a reachable food source or the person's mouth. There is prior art that uses imaging to identify food that requires a person to manually aim a camera toward a food source and then manually take a picture of the food source. Such prior art does not take also pictures of the person's mouth. There are multiple disadvantages with this prior art. We will discuss later the disadvantages of requiring manual intervention to aim a camera and push a button to take a picture. For now, we discuss the disadvantages of prior art that only takes pictures of a reachable food source or only takes pictures of the person's mouth, but not both.

First, let us consider a "source-only" imaging device, such as those in the prior art, that only takes pictures of a food source within a reachable distance of the person and does not also take pictures of the person's mouth. Using a "source-only" device, it is very difficult to know whether the person actually consumes the food that is seen in the pictures. A "source-only" imaging device can be helpful in identifying what types of foods the person has reachable access to, and might possibly eat, but such a device is limited as means for measuring how much of these foods the person actually consumes. For example, consider a person walking through a grocery store. As the person walks through the store, a wide variety of food sources in various packages and containers come into a wearable camera's field of vision. However, the vast majority of these food sources are ones that the person never consumes. The person only actually consumes those foods that the person buys and consumes later. An automatic wearable imaging system that only takes pictures of reachable food sources would be very limited for determining how many of these reachable food sources are actually consumed by the person.

One could try to address this problem by making the picture-taking process a manual process rather than an automatic process. One could have an imaging system that requires human intervention to actively aim a camera (e.g. a mobile imaging device) at a food source and also require human intervention (to click a button) to indicate that the person is actually going to consume that food. However, relying on such a manual process for caloric intake monitoring makes this process totally dependent on the person's compliance. Even if a person wants to comply, it can be tough for a person to manually aim a camera and take pictures each time that the person snacks on something. If the person does not want to comply, the situation is even worse. It is easy for a person to thwart a monitoring process that relies on manual intervention. All that a person needs to do to thwart the process is to not take pictures of something that they eat.

A manual imaging system is only marginally better than old-fashioned "calorie counting" by writing down what a person eats on a piece of paper or entering it into a computer. If a person buys a half-gallon of ice cream and consumes it without manually taking a picture of the ice-cream, either intentionally or by mistaken omission, then the device that relies on a manual process is clueless with respect to those calories consumed. A "source-only" imaging device makes it difficult, if not impossible, to track food actually consumed without manual intervention. Further, requiring manual intervention to record consumption makes it difficult, if not impossible, to fully automate calorie monitoring and estimation.

As another example of the limitations of a "source-only" imaging device, consider the situation of a person sitting at a table with many other diners wherein the table is set with food in family-style communal serving dishes. These family-style dishes are passed around to serve food to everyone around the table. It would be challenging for a "source-only" imaging device to automatically differentiate between these communal serving dishes and a person's individual plate. What happens when the person's plate is removed or replaced? What happens when the person does not eat all of the food on their plate? These examples highlight the limitations of a device and method that only takes pictures of a reachable food source, without also taking pictures of the person's mouth.

This present invention overcomes these limitations by automatically taking pictures of both a reachable food source and the person's mouth. With images of both a reachable food source and the person's mouth, as the person eats, this present device and method can determine not only what food the person has access to, but how much of that food the person actually eats.

We have considered the limitations of devices and methods in the prior art that only take pictures of a reachable food source. We now also consider the limitations of "mouth-only" imaging devices and methods, wherein these devices only take pictures of the person's mouth while they eat. It is very difficult for a "mouth-only" imaging device to use pattern recognition, or some other image-based food identification method, on a piece of food approaching the person's mouth to identify the food, without also having pictures of the total food source.

For example, pattern recognition software can identify the type of food at a reachable food source by: analyzing the food's shape, color, texture, and volume; or by analyzing the food's packaging. However, it is much more difficult for a device to identify a piece (or portion) of food that is obscured within in the scoop of a spoon, hidden within a cup, cut and then pierced by the tines of a fork, or clutched in partially-closed hand as it is brought up to the person's mouth.

For example, pattern recognition software could identify a bowl of peanuts on a table, but would have a tough time identifying a couple peanuts held in the palm of a person's partially-closed hand as they move from the bowl to the person's mouth. It is difficult to get a line of sight from a wearable imaging member to something inside the person's hand as it travels along the food consumption pathway. For these reasons, a "mouth-only" imaging device may be useful for estimating the quantity of food consumed (possibly based on the number of food consumption pathway motions, chewing motions, swallowing motions, or a combination thereof) but is limited for identifying the types of foods consumed, without having food source images as well.

We have discussed the limitations of "source-only" and "mouth-only" prior art that images only a reachable food source or only a person's mouth. This present invention is an improvement over this prior art because it comprises a device and method that automatically estimates the types and quantities of food actually consumed based on pictures of both a reachable food source and the person's mouth. Having both such images provides better information than either separately. Pictures of a reachable food source may be particularly useful for identifying the types of food available to the person for potential consumption. Pictures of the person's mouth (including food traveling the food consumption pathway and food-mouth interaction such as chewing and swallowing) may be particularly useful for identifying the quantity of food consumed by the person. Combining both images in an integrated analysis provides more accurate estimation of the types and quantities of food actually consumed by the person. This information, in turn, provides better estimation of caloric intake by the person.

The fact that this present invention is wearable further enhances its superiority over prior art that is non-wearable. It is possible to have a non-wearable imaging device that can be manually positioned (on a table or other surface) to be aimed toward an eating person, such that its field of vision includes both a food source and the person's mouth. In theory, every time the person eats a meal or takes a snack, the person could: take out an imaging device (such as a smart phone); place the device on a nearby surface (such as a table, bar, or chair); manually point the device toward them so that both the food source and their mouth are in the field of vision; and manually push a button to initiate picture taking before they start eating. However, this manual process with a non-wearable device is highly dependent on the person's compliance with this labor-intensive and possibly-embarrassing process.

Even if a person has good intentions with respect to compliance, it is expecting a lot for a person to carry around a device and to set it up at just the right direction each time that the person reaches for a meal or snack. How many people, particularly people struggling with their weight and self-image, would want to conspicuously bring out a mobile device, place it on a table, and manually aim it toward themselves when they eat, especially when they are out to eat with friends or on a date? Even if this person has good intentions with respect to compliance with a non-wearable food-imaging device, it is very unlikely that compliance would be high. The situation would get even worse if the person is tempted to obstruct the operation of the device to cheat on their "diet." With a non-wearable device, tampering with the operation of the device is easy as pie (literally). All the person has to do is to fail to properly place and activate the imaging device when they snack.

It is difficult to design a non-wearable imaging device that takes pictures, in an automatic and tamper-resistant manner, of both a food source and the person's mouth whenever the person eats. Is it easier to design a wearable imaging device that takes pictures, in an automatic and tamper-resistant manner, of a food source and the person's mouth whenever the person eats. Since the device and method disclosed herein is wearable, it is an improvement over non-wearable prior art, even if that prior art could be used to manually take pictures of a food source and a person's mouth.

The fact that the device and method disclosed herein is wearable makes it less dependent on human intervention, easier to automate, and easier to make tamper-resistant. With the present invention, there is no requirement that a person must carry around a mobile device, place it on an external surface, and aim it toward a food source and their mouth every time that they eat in order to track total caloric intake. This present device, being wearable and automatic, goes with the person where ever they go and automatically takes pictures whenever they eat, without the need for human intervention.

In an example, this device may have an unobtrusive, or even attractive, design like a piece of jewelry. In various examples, this device may look similar to an attractive wrist watch, bracelet, finger ring, necklace, or ear ring. As we will discuss further, the wearable and automatic imaging nature of this invention allows the incorporation of tamper-resistant features into this present device to increase the accuracy and compliance of caloric intake monitoring and estimation.

For measuring total caloric intake, ideally it is desirable to have a wearable device and method that automatically monitors and estimates caloric intake in a comprehensive and involuntary manner. The automatic and involuntary nature of a device and method will enhance accuracy and compliance. This present invention makes significant progress toward this goal, especially as compared to the limitations of relevant prior art. There are devices and methods in the prior art that assist in manual calorie counting, but they are heavily reliant on the person's compliance. The prior art does not appear to disclose a wearable, automatic, tamper-resistant, image-based device or method that takes pictures of a food source and a person's mouth in order to estimate the person's caloric intake.

The fact that this device and method incorporates pictures of both a food source and the person's mouth, while a person eats, makes it much more accurate than prior art that takes pictures of only a food source or only the person's mouth. The wearable nature of this invention makes it less reliant on manual activation, and much more automatic in its imaging operation, than non-wearable devices. This present device does not depend on properly placing, aiming, and activating an imaging member every time a person eats. This device and method operates in an automatic manner and is tamper resistant. All of these features combine to make this invention a more accurate and dependable device and method of monitoring and measuring human caloric intake than devices and methods in the prior art. This present invention can serve well as the caloric-intake measuring component of an overall system of human energy balance and weight management.

In the example of this invention that is shown in FIG. 1, the pictures of the person's mouth and the pictures of the reachable food source that are taken by cameras 109 and 110 (part of a wrist-worn automatic-imaging member) are transmitted wirelessly to image-analyzing member 113 that is worn elsewhere on the person. In this example, image-analyzing member 113 automatically analyzes these images to estimate the types and quantities of food consumed by the person. There are many methods of image analysis and pattern recognition in the prior art and the precise method of image analysis is not central to this invention. Accordingly, the precise method of image analysis is not specified herein.

In an example, this invention includes an image-analyzing member that uses one or more methods selected from the group consisting of: pattern recognition or identification; human motion recognition or identification; face recognition or identification; gesture recognition or identification; food recognition or identification; word recognition or identification; logo recognition or identification; bar code recognition or identification; and 3D modeling.

In an example, this invention includes an image-analyzing member that analyzes one or more factors selected from the group consisting of: number of reachable food sources; types of reachable food sources; changes in the volume of food at a reachable food source; number of times that the person brings food to their mouth; sizes of portions of food that the person brings to their mouth; number of chewing movements; frequency or speed of chewing movements; and number of swallowing movements.

In an example, this invention includes an image-analyzing member that provides an initial estimate of the types and quantities of food consumed by the person and this initial estimate is then refined by human interaction and/or evaluation.

In an example, this invention includes wireless communication from a first wearable member (that takes pictures of a reachable food source and a person's mouth) to a second wearable member (that analyzes these pictures to estimate the types and quantities of food consumed by the person). In another example, this invention may include wireless communication from a wearable member (that takes pictures of a reachable food source and a person's mouth) to a non-wearable member (that analyzes these pictures to estimate the types and quantities of food consumed by the person). In another example, this invention may include a single wearable member that takes and analyzes pictures, of a reachable food source and a person's mouth, to estimate the types and quantities of food consumed by the person.

In the example of this invention that is shown in FIG. 1, an automatic-imaging member is worn around the person's wrist. Accordingly, the automatic-imaging member moves as food travels along the food consumption pathway. This means that the imaging vectors and the fields of vision, 111 and 112, from the two cameras, 109 and 110, that are located on this automatic-imaging member, shift as the person eats.

In this example, the fields of vision from these two cameras on the automatic-imaging member automatically and collectively encompass the person's mouth and a reachable food source, from at least some locations, as the automatic-imaging member moves when food travels along the food consumption pathway. In this example, this movement allows the automatic-imaging member to take pictures of both the person's mouth and the reachable food source, as the person eats, without the need for human intervention to manually aim cameras toward either the person's mouth or a reachable food source, when the person eats.

The reachable food source and the person's mouth do not need to be within the fields of vision, 111 and 112, at all times in order for the device and method to accurately estimate food consumed. As long as the reachable food source and the person's mouth are encompassed by the field of vision from at least one of the two cameras at least once during each movement cycle along the food consumption pathway, the device and method should be able to reasonably interpolate missing intervals and to estimate the types and quantities of food consumed.

FIG. 2 shows the same example of the device and method for automatically monitoring and estimating caloric intake that was shown in FIG. 1, but at a later point as food moves along the food consumption pathway. In FIG. 2, a piece of food has traveled from the reachable food source to the person's mouth via utensil 107. In FIG. 2, person 101 has bent their arm 102 and rotated their hand 103 to bring this piece of food, on utensil 107, up to their mouth. In FIG. 2, field of vision 112 from camera 110, located on the distal side of the person's wrist, now more fully encompasses the reachable food source. Also, field of vision 111 from camera 109, located on the proximal side of the person's wrist, now captures the interaction between the piece of food and the person's mouth.

Figure 3:
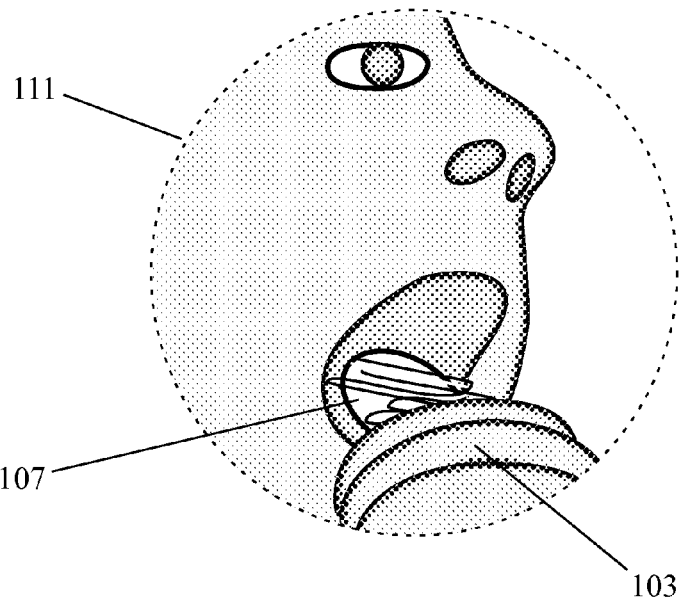
Figure 4:
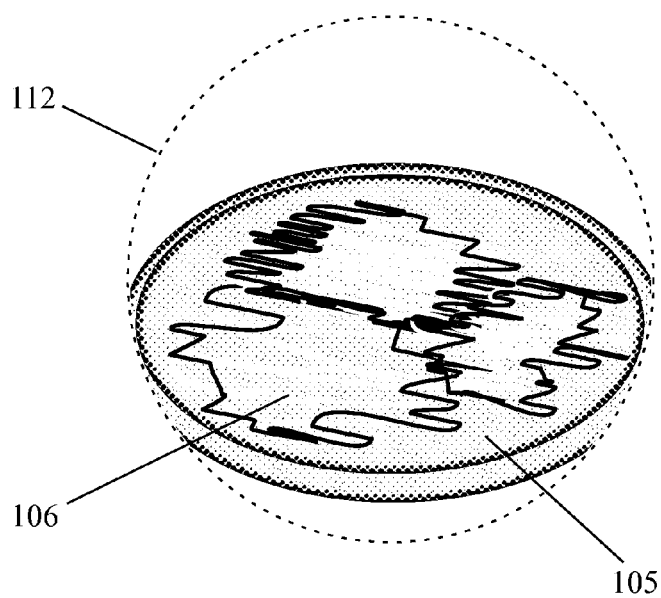

FIGS. 3 and 4 provide additional insight into how this device and method for monitoring and estimating caloric intake works. FIGS. 3 and 4 show still-frame views of the person's mouth and the reachable food source as captured by the fields of vision, 111 and 112, from the two cameras, 109 and 110, worn on the person's wrist, as the person eats. In FIGS. 3 and 4, the boundaries of fields of vision 111 and 112 are represented by dotted-line circles. These dotted-line circles correspond to the circular ends of the dotted-line conical fields of vision that are shown in FIG. 2.

For example, FIG. 2 shows a side view of camera 109 with conical field of vision 111 extending outwards from the camera aperture and upwards toward the person's mouth. FIG. 3 shows this same field of vision 111 from the perspective of the camera aperture. In FIG. 3, the person's mouth is encompassed by the circular end of the conical field of vision 111 that was shown in FIG. 2. In this manner, FIG. 3 shows a close-up view of utensil 107, held by hand 103, as it inserts a piece of food into the person's mouth.

As another example, FIG. 2 shows a side view of camera 110 with conical field of vision 112 extending outwards from the camera aperture and downwards toward the reachable food source. In this example, the reachable food source is food 106 on plate 105. FIG. 4 shows this same field of vision 112 from the perspective of the camera aperture. In FIG. 4, the reachable food source is encompassed by the circular end of the conical field of vision 112 that was shown in FIG. 2. In this manner, FIG. 4 shows a close-up view of food 106 on plate 105.

The example of this invention for monitoring and estimating human caloric intake that is shown in FIGS. 1-4 comprises a wearable imaging device. In various examples, this invention can be a device and method for measuring caloric intake that comprises one or more automatic-imaging members that are worn on a person at one or more locations from which these members automatically take (still or motion) pictures of the person's mouth as the person eats and automatically take (still or motion) pictures of a reachable food source as the person eats. In this example, these images are automatically analyzed to estimate the types and quantities of food actually consumed by the person.

In an example, there may be one automatic-imaging member that takes pictures of both the person's mouth and a reachable food source. In an example, there may be two or more automatic-imaging members, worn on one or more locations on a person, that collectively and automatically take pictures of the person's mouth when the person eats and pictures of a reachable food source when the person eats. In an example, this picture taking can occur in an automatic and tamper-resistant manner as the person eats.

In various examples, one or more imaging devices worn on a person's body take pictures of food at multiple points as it moves along the food consumption pathway. In various examples, this invention comprises a wearable, mobile, calorie-input-measuring device that automatically records and analyzes food images in order to detect and measure human caloric input. In various examples, this invention comprises a wearable, mobile, energy-input-measuring device that automatically analyzes food images to measure human energy input.

In an example, this device and method comprise one or more imaging members that take pictures of: food at a food source; a person's mouth; and interaction between food and the person's mouth. The interaction between the person's mouth and food can include biting, chewing, and swallowing. In an example, utensils or beverage-holding members may be used as intermediaries between the person's hand and food. In an example, this invention comprises an imaging device that automatically takes pictures of the interaction between food and the person's mouth as the person eats. In an example, this invention comprises a wearable device that takes pictures of a reachable food source that is located in front of the person.

In an example, this invention comprises a method of estimating a person's caloric intake that includes the step of having the person wear one or more imaging devices, wherein these imaging devices collectively and automatically take pictures of a reachable food source and the person's mouth. In an example, this invention comprises a method of measuring a person's caloric intake that includes having the person wear one or more automatic-imaging members, at one or more locations on the person, from which locations these members are able to collectively and automatically take pictures of the person's mouth as the person eats and take pictures of a reachable food source as the person eats.

In the example of this invention that is shown in FIGS. 1 and 2, two cameras, 109 and 110, are worn on the narrow sides of the person's wrist, between the posterior and anterior surfaces of the wrist, such that the moving field of vision from the first of these cameras automatically encompasses the person's mouth (as the person moves their arm when they eat) and the moving field of vision from the second of these cameras automatically encompasses the reachable food source (as the person moves their arm when they eat). This embodiment of the invention is comparable to a wrist-watch that has been rotated 90 degrees around the person's wrist, with a first camera located where the watch face would be and a second camera located on the opposite side of the wrist.

In another example, this device and method can comprise an automatic-imaging member with a single wide-angle camera that is worn on the narrow side of a person's wrist or upper arm, in a manner similar to wearing a watch or bracelet that is rotated approximately 90 degrees. This automatic-imaging member can automatically take pictures of the person's mouth, a reachable food source, or both as the person moves their arm and hand as the person eats. In another example, this device and method can comprise an automatic-imaging member with a single wide-angle camera that is worn on the anterior surface of a person's wrist or upper arm, in a manner similar to wearing a watch or bracelet that is rotated approximately 180 degrees. This automatic-imaging member automatically takes pictures of the person's mouth, a reachable food source, or both as the person moves their arm and hand as the person eats. In another example, this device and method can comprise an automatic-imaging member that is worn on a person's finger in a manner similar to wearing a finger ring, such that the automatic-imaging member automatically takes pictures of the person's mouth, a reachable food source, or both as the person moves their arm and hand as the person eats.

In various examples, this invention comprises a caloric-input measuring member that automatically estimates a person's caloric intake based on analysis of pictures taken by one or more cameras worn on the person's wrist, hand, finger, or arm. In various examples, this invention includes one or more automatic-imaging members worn on a body member selected from the group consisting of: wrist, hand, finger, upper arm, and lower arm. In various examples, this invention includes one or more automatic-imaging members that are worn in a manner similar to a wearable member selected from the group consisting of: wrist watch; bracelet; arm band; and finger ring.

In various examples of this device and method, the fields of vision from one or more automatic-imaging members worn on the person's wrist, hand, finger, or arm are shifted by movement of the person's arm bringing food to their mouth along the food consumption pathway. In an example, this movement causes the fields of vision from these one or more automatic-imaging members to collectively and automatically encompass the person's mouth and a reachable food source.

In various examples, this invention includes one or more automatic-imaging members that are worn on a body member selected from the group consisting of: neck; head; and torso. In various examples, this invention includes one or more automatic-imaging members that are worn in a manner similar to a wearable member selected from the group consisting of: necklace; pendant, dog tags; brooch; cuff link; ear ring; eyeglasses; wearable mouth microphone; and hearing aid.

In an example, this device and method comprise at least two cameras or other imaging members. A first camera may be worn on a location on the human body from which it takes pictures along an imaging vector which points toward the person's mouth while the person eats. A second camera may be worn on a location on the human body from which it takes pictures along an imaging vector which points toward a reachable food source. In an example, this invention may include: (a) an automatic-imaging member that is worn on the person's wrist, hand, arm, or finger such that the field of vision from this member automatically encompasses the person's mouth as the person eats; and (b) an automatic-imaging member that is worn on the person's neck, head, or torso such that the field of vision from this member automatically encompasses a reachable food source as the person eats.

In other words, this device and method can comprise at least two automatic-imaging members that are worn on a person's body. One of these automatic-imaging members may be worn on a body member selected from the group consisting of the person's wrist, hand, lower arm, and finger, wherein the field of vision from this automatic-imaging member automatically encompasses the person's mouth as the person eats. A second of these automatic-imaging members may be worn on a body member selected from the group consisting of the person's neck, head, torso, and upper arm, wherein the field of vision from the second automatic-imaging member automatically encompasses a reachable food source as the person eats.

In various examples, one or more automatic-imaging members may be integrated into one or more wearable members that appear similar to a wrist watch, wrist band, bracelet, arm band, necklace, pendant, brooch, collar, eyeglasses, ear ring, headband, or ear-mounted bluetooth device. In an example, this device may comprise two imaging members, or two cameras mounted on a single member, which are generally perpendicular to the longitudinal bones of the upper arm. In an example, one of these imaging members may have an imaging vector that points toward a food source at different times while food travels along the food consumption pathway. In an example, another one of these imaging members may have an imaging vector that points toward the person's mouth at different times while food travels along the food consumption pathway. In an example, these different imaging vectors may occur simultaneously as food travels along the food consumption pathway. In another example, these different imaging vectors may occur sequentially as food travels along the food consumption pathway. This device and method may provide images from multiple imaging vectors, such that these images from multiple perspectives are automatically and collectively analyzed to identify the types and quantities of food consumed by the person.

In an example of this invention, multiple imaging members may be worn on the same body member. In another example, multiple imaging members may be worn on different body members. In an example, an imaging member may be worn on each of a person's wrists or each of a person's hands. In an example, one or more imaging members may be worn on a body member and a supplemental imaging member may be located in a non-wearable device that is in proximity to the person. In an example, wearable and non-wearable imaging members may be in wireless communication with each other. In an example, wearable and non-wearable imaging members may be in wireless communication with an image-analyzing member.

In an example, a wearable imaging member may be worn on the person's body, a non-wearable imaging member may be positioned in proximity to the person's body, and a tamper-resisting mechanism may ensure that both the wearable and non-wearable imaging members are properly positioned to take pictures as the person eats. In various examples, this device and method may include one or more imaging members that are worn on the person's neck, head, or torso and one or more imaging devices that are positioned on a table, counter, or other surface in front of the person in order to simultaneously, or sequentially, take pictures of a reachable food source and the person's mouth as the person eats.

In an example, this invention comprises an imaging device with multiple imaging components that take images along different imaging vectors so that the device takes pictures of a reachable food source and a person's mouth simultaneously. In an example, this invention comprises an imaging device with a wide-angle lens that takes pictures within a wide field of vision so that the device takes pictures of a reachable food source and a person's mouth simultaneously.

FIGS. 5 through 8 show additional examples of how this device and method for monitoring and estimating human caloric intake can be embodied. These examples are similar to the examples shown previously in that they comprise one or more automatic-imaging members that are worn on a person's wrist. These examples similar to the example shown in FIGS. 1 and 2, except that now in FIGS. 5 through 8 there is only one camera 502 located a wrist band 501.

Figure 5:
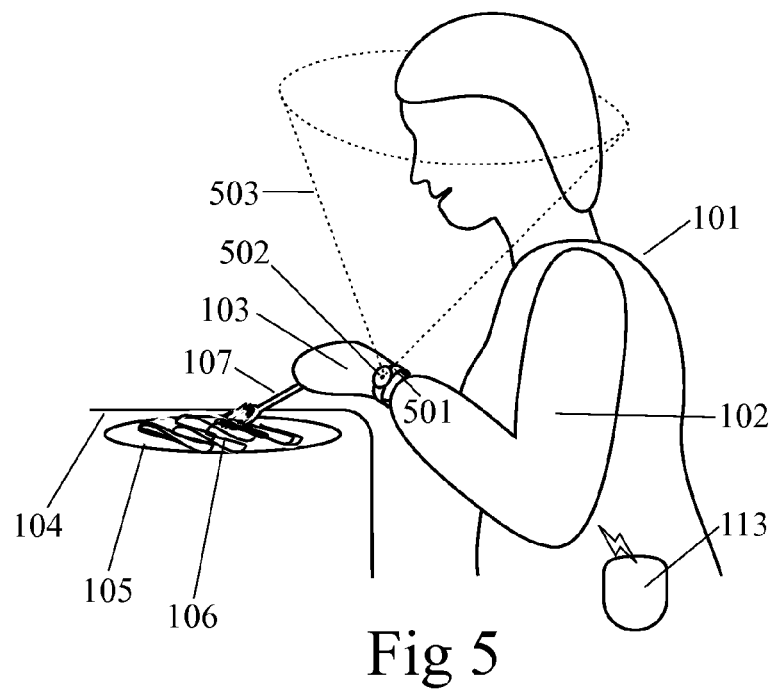
Figure 6:
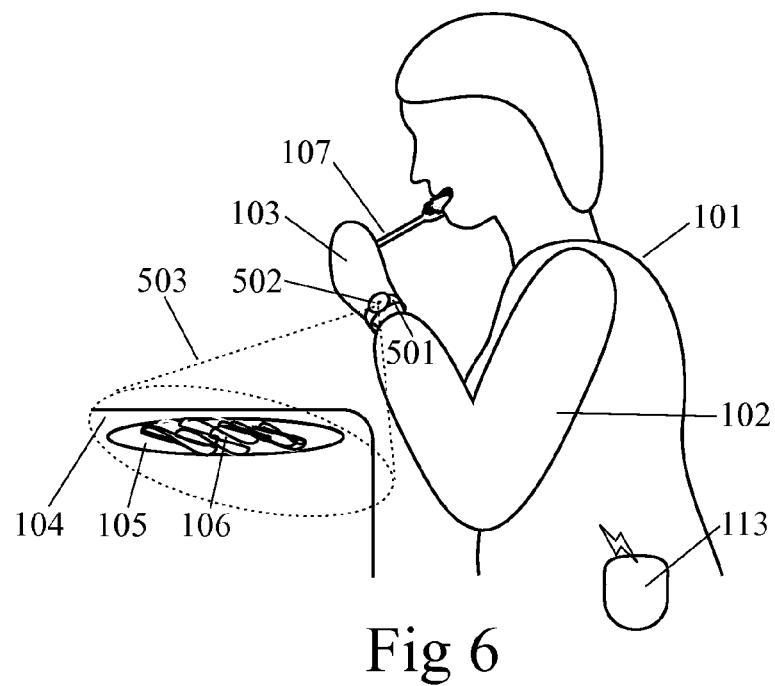

This automatic-imaging member has features that enable the one camera, 502, to take pictures of both the person's mouth and a reachable food source with only a single field of vision 503. In an example, this single wrist-mounted camera has a wide-angle lens that allows it to take pictures of the person's mouth when a piece of food is at a first location along the food consumption pathway (as shown in FIG. 5) and allows it to take pictures of a reachable food source when a piece food is at a second location along the food consumption pathway (as shown in FIG. 6).

Figure 7:
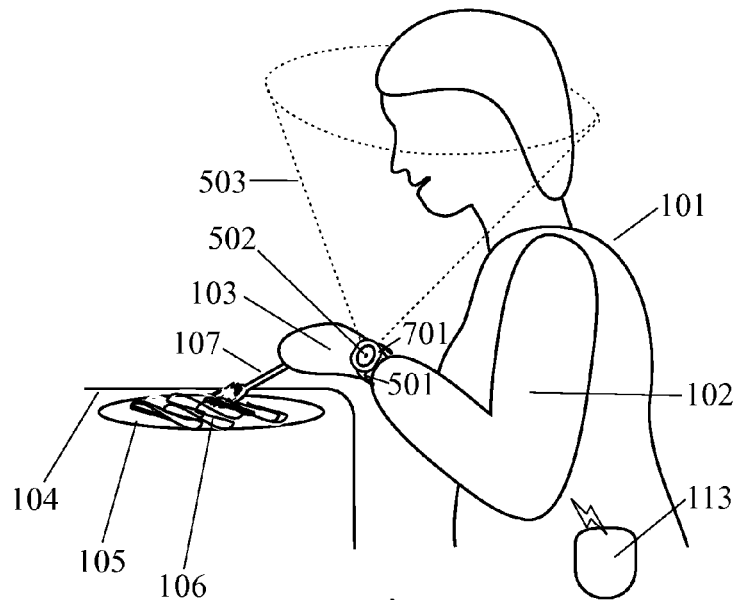
Figure 8:
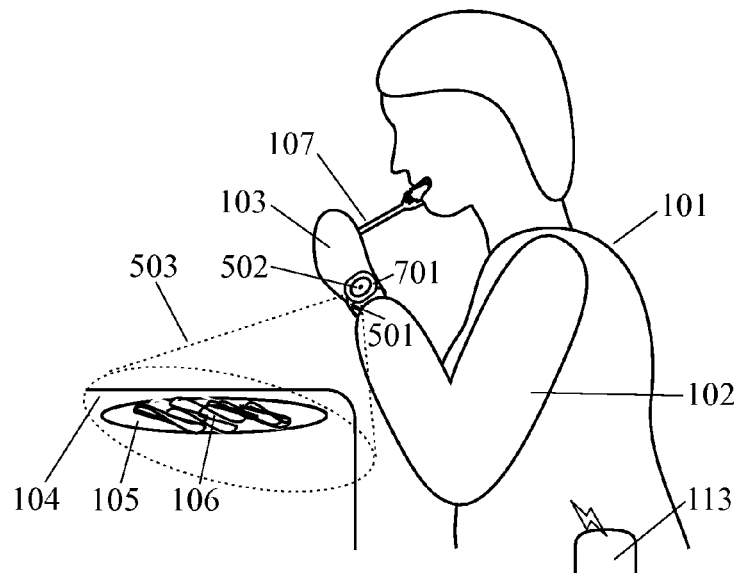

In an example, such as that shown in FIGS. 7 and 8, a single wrist-mounted camera is linked to a mechanism that shifts the camera's imaging vector (and field of vision) automatically as food moves along the food consumption pathway. This shifting imaging vector allows a single camera to encompass a reachable food source and the person's mouth, sequentially, from different locations along the food consumption pathway.

In the example of this invention that is shown in FIGS. 7 and 8, an accelerometer 701 is worn on the person's wrist and linked to the imaging vector of camera 502. Accelerometer 701 detects arm and hand motion as food moves along the food consumption pathway. Information concerning this arm and hand movement is used to automatically shift the imaging vector of camera 502 such that the field of vision, 503, of camera 502 sequentially captures images of the reachable food source and the person's mouth from different positions along the food consumption pathway. In an example, when accelerometer 701 indicates that the person's arm is in the downward phase of the food consumption pathway (in proximity to the reachable food source) then the imaging vector of camera 502 is directed upwards to get a good picture of the person's mouth interacting with food. Then, when accelerometer 701 indicates that the person's arm is in the upward phase of the food consumption pathway (in proximity to the person's mouth), the imaging vector of camera 502 is directed downwards to get a good picture of the reachable food source.

A key advantage of this present invention for monitoring and measuring a person's caloric intake is that it works in an automatic and (virtually) involuntary manner. It does not require human intervention each time that a person eats to aim a camera and push a button in order to take the pictures necessary to estimate the types and quantities of food consumed. This is a tremendous advantage over prior art that requires human intervention to aim a camera (at a food source, for example) and push a button to manually take pictures. The less human intervention that is required to make the device work, the more accurate the device and method will be in measuring total caloric intake. Also, the less human intervention that is required, the easier it is to make the device and method tamper-resistant.

Ideally, one would like an automatic, involuntary, and tamper-resistant device and method for monitoring and measuring caloric intake—a device and method which not only operates independently from human intervention at the time of eating, but which can also detect and respond to possible tampering or obstruction of the imaging function. At a minimum, one would like a device and method that does not rely on the person to manually aim a camera and manually initiate pictures each time the person eats. A manual device puts too much of a burden on the person to stay in compliance. At best, one would like a device and method that detects and responds if the person tampers with the imaging function of the device and method. This is critical for obtaining an accurate overall estimate of a person's caloric intake. The device and method disclosed herein is a significant step toward an automatic, involuntary, and tamper-resistant device, system, and method of caloric intake monitoring and measuring.

In an example, this device and method comprise one or more automatic-imaging members that automatically and collectively take pictures of a person's mouth and pictures of a reachable food source as the person eats, without the need for human intervention to initiate picture taking when the person starts to eat. In an example, this invention comprises one or more automatic-imaging members that collectively and automatically take pictures of the person's mouth and pictures of a reachable food source, when the person eats, without the need for human intervention, when the person eats, to activate picture taking by pushing a button on a camera.

In an example, one way to design a device and method to take pictures when a person eats without the need for human intervention is to simply have the device take pictures continuously. If the device is never turned off and takes pictures all the time, then it necessarily takes pictures when a person eats. In an example, such a device and method can: continually track the location of, and take pictures of, the person's mouth; continually track the location of, and take pictures of, the person's hands; and continually scan for, and take pictures of, any reachable food sources nearby.

However, having a wearable device that takes pictures all the time can raise privacy concerns. Having a device that continually takes pictures of a person's mouth and continually scans space surrounding the person for potential food sources may be undesirable in terms of privacy, excessive energy use, or both. People may be so motivated to monitor caloric intake and to lose weight that the benefits of a device that takes pictures all the time may outweigh privacy concerns. Accordingly, this invention may be embodied in a device and method that takes pictures all the time. However, for those for whom such privacy concerns are significant, we now consider some alternative approaches for automating picture taking when a person eats.

In an example, an alternative approach to having imaging members take pictures automatically when a person eats, without the need for human intervention, is to have the imaging members start taking pictures only when sensors indicate that the person is probably eating. This can reduce privacy concerns as compared to a device and method that takes pictures all the time. In an example, an imaging device and method can automatically begin taking images when wearable sensors indicate that the person is probably consuming food.

In an example of this alternative approach, this device and method may take pictures of the person's mouth and scan for a reachable food source only when a wearable sensor, such as the accelerometer 701 in FIGS. 7 and 8, indicates that the person is (probably) eating. In various examples, one or more sensors that detect when the person is (probably) eating can be selected from the group consisting of: accelerometer, inclinometer, motion sensor, sound sensor, smell sensor, blood pressure sensor, heart rate sensor, EEG sensor, ECG sensor, EMG sensor, electrochemical sensor, gastric activity sensor, GPS sensor, location sensor, image sensor, optical sensor, piezoelectric sensor, respiration sensor, strain gauge, electrogoniometer, chewing sensor, swallow sensor, temperature sensor, and pressure sensor.

In various examples, indications that a person is probably eating may be selected from the group consisting of: acceleration, inclination, twisting, or rolling of the person's hand, wrist, or arm; acceleration or inclination of the person's lower arm or upper arm; bending of the person's shoulder, elbow, wrist, or finger joints; movement of the person's jaw, such as bending of the jaw joint; smells suggesting food that are detected by an artificial olfactory sensor; detection of chewing, swallowing, or other eating sounds by one or more microphones; electromagnetic waves from the person's stomach, heart, brain, or other organs; GPS or other location-based indications that a person is in an eating establishment (such as a restaurant) or food source location (such as a kitchen).

In previous paragraphs, we discussed how this present invention is superior to prior art because this present invention does not require manual activation of picture taking each time that a person eats. This present invention takes pictures automatically when a person eats. We now discuss how this present invention is also superior to prior art because this present invention does not require manual aiming of a camera (or other imaging device) toward the person's mouth or a reachable food source each time that a person eats. This present invention automatically captures the person's mouth and a reachable food source within imaging fields of vision when a person eats.

In an example, this device and method comprise one or more automatic-imaging members that automatically and collectively take pictures of a person's mouth and pictures of a reachable food source as the person eats, without the need for human intervention to actively aim or focus a camera toward a person's mouth or a reachable food source. In an example, this device and method takes pictures of a person's mouth and a food source automatically by eliminating the need for human intervention to aim an imaging member, such as a camera, towards the person's mouth and the food source. This device and method includes imaging members whose locations, and/or the movement of those locations while the person eats, enables the fields of vision of the imaging members to automatically encompass the person's mouth and a food source.

In an example, the fields of vision from one or more automatic-imaging members in this invention collectively and automatically encompass the person's mouth and a reachable food source, when the person eats, without the need for human intervention (when the person eats) to manually aim an imaging member toward the person's mouth or toward the reachable food source. In an example, the automatic-imaging members have wide-angle lenses that encompass a reachable food source and the person's mouth without any need for aiming or moving the imaging members. Alternatively, an automatic-imaging member may sequentially and iteratively focus on the food source, then on the person's mouth, then back on the food source, and so forth.

In an example, this device can automatically adjust the imaging vectors or focal lengths of one or more imaging components so that these imaging components stay focused on a food source and/or the person's mouth. Even if the line of sight from an automatic-imaging member to a food source, or to the person's mouth, becomes temporarily obscured, the device can track the last-known location of the food source, or the person's mouth, and search near that location in space to re-identify the food source, or mouth, to re-establish imaging contact. In an example, the device may track movement of the food source, or the person's mouth, relative to the imaging device. In an example, the device may extrapolate expected movement of the food source, or the person's mouth, and search in the expected projected of the food source, or the person's mouth, in order to re-establish imaging contact. In various examples, this device and method may use face recognition and/or gesture recognition methods to track the location of the person's face and/or hand relative to a wearable imaging device.

In an example, this device and method comprise at least one camera (or other imaging member) that takes pictures along an imaging vector which points toward the person's mouth and/or face, during certain body configurations, while the person eats. In an example, this device and member uses face recognition methods to adjust the direction and/or focal length of its field of vision in order to stay focused on the person's mouth and/or face. Face recognition methods and/or gesture recognition methods may also be used to detect and measure hand-to-mouth proximity and interaction. In an example, one or more imaging devices automatically stay focused on the person's mouth, even if the device moves, by the use of face recognition methods. In an example, the fields of vision from one or more automatic-imaging members collectively encompass the person's mouth and a reachable food source, when the person eats, without the need for human intervention, when the person eats, because the imaging members remain automatically directed toward the person's mouth, toward the reachable food source, or both.

In various examples, movement of one or more automatic-imaging members allows their fields of vision to automatically and collectively capture images of the person's mouth and a reachable food source without the need for human intervention when the person eats. In an example, this device and method includes an automatic-imaging member that is worn on the person's wrist, hand, finger, or arm, such that this automatic-imaging member automatically takes pictures of the person's mouth, a reachable food source, or both as the person moves their arm and hand when they eat. This movement causes the fields of vision from one or more automatic-imaging members to collectively and automatically encompass the person's mouth and a reachable food source as the person eats. Accordingly, there is no need for human intervention, when the person starts eating, to manually aim a camera (or other imaging member) toward the person's mouth or toward a reachable food source. Picture taking of the person's mouth and the food source is automatic and virtually involuntary. This makes it relatively easy to incorporate tamper-resisting features into this invention.

In an example, one or more imaging members are worn on a body member that moves as food travels along the food consumption pathway. In this manner, these one or more imaging members have lines of sight to the person's mouth and to the food source during at least some points along the food consumption pathway. In various examples, this movement is caused by bending of the person's shoulder, elbow, and wrist joints. In an example, an imaging member is worn on the wrist, arm, or hand of a dominant arm, wherein the person uses this arm to move food along the food consumption pathway. In another example, an imaging member may be worn on the wrist, arm, or hand of a non-dominant arm, wherein this other arm is generally stationery and not used to move food along the food consumption pathway. In another example, automatic-imaging members may be worn on both arms.

In an example, this invention comprises two or more automatic-imaging members wherein a first imaging member is pointed toward the person's mouth most of the time, as the person moves their arm to move food along the food consumption pathway, and wherein a second imaging member is pointed toward a reachable food source most of the time, as the person moves their arm to move food along the food consumption pathway. In an example, this invention comprises one or more imaging members wherein: a first imaging member points toward the person's mouth at least once as the person brings a piece (or portion) of food to their mouth from a reachable food source; and a second imaging member points toward the reachable food source at least once as the person brings a piece (or portion) of food to their mouth from the reachable food source.

In an example, this device and method comprise an imaging device with a single imaging member that takes pictures along shifting imaging vectors, as food travels along the food consumption pathway, so that it take pictures of a food source and the person's mouth sequentially. In an example, this device and method takes pictures of a food source and a person's mouth from different positions as food moves along the food consumption pathway. In an example, this device and method comprise an imaging device that scans for, locates, and takes pictures of the distal and proximal endpoints of the food consumption pathway.

In an example of this invention, the fields of vision from one or more automatic-imaging members are shifted by movement of the person's arm and hand while the person eats. This shifting causes the fields of vision from the one or more automatic-imaging members to collectively and automatically encompass the person's mouth and a reachable food source while the person is eating. This encompassing imaging occurs without the need for human intervention when the person eats. This eliminates the need for a person to manually aim a camera (or other imaging member) toward their mouth or toward a reachable food source.

FIGS. 9-14 again show the example of this invention that was introduced in FIGS. 1-2. However, this example is now shown as functioning in a six-picture sequence of food consumption, involving multiple cycles of pieces (or portions) of food moving along the food consumption pathway until the food source is entirely consumed. In FIGS. 9-14, this device and method are shown taking pictures of a reachable food source and the person's mouth, from multiple perspectives, as the person eats until all of the food on a plate is consumed.

Figure 9:
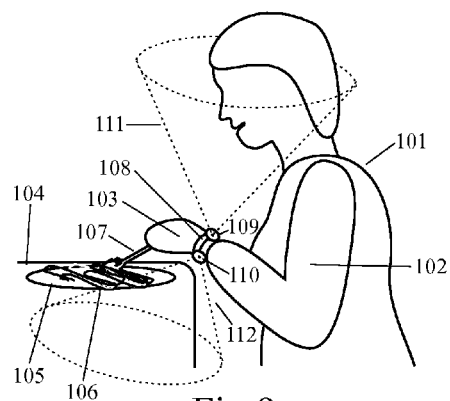

FIG. 9 starts this sequence by showing a person 101 engaging food 106 on plate 105 with utensil 107. The person moves utensil 107 by moving their arm 102 and hand 103. Wrist-mounted camera 109, on wrist band 108, has a field of vision 111 that encompasses the person's mouth. Wrist-mounted camera 110, also on wrist band 108, has a field of vision 112 that partially encompasses a reachable food source which, in this example, is food 106 on plate 105 on table 104.

Figure 10:
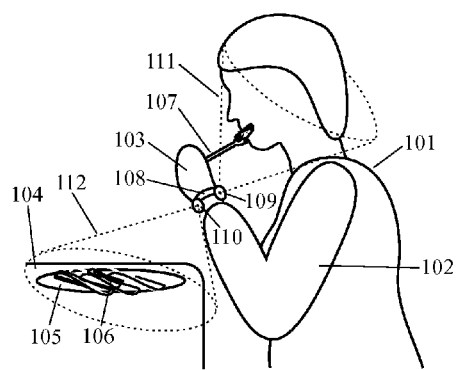
Figure 11:
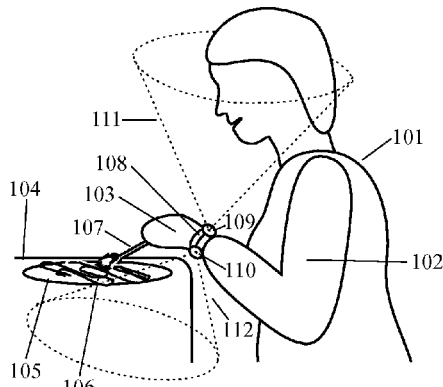
Figure 12:
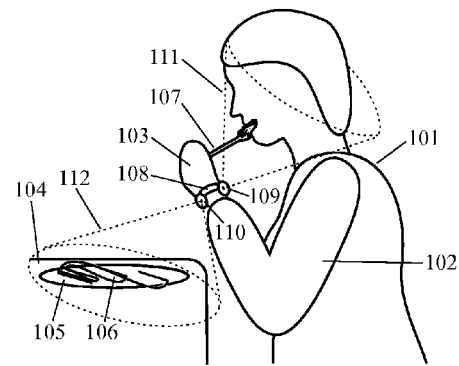
Figure 13:
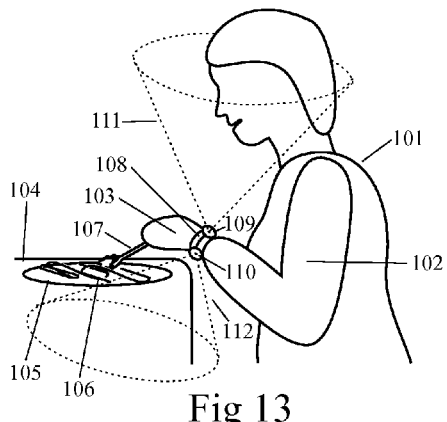
Figure 14:
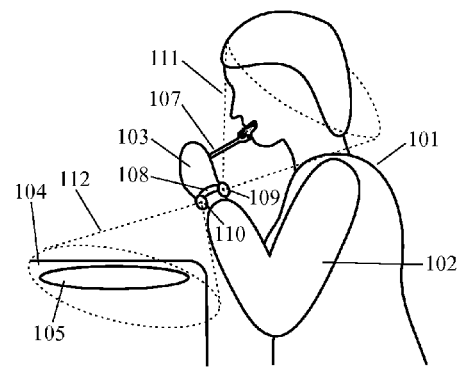

FIG. 10 continues this sequence by showing the person having bent their arm 102 and wrist 103 in order to move a piece of food up to their mouth via utensil 107. In FIG. 10, camera 109 has a field of vision 111 that encompasses the person's mouth (including the interaction of the person's mouth and the piece of food) and camera 110 has a field of vision 112 that now fully encompasses the food source.

FIGS. 11-14 continue this sequence with additional cycles of the food consumption pathway, wherein the person brings pieces of food from the plate 105 to the person's mouth. In this example, by the end of this sequence shown in FIG. 14 the person has eaten all of the food 106 from plate 105.

In the sequence of food consumption pathway cycles that is shown in FIGS. 9-14, pictures of the reachable food source (food 106 on plate 105) taken by camera 110 are particularly useful in identifying the types of food to which the person has reachable access. In this simple example, featuring a single person with a single plate, changes in the volume of food on the plate could also be used to estimate the quantities of food which this person consumes. However, with more complex situations featuring multiple people and multiple food sources, images of the food source only would be limited for estimating the quantity of food that is actually consumed by a given person.

In this example, the pictures of the person's mouth taken by camera 109 are particularly useful for estimating the quantities of food actually consumed by the person. Static or moving pictures of the person inserting pieces of food into their mouth, refined by counting the number or speed of chewing motions and the number of cycles of the food consumption pathway, can be used to estimate the quantity of food consumed. However, images of the mouth only would be limited for identifying the types of food consumed.

Integrated analysis of pictures of both the food source and the person's mouth can provide a relatively accurate estimate of the types and quantities of food actually consumed by this person, even in situations with multiple food sources and multiple diners. Integrated analysis can compare estimates of food quantity consumed based on changes in observed food volume at the food source to estimates of food quantity consumed based on mouth-food interaction and food consumption pathway cycles.

Although it is preferable that the field of vision 111 for camera 109 encompasses the person's mouth all the time and that the field of vision 111 for camera 110 encompasses the reachable food source all the time, integrated analysis can occur even if this is not possible. As long as the field of vision 112 for camera 110 encompasses the food source at least once during a food consumption pathway cycle and the field of vision 111 from camera 109 encompasses the person's mouth at least once during a food consumption pathway cycle, this device and method can extrapolate mouth-food interaction and also changes in food volume at the reachable food source.

Figure 15:
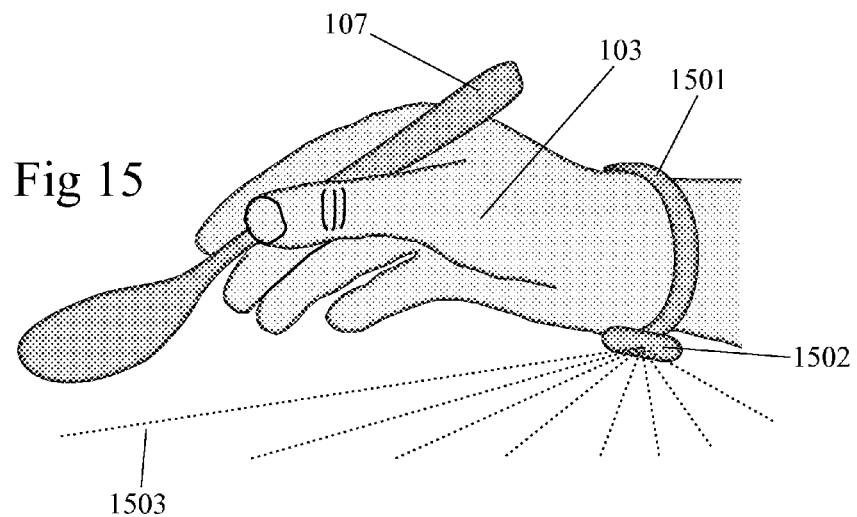
Figure 16:
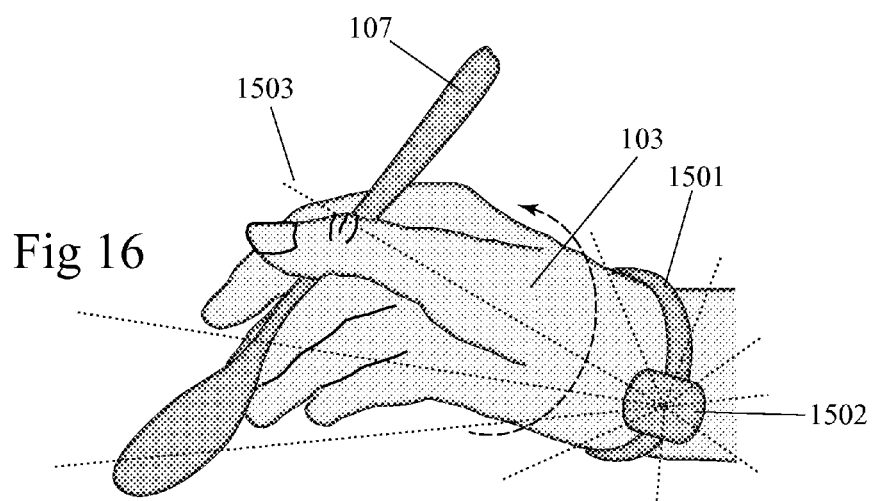

FIGS. 15 and 16 show, in greater detail, how the field of vision from a wrist-worn imaging member can advantageously shift as a person moves and rolls their wrist to bring food up to their mouth along the food consumption pathway. These figures show a person's hand 103 holding utensil 107 from the perspective of a person looking at their hand, as their hand brings the utensil up to their mouth. This rolling and shifting motion can enable a single imaging member, such as a single camera 1502 mounted on wrist band 1501, to take pictures of a reachable food source and the person's mouth, from different points along the food consumption pathway.

FIGS. 15 and 16 show movement of a single camera 1502 mounted on the anterior (inside) surface of wrist band 1501 as the person moves and rolls their wrist to bring utensil 107 up from a food source to their mouth. The manner in which this camera is worn is like a wrist watch, with a camera instead of a watch face, which has been rotated 180 degrees around the person's wrist. In FIG. 15, field of vision 1503 from camera 1502 points generally downward in a manner that would be likely to encompass a reachable food source which the person would engage with utensil 107. In FIG. 16, this field of vision 1503 has been rotated upwards towards the person's mouth by the rotation of the person's wrist as the person brings utensil 107 up to their mouth. These two figures illustrate an example wherein a single wrist-worn imaging member can take pictures of both a reachable food source and the person's mouth, due to the rolling motion of a person's wrist as food is moved along the food consumption pathway.

Figure 17:
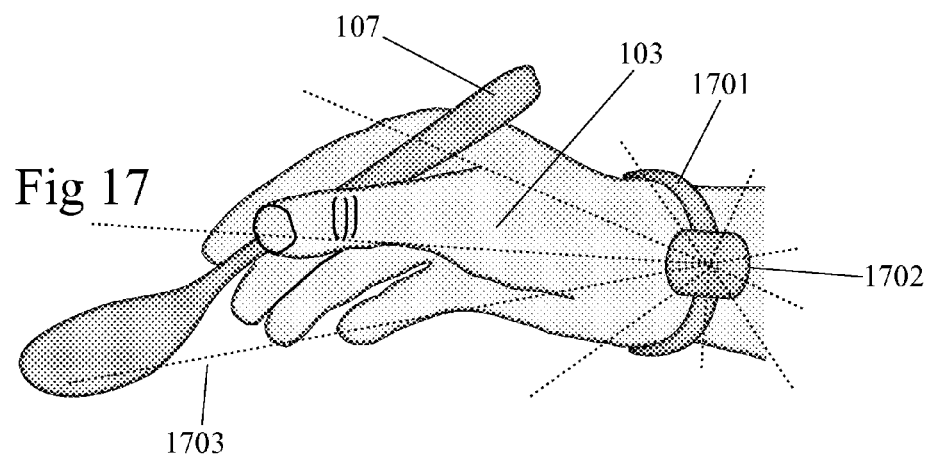
Figure 18:
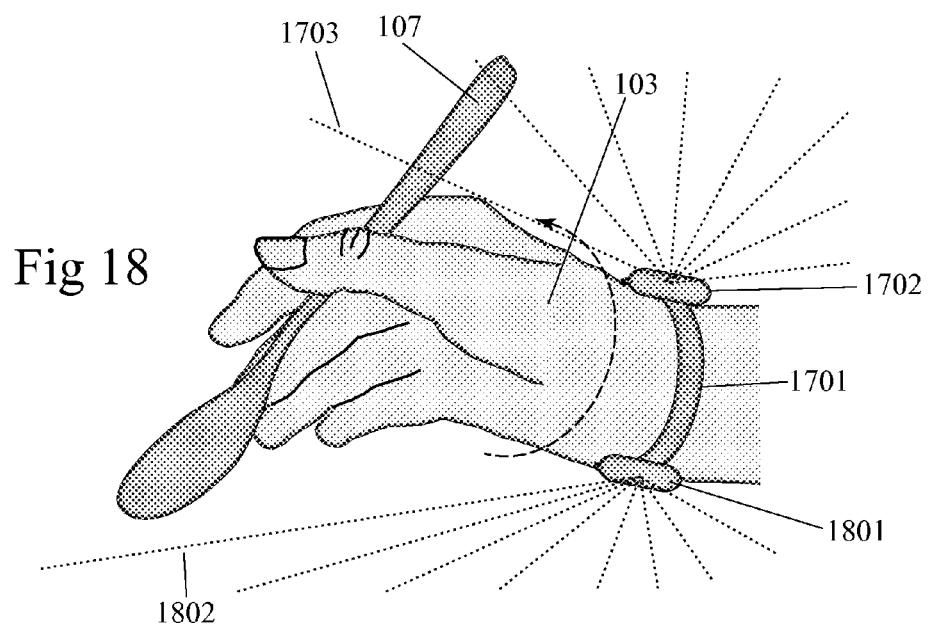

FIGS. 17 and 18 are similar to FIGS. 15 and 16, except that FIGS. 17 and 18 show a wrist-worn automatic-imaging member with two cameras, 1702 and 1801, instead of just one. This is similar to the example introduced in FIGS. 1 and 2. These figures show the person's hand 103 holding utensil 107 from the perspective of a person looking at their hand, as their hand brings the utensil up to their mouth. FIGS. 17 and 18 show how the rolling motion of the wrist, as food is moved along the food consumption pathway, enables a wrist-worn imaging member with two cameras, 1702 and 1801, to collectively and automatically take pictures of a reachable food source and a person's mouth.

The two cameras in FIGS. 17 and 18 are attached to the narrow sides of the person's wrist via wrist band 1701. Camera 1801 is not shown in FIG. 17 because it is on the far-side of the person's wrist which is not visible in FIG. 17. After the person's rolls their wrist to bring the utensil up toward their mouth, as shown in FIG. 18, camera 1801 comes into view. This rolling and shifting motion of the person's wrist, occurring between FIGS. 17 and 18, enables the two cameras, 1702 and 1801, to automatically and collectively take pictures of a reachable food source and the person's mouth, from different points along the food consumption pathway. In FIG. 17, field of vision 1703 from camera 1702 is directed toward the person's mouth. In FIG. 18, after the person has moved their arm and rotated their wrist, field of vision 1802 from camera 1801 is directed toward (the likely location of) a reachable food source. In an example, camera 1801 may scan the vicinity in order to detect and identify a reachable food source.

Having two cameras mounted on opposite sides of a person's wrist increases the probability of encompassing both the person's mouth and a reachable food source as the person rolls their wrist and bends their arm to move food along the food consumption pathway. In other examples, more than two cameras may be attached on a band around the person's wrist to further increase the probability of encompassing both the person's mouth and the reachable food source.

In an example, the location of one or more cameras may be moved automatically, independently of movement of the body member to which the cameras are attached, in order to increase the probability of encompassing both the person's mouth and a reachable food source. In an example, the lenses of one or more cameras may be automatically and independently moved in order to increase the probability of encompassing both the person's mouth and a reachable food source. In various examples, a lens may be automatically shifted or rotated to change the direction or focal length of the camera's field of vision. In an example, the lenses of one or more cameras may be automatically moved to track the person's mouth and hand. In an example, the lenses of one or more cameras may be automatically moved to scan for reachable food sources.

In an example, this device and method comprise a device that is worn on a person so as to take images of food, or pieces of food, at multiple locations as food travels along a food consumption pathway. In an example, this device and method comprise a device that takes a series of pictures of a portion of food as it moves along a food consumption pathway between a reachable food source and the person's mouth. In an example, this device and method comprise a wearable imaging member that takes pictures upwards toward a person's face as the person's arm bends when the person eats. In an example, this invention comprises an imaging member that captures images of the person's mouth when the person's elbow is bent at an angle between 40-140 degrees as the person brings food to their mouth. In various examples, this device and method automatically takes pictures of food at a plurality of positions as food moves along the food consumption pathway. In an example, this device and method estimates the type and quantity of food consumed based, at least partially, on pattern analysis of images of the proximal and distal endpoints of the food consumption pathway.

In an example, this invention comprises a human-energy input measuring device and method that includes a wearable imaging member that identifies the types and quantities of food consumed based on images of food from a plurality of points along a food consumption pathway. In an example, this device and method takes pictures of a person's mouth and a reachable food source from multiple angles, from an imaging member worn on a body member that moves as food travels along the food consumption pathway.

In an example, this invention comprises one or more of imaging devices which are worn on a location on the human body that provides at least one line of sight from the device to the person's mouth and at least one line of sight to a reachable food source, as food travels along the food consumption pathway. In various examples, these one or more imaging devices simultaneously or sequentially record images along at least two different vectors, one which points toward the mouth during at least some portion of the food consumption pathway and one which points toward the food source during at least some portion of the food consumption pathway. In various examples, this device and method comprise multiple imaging members that are worn on a person's wrist, hand, arm, or finger—with some imaging elements pointed toward the person's mouth from certain locations along the food consumption pathway and some imaging elements pointed toward a reachable food source from certain locations along the food consumption pathway.

Thus far in our description of the figures, we have discussed a variety of ways in which the automatic image-taking members and methods of this invention may be embodied. We now turn our attention to discuss, in greater detail, the automatic imaging-analyzing members and methods which are also an important part of this invention. This invention comprises a device and method that includes at least one image-analyzing member. This image-analyzing member automatically analyzes pictures of a person's mouth and pictures of a reachable food source in order to estimate the types and quantities of food consumed by this person. This is superior to prior art that only analyzes pictures of a reachable food source because the person might not actually consume all of the food at this food source.

In various examples, one or more methods to analyze pictures, in order to estimate the types and quantities of food consumed, can be selected from the group consisting of: pattern recognition; food recognition; word recognition; logo recognition; bar code recognition; face recognition; gesture recognition; and human motion recognition. In various examples, a picture of the person's mouth and/or a reachable food source may be analyzed with one or more methods selected from the group consisting of: pattern recognition or identification; human motion recognition or identification; face recognition or identification; gesture recognition or identification; food recognition or identification; word recognition or identification; logo recognition or identification; bar code recognition or identification; and 3D modeling. In an example, images of a person's mouth and a reachable food source may be taken from at least two different perspectives in order to enable the creation of three-dimensional models of food.

In various examples, this invention comprises one or more image-analyzing members that analyze one or more factors selected from the group consisting of: number and type of reachable food sources; changes in the volume of food observed at a reachable food source; number and size of chewing movements; number and size of swallowing movements; number of times that pieces (or portions) of food travel along the food consumption pathway; and size of pieces (or portions) of food traveling along the food consumption pathway. In various examples, one or more of these factors may be used to analyze images to estimate the types and quantities of food consumed by a person.

In an example, this invention is entirely automatic for both food imaging and food identification. In an example, this invention comprises a device and method that automatically and comprehensively analyzes images of food sources and a person's mouth in order to provide final estimates of the types and quantities of food consumed. In an example, the food identification and quantification process performed by this device and method does not require any manual entry of information, any manual initiation of picture taking, or any manual aiming of an imaging device when a person eats. In an example, this device and method automatically analyzes images to estimate the types and quantities of food consumed without the need for real-time or subsequent human evaluation.

In an example, this device identifies the types and quantities of food consumed based on: pattern recognition of food at a reachable food source; changes in food at that source; analysis of images of food traveling along a food consumption pathway from a food source to the person's mouth; and/or the number of cycles of food moving along the food consumption pathway. In various examples, food may be identified by pattern recognition of food itself, by recognition of words on food packaging or containers, by recognition of food brand images and logos, or by recognition of product identification codes (such as "bar codes"). In an example, analysis of images by this device and method occurs in real time, as the person is consuming food. In an example, analysis of images by this device and method occurs after the person has consumed food.

In another example, this invention is partially automatic and partially refined by human evaluation or interaction. In an example, this device and method comprise a device and method that automatically analyzes images of food sources and a person's mouth in order to provide initial estimates of the types and quantities of food consumed. These initial estimates are then refined by human evaluation and/or interaction. In an example, estimation of the types and quantities of food consumed is refined or enhanced by human interaction and/or evaluation.

For example, the device may prompt the person with clarifying questions concerning the types and quantities of food that person has consumed. These questions may be asked in real time, as a person eats, at a subsequent time, or periodically. In an example, this device and method may prompt the person with queries to refine initial automatically-generated estimates of the types and quantities of food consumed. Automatic estimates may be refined by interaction between the device and the person. However, such refinement should have limits and safeguards to guard against possible tampering. For example, the device and method should not allow a person to modify automatically-generated initial estimates of food consumed to a degree that would cause the device and method to under-estimate caloric intake.

In an example, analysis of food images and estimation of food consumed by this device and method may be entirely automatic or may be a mixture of automated estimates plus human refinement. Even a partially-automated device and method for calorie monitoring and estimation is superior to prior art that relies completely on manual calorie counting or manual entry of food items consumed. In an example, the estimates of the types and quantities of food consumed that are produced by this invention are used to estimate human caloric intake. In an example, images of a person's mouth, a reachable food source, and the interaction between the person's mouth and food are automatically, or semi-automatically, analyzed to estimate the types of quantities of food that the person eats. These estimates are, in turn, used to estimate the person's caloric intake.

In an example, the caloric intake estimation provided by this device and method becomes the energy-input measuring component of an overall system for energy balance and weight management. In an example, the device and method can estimate the energy-input component of energy balance. In an example, this invention comprises an automatic and tamper-resistant device and method for estimating human caloric intake.

In an example, the device and method for estimating human caloric intake that is disclosed herein may be used in conjunction with a device and method for estimating human caloric output and/or human energy expenditure. In an example, this present invention can be used in combination with a wearable and mobile energy-output-measuring component that automatically records and analyses images in order to detect activity and energy expenditure. In an example, this present invention may be used in combination with a wearable and mobile device that estimates human energy output based on patterns of acceleration and movement of body members. In an example, this invention may be used in combination with an energy-output-measuring component that estimates energy output by measuring changes in the position and configuration of a person's body.

In an example, this invention may be incorporated into an overall device, system, and method for human energy balance and weight management. In an example, the estimates of the types and quantities of food consumed that are provided by this present invention are used to estimate human caloric intake. These estimates of human caloric intake are then, in turn, used in combination with estimates of human caloric expenditure as part of an overall system for human energy balance and weight management. In an example, estimates of the types and quantities of food consumed are used to estimate human caloric intake and wherein these estimates of human caloric intake are used in combination with estimates of human caloric expenditure as part of an overall system for human energy balance and human weight management.

This invention can include an optional analytic component that analyzes and compares human caloric input vs. human caloric output for a particular person as part of an overall device, system, and method for overall energy balance and weight management. This overall device, system, and method may be used to help a person to lose weight or to maintain a desirable weight. In an example, this device and method can be used as part of a system with a human-energy input measuring component and a human-energy output measuring component. In an example, this invention is part of an overall system for energy balance and weight management.

Thus far in our description of the figures, we have repeatedly described this invention as being tamper resistant, but have not shown details of how tamper-resistant features could be embodied. We now show and discuss, in some detail, some of the specific ways in which this device and method for monitoring and measuring caloric intake can be made tamper resistant. This invention advantageously can be made tamper-resistant because the imaging members are wearable and can operate in an automatic manner.

In an example, this invention includes one or more automatic-imaging members that collectively and automatically take pictures of the person's mouth and pictures of a reachable food source, when the person eats, without the need for human intervention, when the person eats, to activate picture taking. In an example, these one or more automatic-imaging members take pictures continually. In an example, these one or more automatic-imaging members are automatically activated to take pictures when a person eats based on a sensor selected from the group consisting of: accelerometer, inclinometer, motion sensor, sound sensor, smell sensor, blood pressure sensor, heart rate sensor, EEG sensor, ECG sensor, EMG sensor, electrochemical sensor, gastric activity sensor, GPS sensor, location sensor, image sensor, optical sensor, piezoelectric sensor, respiration sensor, strain gauge, electrogoniometer, chewing sensor, swallow sensor, temperature sensor, and pressure sensor.

In an example, the fields of vision from these one or more automatic-imaging members collectively and automatically encompass the person's mouth and a reachable food source, when the person eats, without the need for human intervention, when the person eats, to manually aim an imaging member toward the person's mouth or toward the reachable food source. In an example, the fields of vision from one or more automatic-imaging members are moved as the person moves their arm when the person eats; and wherein this movement causes the fields of vision from one or more automatic-imaging members to collectively and automatically encompass the person's mouth and a reachable food source, when the person eats, without the need for human intervention, when the person eats, to manually aim an imaging member toward the person's mouth or toward the reachable food source.

In an example, these one or more automatic-imaging members are worn on one or more body members selected from the group consisting of the person's wrist, hand, arm, and finger; wherein the fields of vision from one or more automatic-imaging members are moved as the person moves their arm when the person eats; and wherein this movement causes the fields of vision from one or more automatic-imaging members to collectively and automatically encompass the person's mouth and a reachable food source, when the person eats, without the need for human intervention, when the person eats, to manually aim an imaging member toward the person's mouth or toward the reachable food source.

FIGS. 19-21 show one example of how this invention can be made tamper resistant. FIGS. 19-21 show a person, 1901, who can access a reachable food source 1905 (food in a bowl, in this example), on table 1906, by moving their arm 1903 and hand 1904. In this example, the person 1901 is wearing a wrist-based automatic-imaging member 1907 with field of vision 1908. In FIG. 19, this wrist-based automatic-imaging member 1907 is functioning properly because the field of vision 1908 from of this automatic-imaging member 1907 has an unobstructed line of sight to the person's mouth 1902. This imaging member can monitor the person's mouth 1902 to detect if the person is eating and then analyze pictures to estimate the quantity of food consumed.

In FIG. 19, automatic-imaging member 1907 recognizes that the line of sight to the person's mouth is unobstructed because it recognizes the person's mouth using face recognition methods. In other examples, automatic-imaging member 1907 may recognize that the line of sight to the person's mouth is unobstructed by using other pattern recognition or imaging-analyzing means. As long as a line of sight from the automatic-imaging member to the person's mouth is maintained (unobstructed), the device and method can detect if the person starts eating and, in conjunction with images of the reachable food source, it can estimate caloric intake based on quantities and types of food consumed.

In FIG. 20, person 1901 has bent their arm 1903 and moved their hand 1904 in order to bring a piece of food from the reachable food source 1905 up to their mouth 1902. In this example, the piece of food is clutched (hidden) in the person's hand as it travels along the food consumption pathway. In this example, the automatic-imaging member 1907 used face recognition methods to track the relative location of the person's mouth 1902 and has shifted its field of vision 1908 in order to maintain the line of sight to the person's mouth. As long as this line of sight is maintained, this mouth-imaging component of this device and method for estimating caloric intake can function properly.

In FIG. 21, however, the functioning of this imaging member 1907 has been impaired. This impairment may be intentional tampering by the person or it may be accidental. In either event, the device and method detects and responds to the impairment in order to correct the impairment. In FIG. 21, the sleeve of the person's shirt has slipped down over the automatic-imaging device, obstructing the line of sight from the imaging device 1907 to the person's mouth 1902. Thus covered, the obstructed automatic-imaging member cannot function properly. In this example, the automatic-imaging member recognizes that its line of sight to the person's mouth has been lost. In an example, it may recognize this by using face recognition methods. When the person's face is no longer found at an expected location (or nearby), then the device and method recognizes that its functioning is impaired.

Without a line of sight to the person's mouth in FIG. 21, the wrist-worn automatic-imaging device 1907 no longer works properly to monitor and estimate caloric intake. In response, automatic-imaging device 1907 gives a response 2101 that is represented in FIG. 21 by a lightning bolt symbol. In an example, this response 2101 may be an electronic buzzing sound or a ring tone. In another example, response 2101 may include vibration of the person's wrist. In another example, response 2101 may be transmission or a message to a remote location or monitor. In various examples, this invention detects and responds to loss of imaging functionality in a manner that helps to restore proper imaging functionality. In this example, response 2101 prompts the person to move their shirt sleeve upwards to uncover the wrist-worn imaging member 1904 so that this imaging member can work properly once again.

In an example, the line of sight from an automatic-imaging member to the person's mouth may be obstructed by an accidental event, such as the accidental downward sliding of the person's shirt sleeve. In another example, the line of sight from the automatic-imaging member to the person's mouth may be intentionally obstructed by the person. Technically, only the second type of causation should be called "tampering" with the operation of the device and method. However, one can design tamper-resisting features for operation of the device and method that detect and correct operational impairment whether this impairment is accidental or intentional. The device can be designed to detect if the automatic-imaging function is obstructed, or otherwise impaired, and to respond accordingly to restore functionality.

One example of a tamper-resistant design is for the device to constantly monitor the location of the person's mouth and to respond if a line of sight to the person's mouth is ever obstructed. Another example of a tamper-resistant design is for the device to constantly scan and monitor space around the person, especially space in the vicinity of the person's hand, to detect possible reachable food sources. In a variation on these examples, a device may only monitor the location of the person's mouth, or scan for possible reachable food sources, when one or more sensors indicate that the person is probably eating. These one or more sensors may be selected from the group consisting of: accelerometer, inclinometer, motion sensor, pedometer, sound sensor, smell sensor, blood pressure sensor, heart rate sensor, EEG sensor, ECG sensor, EMG sensor, electrochemical sensor, gastric activity sensor, GPS sensor, location sensor, image sensor, optical sensor, piezoelectric sensor, respiration sensor, strain gauge, electrogoniometer, chewing sensor, swallow sensor, temperature sensor, and pressure sensor.

In an example, this invention can be embodied in a tamper-resistant device that automatically monitors caloric intake comprising: one or more automatic-imaging members that are worn on one or more locations on a person from which these members: collectively and automatically take pictures of the person's mouth when the person eats and pictures of a reachable food source when the person eats; wherein a reachable food source is a food source that the person can reach by moving their arm; and wherein food can include liquid nourishment as well as solid food; a tamper-resisting mechanism which detects and responds if the operation of the one or more automatic-imaging members is impaired; and an image-analyzing member which automatically analyzes pictures of the person's mouth and pictures of the reachable food source in order to estimate the types and quantities of food that are consumed by the person.

Figure 22:
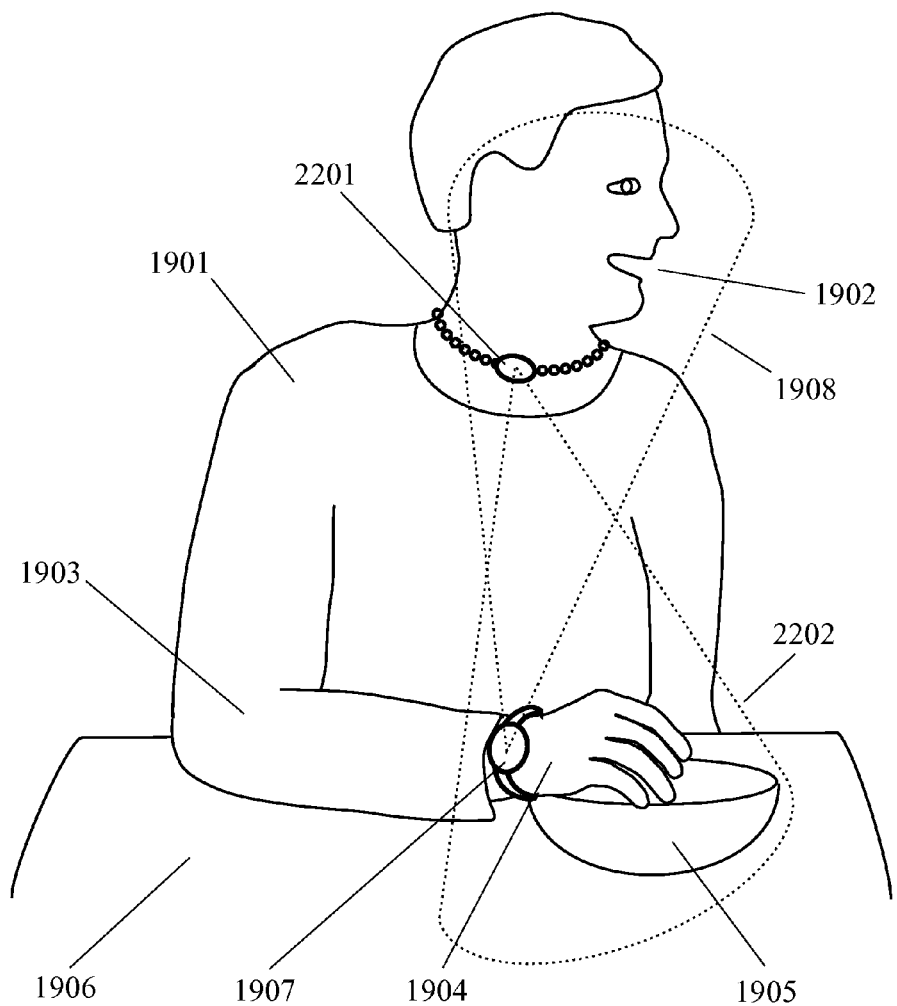

FIG. 22 shows another example of how this invention may be embodied a tamper-resisting device and method to automatically monitor and measure caloric intake. In FIG. 22, this device and method comprise two wearable automatic-imaging members. The first automatic-imaging member, 1907, is worn on a person's wrist like a wrist watch. This first member takes pictures of the person's mouth and detects if the line of sight from this first imaging member to the person's mouth is obstructed or otherwise impaired. The second automatic-imaging member, 2201, is worn on a person's neck like a necklace. This second member takes pictures of the person's hand and a reachable food source and detects if the line of sight from the second imaging member to the person's hand and a reachable food source is obstructed or otherwise impaired. In this example, this device and method is tamper-resistant because it detects and responds if either of these lines of sight are obstructed or otherwise impaired.

Discussing FIG. 22 in further detail, this figure shows person 1901 accessing reachable food source (e.g. a bowl of food) 1905 on table 1906 by moving their arm 1903 and hand 1904. Person 1901 wears a first automatic-imaging member 1907 around their wrist. From its wrist-worn location, this first imaging member 1907 has a field of vision 1908 that encompasses the person's mouth 1902. In an example, this automatic-imaging member 1907 uses face recognition to shift its field of vision 1907, as the person moves their wrist or head, so as to maintain a line of sight from the wrist to the person's mouth. In an example, the field of vision 1907 may be shifted by automatic rotation or shifting of the lens on automatic-imaging member 1907.

In an example, first automatic-imaging member 1907 constantly maintains a line of sight to the person's mouth by constantly shifting the direction and/or focal length of its field of vision 1908. In another example, this first automatic-imaging member 1907 scans and acquires a line of sight to the person's mouth only when a sensor indicates that the person is eating. In an example, this scanning function may comprise changing the direction and/or focal length of the member's field of vision 1908. If the line of sight from this member to the person's mouth is obstructed, or otherwise impaired, then this device and method detects and responds to this impairment as part of its tamper-resisting function. In an example, its response to tampering helps to restore proper imaging function for automatic monitoring and estimation of caloric intake.

In this example, this person 1901 also wears a second automatic-imaging member 2201 around their neck. In this example, automatic-imaging member 2201 is worn like a central pendant on the front of a necklace. From this location, this second imaging member has a forward-and-downward facing field of vision, 2202, that encompasses the person's hand 1904 and a reachable food source 1905. In an example, this second automatic-imaging member 2201 uses gesture recognition, or other pattern recognition methods, to shift its focus so as to always maintain a line of sight to the person's hand and/or to scan for potential reachable food sources.

In an example, this second automatic-imaging member 2201 constantly maintains a line of sight to one or both of the person's hands. In another example, this second automatic-imaging member 2201 scans for (and identifies and maintains a line of sight to) the person's hand only when a sensor indicates that the person is eating. In another example, this second automatic-imaging member 2201 scans for, acquires, and maintains a line of sight to a reachable food source only when a sensor indicates that the person is probably eating. In various examples, the sensors used to activate one or more of these automatic-imaging members may be selected from the group consisting of: accelerometer, inclinometer, motion sensor, pedometer, sound sensor, smell sensor, blood pressure sensor, heart rate sensor, EEG sensor, ECG sensor, EMG sensor, electrochemical sensor, gastric activity sensor, GPS sensor, location sensor, image sensor, optical sensor, piezoelectric sensor, respiration sensor, strain gauge, electrogoniometer, chewing sensor, swallow sensor, temperature sensor, and pressure sensor.

In an example, this device and method comprise one or more imaging members that scan nearby space in order to identify a person's mouth, hand, and/or reachable food source in response to sensors indicating that the person is probably eating. In an example, one of these imaging members: (a) scans space surrounding the imaging member in order to identify the person's hand and acquire a line of sight to the person's hand when a sensor indicates that the person is eating; and then (b) scans space surrounding the person's hand in order to identify and acquire a line of sight to any reachable food source near the person's hand. In an example, the device and method may concentrate scanning efforts on the person's hand at the distal endpoint of a food consumption pathway to detect and identify a reachable food source. If the line of sight from this imaging member to the person's hand and/or a reachable food source is subsequently obstructed or otherwise impaired, then this device and method detects and responds as part of its tamper-resisting features. In an example, this response is designed to restore imaging functionality to enable proper automatic monitoring and estimation of caloric intake.

More generally, in various examples, this invention includes one or more tamper-resisting mechanisms which detect and respond if the operation of one or more automatic-imaging members are obstructed or otherwise impaired. In an example, this invention includes a tamper-resisting mechanism which detects and responds if a person hinders the operation of one or more automatic-imaging members. For example, the device and method disclosed herein can have a tamper-resistant feature that is triggered if the device is removed from the body member as indicated by a sensor selected from the group consisting of: accelerometer, inclinometer, motion sensor, pedometer, sound sensor, smell sensor, blood pressure sensor, heart rate sensor, EEG sensor, ECG sensor, EMG sensor, electrochemical sensor, gastric activity sensor, GPS sensor, location sensor, image sensor, optical sensor, piezoelectric sensor, respiration sensor, strain gauge, electrogoniometer, chewing sensor, swallow sensor, temperature sensor, and pressure sensor.

In an example, this invention comprises a device and method with features that resist tampering with the automatic and involuntary estimation of the types and quantities of food consumed by a person. In an example, this device and method includes an alarm that is triggered if a wearable imaging device is covered up. In various examples, this invention comprises one or more imaging devices which detect and respond if their direct line of sight with the person's mouth or a reachable food source is impaired. In an example, this invention includes a tamper-resisting member that monitors a person's mouth using face recognition methods and responds if the line of sight from an automatic-imaging member to the person's mouth is impaired when a person eats. In another example, this invention includes a tamper-resisting member that detects and responds if the person's actual weight gain or loss is inconsistent with predicted weight gain or loss. Weight gain or loss may be predicted by the net balance of estimated caloric intake and estimated caloric expenditure.

The tamper-resisting features of this invention help to make the operation of this invention relatively automatic, tamper-resistant, and virtually involuntary. This ensures comprehensive and accurate monitoring and measuring of caloric intake.

In an example, this invention can include at least two automatic-imaging members worn on a person's body, wherein the field of vision from a first automatic-imaging member automatically encompasses the person's mouth as the person eats, and wherein the field of vision from a second automatic-imaging member automatically encompasses a reachable food source as the person eats.

In an example, this invention can include at least two automatic-imaging members worn on a person's body: wherein a first automatic-imaging member is worn on a body member selected from the group consisting of the person's wrist, hand, lower arm, and finger; wherein the field of vision from the first automatic-imaging member automatically encompasses the person's mouth as the person eats; wherein a second automatic-imaging member is worn on a body member selected from the group consisting of the person's neck, head, torso, and upper arm; and wherein the field of vision from the second automatic-imaging member automatically encompasses a reachable food source as the person eats.

In an example, this invention can include a tamper-resisting member that comprises a sensor that detects and responds if an automatic-imaging member is removed from the person's body, wherein this sensor is selected from the group consisting of: accelerometer, inclinometer, motion sensor, pedometer, sound sensor, smell sensor, blood pressure sensor, heart rate sensor, EEG sensor, ECG sensor, EMG sensor, electrochemical sensor, gastric activity sensor, GPS sensor, location sensor, image sensor, optical sensor, piezoelectric sensor, respiration sensor, strain gauge, electrogoniometer, chewing sensor, swallow sensor, temperature sensor, and pressure sensor.

In an example, this invention can include a tamper-resisting member that comprises a sensor that detects and responds if the line of sight from one or more automatic-imaging members to the person's mouth or to a food source is impaired when a person is probably eating based on a sensor, wherein this sensor is selected from the group consisting of: accelerometer, inclinometer, motion sensor, pedometer, sound sensor, smell sensor, blood pressure sensor, heart rate sensor, EEG sensor, ECG sensor, EMG sensor, electrochemical sensor, gastric activity sensor, GPS sensor, location sensor, image sensor, optical sensor, piezoelectric sensor, respiration sensor, strain gauge, electrogoniometer, chewing sensor, swallow sensor, temperature sensor, and pressure sensor.

In an example, this invention can include a tamper-resisting member that monitors a person's mouth using face recognition methods and responds if the line of sight from an automatic-imaging member to the person's mouth is impaired when a person is probably eating based on a sensor, wherein this sensor is selected from the group consisting of: accelerometer, inclinometer, motion sensor, pedometer, sound sensor, smell sensor, blood pressure sensor, heart rate sensor, EEG sensor, ECG sensor, EMG sensor, electrochemical sensor, gastric activity sensor, GPS sensor, location sensor, image sensor, optical sensor, piezoelectric sensor, respiration sensor, strain gauge, electrogoniometer, chewing sensor, swallow sensor, temperature sensor, and pressure sensor.

In an example, this invention can include a tamper-resisting member that detects and responds if the person's actual weight gain or loss is inconsistent with the predicted weight gain or loss predicted by the combination of the estimated caloric intake and the estimated caloric expenditure.

In an example, this invention can be embodied in a tamper-resistant device that automatically monitors caloric intake comprising: one or more automatic-imaging members that are worn on one or more locations on a person from which these members: collectively and automatically take pictures of the person's mouth when the person eats and take pictures of a reachable food source when the person eats; wherein a reachable food source is a food source that the person can reach by moving their arm; wherein food can include liquid nourishment as well as solid food; wherein one or more automatic-imaging members collectively and automatically take pictures of the person's mouth and pictures of a reachable food source, when the person eats, without the need for human intervention, when the person eats, to activate picture taking; and wherein the fields of vision from one or more automatic-imaging members collectively and automatically encompass the person's mouth and a reachable food source, when the person eats, without the need for human intervention, when the person eats, to manually aim an imaging member toward the person's mouth or toward the reachable food source; a tamper-resisting mechanism which detects and responds if the operation of the one or more automatic-imaging members is impaired; wherein a tamper-resisting member comprises a sensor that detects and responds if the line of sight from one or more automatic-imaging members to the person's mouth or to a food source is impaired when a person is probably eating based on a sensor, wherein this sensor is selected from the group consisting of: accelerometer, inclinometer, motion sensor, pedometer, sound sensor, smell sensor, blood pressure sensor, heart rate sensor, EEG sensor, ECG sensor, EMG sensor, electrochemical sensor, gastric activity sensor, GPS sensor, location sensor, image sensor, optical sensor, piezoelectric sensor, respiration sensor, strain gauge, electrogoniometer, chewing sensor, swallow sensor, temperature sensor, and pressure sensor; and an image-analyzing member which automatically analyzes pictures of the person's mouth and pictures of the reachable food source in order to estimate not just what food is at the reachable food source, but the types and quantities of food that are actually consumed by the person; and wherein the image-analyzing member uses one or more methods selected from the group consisting of: pattern recognition or identification; human motion recognition or identification; face recognition or identification; gesture recognition or identification; food recognition or identification; word recognition or identification; logo recognition or identification; bar code recognition or identification; and 3D modeling.

In an example, this invention can be embodied in a tamper-resistant method for automatically monitoring caloric intake comprising: having a person wear one or more automatic-imaging members at one or more locations on the person from which these members collectively and automatically take pictures of the person's mouth when the person eats and pictures of a reachable food source when the person eats; wherein a reachable food source is a food source that the person can reach by moving their arm; and wherein food can include liquid nourishment as well as solid food; detecting and responding if the operation of the one or more automatic-imaging members is impaired; and automatically analyzing pictures of the person's mouth and pictures of the reachable food source in order to estimate the types and quantities of food that are consumed by the person.

FIGS. 23-30 show two four-frame series of pictures taken by a rough prototype of this invention that was worn on a person's wrist. These four-frame picture series capture movement of the field of vision from two cameras, as the person's arm and hand moved to transport food along the food consumption pathway. These pictures have been transformed from gradient full-color images into black-and-white dot images in order to conform to the figure requirements for a U.S. patent. In practice, these pictures would likely be analyzed as full-gradient full-color images for optimal image analysis and pattern recognition.

FIGS. 23-26 show a four-frame series of pictures taken by the moving field of vision from a first camera that was worn on the anterior surface of the person's wrist, like a wrist watch. This first camera generally pointed away from the person's face and toward a reachable food source as the person moved their arm and hand to transport food along the food consumption pathway. This first camera had an imaging vector that was generally perpendicular to the longitudinal bones of the person's upper arm.

Figure 23:
Figure 24:
Figure 25:
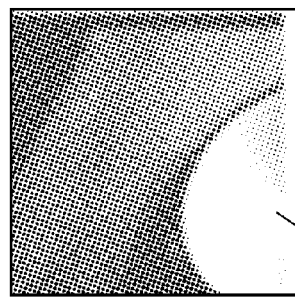
Figure 26:
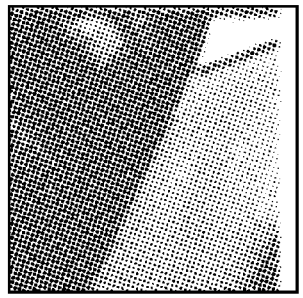

FIG. 23 shows the picture taken by this first camera at the distal endpoint of the food consumption pathway. This first picture shows a portion of a bowl, 2301, which represents a reachable food source. FIGS. 24-26 show subsequent pictures in this series taken by the first camera as the person moved their arm and hand so as to move food up to their mouth along the food consumption pathway. FIGS. 24 and 25 provide additional pictures of portions of the bowl 2301. In FIG. 26, the bowl is no longer in the field of vision of the camera at the proximal endpoint of the food consumption pathway. It is important to note that this camera worn on the person's wrist automatically encompasses the reachable food source in its field of vision as the arm and hand move food along the food consumption pathway, without any need for manual aiming or activation of the camera.

In the figures shown here, bowl 2301 represents a reachable food source, but no actual food is shown in it. In practice, bowl 2301 would have food in it. This device and method would analyze the series of pictures of food in the bowl (in FIGS. 23-25) in order to identify the type, and estimate the volume, of food in the bowl—in conjunction with images of the person's mouth and interaction between the person's mouth and food. In this example, the reachable food source is food in a bowl. In other examples, the reachable food source may be selected from the group consisting of: food on a plate, food in a bowl, food in a glass, food in a cup, food in a bottle, food in a can, food in a package, food in a container, food in a wrapper, food in a bag, food in a box, food on a table, food on a counter, food on a shelf, and food in a refrigerator.

FIGS. 27-30 show a four-frame series of pictures taken by the moving field of vision from a second camera that was also worn on the anterior surface of the person's wrist, like a wrist watch. However, this second camera generally pointed toward the person's face and away from a reachable food source as the person moved their arm and hand to transport food along the food consumption pathway. Like the first camera, this second camera had an imaging vector that was generally perpendicular to the longitudinal bones of the person's upper arm. However, this second camera had an imaging vector that was rotated 180 degrees around the person's wrist as compared to the imaging vector of the first camera.

Figure 27:
Figure 28:
Figure 29:
Figure 30:

FIG. 27 shows the picture taken by this first camera at the distal endpoint of the food consumption pathway. This first picture does not include the person's mouth. However, as the person moves their arm and hand upwards during the food consumption pathway, this second camera did capture images of the person's mouth, 2701, as shown in FIGS. 28 and 29. In FIG. 30, the person's mouth is no longer in the field of vision of the camera at the proximal endpoint of the food consumption pathway. This second camera, worn on the person's wrist, automatically encompasses the person's mouth in its field of vision as the arm and hand moves food along the food consumption pathway, without any need for manual aiming or activation of the camera.

The pictures shown in FIGS. 23-30 are only one example of the types of pictures that can be taken by an embodiment of this invention. This embodiment is only a rough prototype comprising a wrist-worn imaging member with two opposite-facing cameras that are perpendicular to the bones of the person's upper arm. As described previously in this description of the figures, there are many variations and refinements that could improve the ability of one or more automatic-imaging members to automatically and collectively encompass a reachable food source and a person's mouth while they eat.

However, even these simple pictures from a rough prototype provide encouraging preliminary evidence that this invention can work. This is early evidence that this invention can comprise one or more wearable automatic-imaging devices that automatically and collectively take pictures of a reachable food source and the person's mouth, when the person eats, without the need for manual aiming or picture activation, when the person eats. These pictures can then be analyzed to estimate the types and quantities of food consumed which, in turn, are used to estimate the person's caloric intake. The relatively automatic, tamper-resistant, and involuntary characteristics of this device and method make it superior to the prior art for monitoring and measuring caloric intake.

I claim:

1. A tamper-resistant wearable device that automatically monitors caloric intake comprising:
    a motion sensor which is configured to be worn on the person's wrist;
    a camera which is configured to be worn on a person's wrist, wherein the field of view of this camera is automatically moved based on data from the motion sensor so that the camera automatically takes pictures of the person's mouth when the person eats and automatically takes pictures of a reachable food source when the person eats, wherein a reachable food source is a food source that the person can reach by moving their arm; and wherein food can include liquid nourishment as well as solid food;
    a tamper-resisting mechanism, wherein this tamper-resisting mechanism detects when the camera is removed from the person's body, and wherein this tamper-resisting mechanism further detects when the field of view of this camera does not include the person's mouth when the person eats and/or a reachable food source when the person eats; and
    a computer which automatically analyzes pictures of the person's mouth and pictures of the reachable food source in order to estimate the types and quantities of food that are consumed by the person.

2. The device in claim 1 wherein the camera automatically takes pictures of the person's mouth and pictures of a reachable food source, when the person eats, without the need for human intervention, when the person eats, to activate picture taking.

3. The device in claim 1 wherein the camera takes pictures continually.

4. The device in claim 1 wherein the camera is automatically activated to take pictures when a person eats based on a sensor selected from the group consisting of: accelerometer, inclinometer, motion sensor, sound sensor, smell sensor, blood pressure sensor, heart rate sensor, EEG sensor, ECG sensor, EMG sensor, electrochemical sensor, gastric activity sensor, GPS sensor, location sensor, image sensor, optical sensor, piezoelectric sensor, respiration sensor, strain gauge, electrogoniometer, chewing sensor, swallow sensor, temperature sensor, and pressure sensor.

5. The device in claim 1 wherein the field of vision from the camera automatically encompasses the person's mouth and a reachable food source, when the person eats, without the need for human intervention, when the person eats, to manually aim the camera toward the person's mouth or toward the reachable food source.

6. The device in claim 1: wherein the field of vision from the camera is moved as the person moves their arm when the person eats; and wherein this movement causes the field of vision from the camera to automatically encompass the person's mouth and a reachable food source, when the person eats, without the need for human intervention, when the person eats, to manually aim the camera toward the person's mouth or toward the reachable food source.

7. A tamper-resistant wearable device that automatically monitors caloric intake comprising:
- a motion sensor which is configured to be worn on the person's wrist;
- a first camera which is configured to be worn on a first narrow side of a person's wrist at a location where a conventional wrist-watch face which was originally on the anterior surface of the wrist would wind up after that face has been rotated 90 degrees around the person's wrist;
- a second camera which is configured to be worn on a second narrow side of a person's wrist at a location which is located on the opposite side of the wrist from the first narrow side;
- a tamper-resisting mechanism, wherein this tamper-resisting mechanism detects when the cameras are removed from the person's body, and wherein this tamper-resisting mechanism detects when the field of view of the first camera does not include the person's mouth and/or the field of view of the second camera does not include a reachable food source when the person eats; and
- a computer which automatically analyzes pictures of the person's mouth and pictures of the reachable food source in order to estimate the types and quantities of food that are consumed by the person.

8. The device in claim 7 wherein the motion sensor is selected from the group consisting of: accelerometer, gyroscope, and inclinometer.

9. The device in claim 7 wherein a third camera is worn on a body member selected from the group consisting of the person's neck, head, torso, and upper arm; and wherein the field of vision from the third camera automatically encompasses a reachable food source as the person eats.

10. The device in claim 7 wherein a tamper-resisting mechanism comprises a sensor that detects and responds if a camera is removed from the person's body, wherein this sensor is selected from the group consisting of: accelerometer, inclinometer, motion sensor, pedometer, sound sensor, smell sensor, blood pressure sensor, heart rate sensor, EEG sensor, ECG sensor, EMG sensor, electrochemical sensor, gastric activity sensor, GPS sensor, location sensor, image sensor, optical sensor, piezoelectric sensor, respiration sensor, strain gauge, electrogoniometer, chewing sensor, swallow sensor, temperature sensor, and pressure sensor.

11. The device in claim 7 wherein a tamper-resisting mechanism comprises a sensor that detects and responds if the line of sight to the person's mouth or to a food source is impaired when a person is probably eating based on a sensor, wherein this sensor is selected from the group consisting of: accelerometer, inclinometer, motion sensor, pedometer, sound sensor, smell sensor, blood pressure sensor, heart rate sensor, EEG sensor, ECG sensor, EMG sensor, electrochemical sensor, gastric activity sensor, GPS sensor, location sensor, image sensor, optical sensor, piezoelectric sensor, respiration sensor, strain gauge, electrogoniometer, chewing sensor, swallow sensor, temperature sensor, and pressure sensor.

12. The device in claim 7 wherein a tamper-resisting mechanism monitors a person's mouth using face recognition methods and responds if the line of sight to the person's mouth is impaired when a person is probably eating based on a sensor, wherein this sensor is selected from the group consisting of: accelerometer, inclinometer, motion sensor, pedometer, sound sensor, smell sensor, blood pressure sensor, heart rate sensor, EEG sensor, ECG sensor, EMG sensor, electrochemical sensor, gastric activity sensor, GPS sensor, location sensor, image sensor, optical sensor, piezoelectric sensor, respiration sensor, strain gauge, electrogoniometer, chewing sensor, swallow sensor, temperature sensor, and pressure sensor.

13. The device in claim 7 wherein the computer uses one or more methods selected from the group consisting of: pattern recognition or identification; human motion recognition or identification; face recognition or identification; gesture recognition or identification; food recognition or identification; word recognition or identification; logo recognition or identification; bar code recognition or identification; and 3D modeling.

14. The device in claim 7 wherein the computer analyzes one or more factors selected from the group consisting of: number of reachable food sources; types of reachable food sources; changes in the volume of food at a reachable food source; number of times that the person brings food to their mouth; sizes of portions of food that the person brings to their mouth; number of chewing movements; frequency of speed of chewing movements; and number of swallowing movements.

15. The device in claim 7 wherein the computer provides an initial estimate of the types and quantities of food consumed by the person and this initial estimate is then refined by human interaction and/or evaluation.

16. The device in claim 7 wherein one or more food sources are selected from the group consisting of: food on a plate, food in a bowl, food in a glass, food in a cup, food in a bottle, food in a can, food in a package, food in a container, food in a wrapper, food in a bag, food in a box, food on a table, food on a counter, food on a shelf, and food in a refrigerator.

17. The device in claim 7 wherein estimates of the types and quantities of food consumed are used to estimate human caloric intake and wherein these estimates of human caloric intake are used in combination with estimates of human caloric expenditure as part of an overall system for human energy balance and human weight management.

18. The device in claim 7 wherein the tamper-resisting member detects and responds if the person's actual weight gain or loss is inconsistent with the predicted weight gain or loss predicted by the combination of the estimated caloric intake and the estimated caloric expenditure.

19. A tamper-resistant wearable device that automatically monitors caloric intake comprising:
- a motion sensor which is configured to be worn on the person's wrist;
- a first camera which is configured to be worn on a first narrow side of a person's wrist facing toward the person's mouth when the person eats and automatically take pictures of the person's mouth when the person eats;
a second camera which is configured to be worn on a second narrow side a person's wrist facing away from the person's mouth when the person eats and automatically take pictures of a reachable food source when the person eats, wherein a reachable food source is a food source that the person can reach by moving their arm, and wherein food can include liquid nourishment as well as solid food;
a tamper-resisting mechanism, wherein this tamper-resisting mechanism detects and responds when the cameras are removed from the person's body, and wherein this tamper-resisting mechanism detects and responds if the field of view of the first camera does not include the person's mouth and/or the field of view of the second camera does not include a reachable food source when the person eats; and
a computer which automatically analyzes pictures of the person's mouth and pictures of the reachable food source in order to estimate the types and quantities of food that are consumed by the person.

* * * * *